(12) United States Patent
Torres et al.

(10) Patent No.: US 9,657,103 B2
(45) Date of Patent: May 23, 2017

(54) METHODS OF TREATING AND PREVENTING STAPHYLOCOCCUS AUREUS INFECTIONS AND ASSOCIATED CONDITIONS

(71) Applicant: NEW YORK UNIVERSITY, New York, NY (US)

(72) Inventors: Victor J. Torres, New York, NY (US); Ashley L. Dumont, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/398,293

(22) PCT Filed: Mar. 15, 2013

(86) PCT No.: PCT/US2013/032436
§ 371 (c)(1),
(2) Date: Oct. 31, 2014

(87) PCT Pub. No.: WO2013/165613
PCT Pub. Date: Nov. 7, 2013

(65) Prior Publication Data
US 2015/0132310 A1   May 14, 2015

Related U.S. Application Data

(60) Provisional application No. 61/641,543, filed on May 2, 2012.

(51) Int. Cl.
| | |
|---|---|
| *A61K 39/395* | (2006.01) |
| *C07K 16/28* | (2006.01) |
| *C07K 14/31* | (2006.01) |
| *C07K 14/435* | (2006.01) |
| *C07K 14/705* | (2006.01) |
| *A61K 38/17* | (2006.01) |
| *A61K 45/06* | (2006.01) |
| *C07K 14/47* | (2006.01) |
| *G01N 33/569* | (2006.01) |
| *A61K 39/00* | (2006.01) |

(52) U.S. Cl.
CPC ...... *C07K 16/2845* (2013.01); *A61K 38/1741* (2013.01); *A61K 39/3955* (2013.01); *A61K 45/06* (2013.01); *C07K 14/31* (2013.01); *C07K 14/4354* (2013.01); *C07K 14/473* (2013.01); *C07K 14/70553* (2013.01); *G01N 33/56938* (2013.01); *A61K 2039/505* (2013.01); *C07K 2317/76* (2013.01); *C07K 2319/21* (2013.01)

(58) Field of Classification Search
None
See application file for complete search history.

(56) References Cited

U.S. PATENT DOCUMENTS

| | | |
|---|---|---|
| 2006/0063924 A1 | 3/2006 | Ni et al. |
| 2010/0310665 A1 | 12/2010 | Watson et al. |
| 2011/0306608 A1 | 12/2011 | Hayden et al. |

FOREIGN PATENT DOCUMENTS

| | | |
|---|---|---|
| JP | 2004504827 A | 2/2004 |
| JP | 200694701 A | 4/2006 |
| JP | 2007319073 A | 12/2007 |
| JP | 2008220174 A | 9/2008 |
| WO | 2004/066914 A2 | 8/2004 |
| WO | 2011/140337 A2 | 11/2011 |
| WO | 2012005800 A1 | 1/2012 |

OTHER PUBLICATIONS

First Office Action for China Application No. 201380034208.9 (Nov. 13, 2015).
Second Office Action for China Application No. 201380034208.9 (Apr. 8, 2016).
Third Office Action for China Application No. 201380034208.9 (Aug. 18, 2016).
Bansal et al., "Small Molecule Antagonists of Complement Receptor Type 3 Block Adhesion and Adhesion-Dependent Oxidative Burst in Human Polymorphonuclear Leukocytes," The Journal of Pharmacology and Experimental Therapeutics 304(3):1016-1024 (2003).
International Search Report and Written Opinion for corresponding International Application No. PCT/US2013/032436 filed Mar. 15, 2013 (mailed Sep. 10, 2013).
Extended Search Report and Opinion for European Patent Application No. 13784426.2 (mailed Jan. 5, 2016).
Gao et al., "Inactivation of CD11b in a Mouse Transgenic Model Protects Against Sepsis-Induced Lung PMN Infiltration and Vascular Injury," Physiol. Genomics 21(2):230-242 (2005).
Dumont et al., "Characterization of a New Cytotoxin That Contributes to *Staphylococcus aureus* Pathogenesis," Molec. Microbiol. 79(3):814-825 (2011).
Vandenesch et al., "*Staphylococcus aureus* Hemolysins, Bi-Component Leukocidins, and Cytolytic Peptides: A Redundant Arsenal of Membrane-Damaging Virulence Factors?," Frontiers in Cellular and Infection Microbiology 2(12):1-15 (Feb. 2012).
Cheung et al., "The Potential Use of Toxin Antibodies as a Strategy for Controlling Acute *Staphylococcus aureus* Infections," Expert Opin. Ther. Targets 16(6):601-612 (2012).
Hac et al., "Neutrophil Engagement and Septic Challenge in Acute Experimental Pancreatitis in Rats," World J. Gastroenterology 11(41):6459-6465 (2005).

(Continued)

*Primary Examiner* — J. Hines
*Assistant Examiner* — Khatol Shahnan Shah
(74) *Attorney, Agent, or Firm* — LeClairRyan, a Professional Corporation

(57) ABSTRACT

The present invention relates to methods of treating and preventing *Staphylococcus aureus* infection and/or a condition resulting from a *S. aureus* infection a subject that involves administering a CD11b inhibitor. The present invention further relates to a non-human transgenic animal expressing human CD11b and its use in methods of identifying novel therapeutics for the treatment and prevention of *Staphylococcus aureus* infection and/or a condition resulting from a *S. aureus* infection.

9 Claims, 11 Drawing Sheets

(56) References Cited

OTHER PUBLICATIONS

Alonzo et al., "The Bicomponent Pore-Forming Leucocidins of *Staphylococcus aureus*," Microbiol. Molec. Biol. Rev. 78(2):199-230 (2014).
Dumont et al., "Cell Targeting by the *Staphylococcus aureus* Pore-Forming Toxins: It's Not Just About Lipids," Trends Microbiol. 22(1):21-27 (2014).
Dumont et al., "*Staphylococcus aureus* LukAB Cytotoxin Kills Human Neutrophils by Targeting the CD11b Subunit of the Integrin Mac-1," PNAS 110(26):10794-10799 (2013).
English Translation and Notice of Reasons for Rejection for Japanese Patent Application No. 2015-510278 (Dec. 5, 2016).
Kato et al., "Influence of *Staphylococcal* Lipoteichoic Acid on the Frustrated Phagocytosis of Neutrophils Against Dpsonized Corneocytes," Exp. Dermatol. 2:171-174 (1993).
Krüll et al., "*Escherichia coli* Hemolysin and *Staphylococcus aureus* α-Toxin Potently Induce Neutrophil Adhesion to Cultured Human Endothelial Cells," J. Immunol. 157:4133-4140 (1996).

```
                         SEQUENCE LISTING

<160> NUMBER OF SEQ ID NOS: 24

<210> SEQ ID NO 1
<211> LENGTH: 4740
<212> TYPE: DNA
<213> ORGANISM: Homo sapiens

<400> SEQUENCE: 1
tggcttcctt gtggttcctc agtggtgcct gcaacccctg gttcacctcc ttccaggttc      60
tggctccttc cagccatggc tctcagagtc cttctgttaa cagccttgac cttatgtcat     120
gggttcaact tggacactga aaacgcaatg accttccaag agaacgcaag gggcttcggg     180
cagagcgtgg tccagcttca gggatccagg gtggtggttg agcccccca ggagatagtg      240 gctgccaacc aaagggggcag cctctaccag tgcgactaca gcacaggctc atgcgagccc    300
atccgcctgc aggtccccgt ggaggccgtg aacatgtccc tgggcctgtc cctggcagcc    360
accaccagcc cccctcagct gctggcctgt ggtcccaccg tgcaccagac ttgcagtgag    420
aacacgtatg tgaaagggct ctgcttcctg tttggatcca acctacggca gcagcccag     480 aagttcccag aggccctccg agggtgtcct caagaggata gtgacattgc cttcttgatt    540
gatggctctg gtagcatcat cccacatgac tttcggcgga tgaaggagtt tgtctcaact    600
gtgatggagc aattaaaaaa gtccaaaacc ttgttctctt tgatgcagta ctctgaagaa    660
ttccggattc actttacctt caaagagttc cagaacaacc ctaacccaag atcactggtg    720
aagccaataa cgcagctgct tgggcggaca cacacggcca cgggcatccg caaagtggta    780
cgagagctgt ttaacatcac caacggagcc cgaaagaatg cctttaagat cctagttgtc    840
atcacggatg gagaaaagtt tggcgatccc ttgggatatg aggatgtcat ccctgaggca    900
gacagagagg gagtcattcg ctacgtcatt ggggtgggag atgccttccg cagtgagaaa    960
tcccgccaag agcttaatac catcgcatcc aagccgcctc gtgatcacgt gttccaggtg   1020
aataactttg aggctctgaa gaccattcag aaccagcttc gggagaagat ctttgcgatc   1080
gagggtactc agacaggaag tagcagctcc tttgagcatg agatgtctca ggaaggcttc   1140
agcgctgcca tcacctctaa tggcccccttg ctgagcactg tggggagcta tgactgggct   1200
ggtggagtct ttctatatac atcaaggag aaaagcacct tcatcaacat gaccagagtg   1260
gattcagaca tgaatgatgc ttacttgggt tatgctgccg ccatcatctt acggaaccgg   1320
gtgcaaagcc tggttctggg ggcacctcga tatcagcaca tcggcctggt agcgatgttc   1380
aggcagaaca ctggcatgtg ggagtccaac gctaatgtca agggcaccca gatcggcgcc   1440
tacttcgggg cctccctctg ctccgtggac gtggacagca acggcagcac cgacctggtc   1500
ctcatcgggg ccccccatta ctacgagcag acccgagggg gccaggtgtc cgtgtgccccc   1560 ttgcccaggg ggagggctcg gtggcagtgt gatgctgttc tctacgggga gcagggccaa    1620
ccctggggcc gctttgggc agccctaaca gtgctggggg acgtaaatgg ggacaagctg    1680
acggacgtgg ccattggggc cccaggagag gaggacaacc ggggtgctgt ttacctgttt    1740
cacggaacct caggatctgg catcagcccc tcccatagcc agcggatagc aggctccaag    1800 ctctctcca ggctccagta ttttggtcag tcactgagtg ggggccagga cctcacaatg    1860
gatggactgg tagacctgac tgtaggagcc caggggcacg tgctgctgct caggtcccag    1920
```

```
ccagtactga gagtcaaggc aatcatggag ttcaatccca gggaagtggc aaggaatgta    1980
tttgagtgta atgatcaggt ggtgaaaggc aaggaagccg agagggtcag agtctgcctc    2040
catgtccaga agagcacacg ggatcggcta agagaaggac agatccagag tgttgtgact    2100
tatgacctgg ctctggactc cggccgccca cattcccgcg ccgtcttcaa tgagacaaag    2160
aacagcacac gcagacagac acaggtcttg gggctgaccc agacttgtga gaccctgaaa    2220
ctacagttgc cgaattgcat cgaggaccca gtgagcccca ttgtgctgcg cctgaacttc    2280
tctctggtgg gaacgccatt gtctgctttc gggaacctcc ggccagtgct ggcggaggat    2340
gctcagagac tcttcacagc cttgtttccc tttgagaaga attgtggcaa tgacaacatc    2400
tgccaggatg acctcagcat caccttcagt ttcatgagcc tggactgcct cgtggtgggt    2460
gggcccgggg agttcaacgt gacagtgact gtgagaaatg atggtgagga ctcctacagg    2520
acacaggtca ccttcttctt cccgcttgac ctgtcctacc ggaaggtgtc cacactccag    2580
aaccagcgct cacagcgatc ctggcgcctg gcctgtgagt ctgcctcctc caccgaagtg    2640
tctggggcct tgaagagcac cagctgcagc ataaaccacc ccatcttccc ggaaaactca    2700
gaggtcaacct ttaatatcac gtttgatgta gactctaagg cttcccttgg aaacaaactg    2760
ctcctcaagg ccaatgtgac cagtgagaac aacatgccca gaaccaacaa aaccgaattc    2820
caactggagc tgccggtgaa atatgctgtc tacatggtgg tcaccagcca tggggtctcc    2880
actaaatatc tcaacttcac ggcctcagag aataccagtc gggtcatgca gcatcaatat    2940
caggtcagca acctggggca gaggagcccc cccatcagcc tggtgttctt ggtgcccgtc    3000
cggctgaacc agactgtcat atgggaccgc ccccaggtca ccttctccga gaacctctcg    3060
agtacgtgcc acaccaagga gcgcttgccc tctcactccg actttctggc tgagcttcgg    3120
aaggcccccg tggtgaactg ctccatcgct gtctgccaga gaatccagtg tgacatcccg    3180
ttctttggca tccaggaaga attcaatgct acccctcaaag gcaacctctc gtttgactgg    3240
tacatcaaga cctcgcataa ccacctcctg atcgtgagca cagctgagat cttgttttaac    3300
gattccgtgt tcaccctgct gccgggacag ggggcgtttg tgaggtccca gacggagacc    3360
aaaagtggagc cgttcgaggt ccccaacccc ctgccgctca tcgtgggcag ctctgtcggg    3420
ggactgctgc tcctggcccct catcaccgcc gcgctgtaca agctcggctt cttcaagcgg    3480
caatacaagg acatgatgag tgaaggggggt ccccgggggg ccgaacccca gtagcggctc    3540
cttcccgaca gagctgcctc tcggtggcca gcaggactct gcccagacca cacgagcccc    3600
caggctgctg gacacgtcgg acagcgaagt atccccgaca ggacgggctt gggcttccat    3660
ttgtgtgtgt gcaagtgtgt atgtgcgtgt gtgcgagtgt gtgcaagtgt ctgtgtgcaa    3720
gtgtgtgcac gtgtgcgtgt gcgtgcatgt gcactcgcac gcccatgtgt gagtgtgtgc    3780
aagtatgtga gtgtgtccag tgtgtgtgcg tgtgtccatg tgtgtgcagt gtgtgcatgt    3840
gtgcgagtgt gtgcatgtgt gtgctcaggg gctgtggctc acgtgtgtga ctcagagtgt    3900
ctctggcgtg tgggtaggtg acggcagcgt agcctctccg gcagaaggga actgcctggg    3960
ctcccttgtg cgtgggtaag ccgctgctgg gttttcctcc gggagagggg acggtcaatc    4020
ctgtgggtga agagagaggg aaacacagca gcatctctcc actgaaagaa gtgggacttc    4080
ccgtcgcctg cgagcctgcg gcctgctgga gcctgcgcag cttggatgga tactccatga    4140
gaaaagccgt gggtggaacc aggagcctcc tccacaccag cgctgatgcc caataaagat    4200
gcccactgag gaatcatgaa gcttcctttc tggattcatt tattatttca atgtgacttt    4260
```

-continued

```
aattttttgg atggataagc ctgtctatgg tacaaaaatc acaaggcatt caagtgtaca    4320
gtgaaaagtc tcccttttcca gatattcaag tcacctcctt aaaggtagtc aagattgtgt   4380
tttgaggttt ccttcagaca gattccaggc gatgtgcaag tgtatgcacg tgtgcacaca    4440
ccacacacat acacacacac aagcttttt acacaaatgg tagcatactt tatattggtc    4500
tgtatcttgc ttttttcac caatatttct cagacatcgg ttcatattaa gacataaatt    4560 acttttcat tcttttatac cgctgcatag tattccattg tgtgagtgta ccataatgta    4620
tttaaccagt cttcttttga tatactattt tcatctcttg ttattgcatc tgctgagtta    4680
ataaatcaaa tatgtcaa aaaaaaaaaa aaaaaaaaa aaaaaaaaa aaaaaaaat       4740
```

<210> SEQ ID NO 2
<211> LENGTH: 1152
<212> TYPE: PRT
<213> ORGANISM: Homo sapiens

<400> SEQUENCE: 2

```
Met Ala Leu Arg Val Leu Leu Thr Ala Leu Thr Leu Cys His Gly
1               5                   10                  15

Phe Asn Leu Asp Thr Glu Asn Ala Met Thr Phe Gln Glu Asn Ala Arg
                20                  25                  30

Gly Phe Gly Gln Ser Val Val Gln Leu Gln Gly Ser Arg Val Val Val
            35                  40                  45

Gly Ala Pro Gln Glu Ile Val Ala Ala Asn Gln Arg Gly Ser Leu Tyr
        50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
```

```
                 290                 295                 300
Ser Lys Pro Pro Arg Asp His Val Phe Gln Val Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
                340                 345                 350

Glu Gly Phe Ser Ala Ala Ile Thr Ser Asn Gly Pro Leu Leu Ser Thr
                355                 360                 365

Val Gly Ser Tyr Asp Trp Ala Gly Val Phe Leu Tyr Thr Ser Lys
        370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
                420                 425                 430

Ala Met Phe Arg Gln Asn Thr Gly Met Trp Glu Ser Asn Ala Asn Val
        435                 440                 445

Lys Gly Thr Gln Ile Gly Ala Tyr Phe Gly Ala Ser Leu Cys Ser Val
        450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Arg Ala Arg Trp Gln Cys Asp Ala Val Leu Tyr Gly Glu
                500                 505                 510

Gln Gly Gln Pro Trp Gly Arg Phe Gly Ala Ala Leu Thr Val Leu Gly
        515                 520                 525

Asp Val Asn Gly Asp Lys Leu Thr Asp Val Ala Ile Gly Ala Pro Gly
        530                 535                 540

Glu Glu Asp Asn Arg Gly Ala Val Tyr Leu Phe His Gly Thr Ser Gly
545                 550                 555                 560

Ser Gly Ile Ser Pro Ser His Ser Gln Arg Ile Ala Gly Ser Lys Leu
                565                 570                 575

Ser Pro Arg Leu Gln Tyr Phe Gly Gln Ser Leu Ser Gly Gly Gln Asp
                580                 585                 590

Leu Thr Met Asp Gly Leu Val Asp Leu Thr Val Gly Ala Gln Gly His
        595                 600                 605

Val Leu Leu Leu Arg Ser Gln Pro Val Leu Arg Val Lys Ala Ile Met
610                 615                 620

Glu Phe Asn Pro Arg Glu Val Ala Arg Asn Val Phe Glu Cys Asn Asp
625                 630                 635                 640

Gln Val Val Lys Gly Lys Glu Ala Gly Glu Val Arg Val Cys Leu His
                645                 650                 655

Val Gln Lys Ser Thr Arg Asp Arg Leu Arg Glu Gly Gln Ile Gln Ser
                660                 665                 670

Val Val Thr Tyr Asp Leu Ala Leu Asp Ser Gly Arg Pro His Ser Arg
        675                 680                 685

Ala Val Phe Asn Glu Thr Lys Asn Ser Thr Arg Arg Gln Thr Gln Val
        690                 695                 700

Leu Gly Leu Thr Gln Thr Cys Glu Thr Leu Lys Leu Gln Leu Pro Asn
705                 710                 715                 720
```

-continued

Cys Ile Glu Asp Pro Val Ser Pro Ile Val Leu Arg Leu Asn Phe Ser
            725                 730                 735

Leu Val Gly Thr Pro Leu Ser Ala Phe Gly Asn Leu Arg Pro Val Leu
        740                 745                 750

Ala Glu Asp Ala Gln Arg Leu Phe Thr Ala Leu Phe Pro Phe Glu Lys
            755                 760                 765

Asn Cys Gly Asn Asp Asn Ile Cys Gln Asp Asp Leu Ser Ile Thr Phe
770                 775                 780

Ser Phe Met Ser Leu Asp Cys Leu Val Val Gly Gly Pro Arg Glu Phe
785                 790                 795                 800

Asn Val Thr Val Thr Val Arg Asn Asp Gly Asp Ser Tyr Arg Thr
            805                 810                 815

Gln Val Thr Phe Phe Pro Leu Asp Leu Ser Tyr Arg Lys Val Ser
            820                 825                 830

Thr Leu Gln Asn Gln Arg Ser Gln Arg Ser Trp Arg Leu Ala Cys Glu
            835                 840                 845

Ser Ala Ser Ser Thr Glu Val Ser Gly Ala Leu Lys Ser Thr Ser Cys
        850                 855                 860

Ser Ile Asn His Pro Ile Phe Pro Glu Asn Ser Glu Val Thr Phe Asn
865                 870                 875                 880

Ile Thr Phe Asp Val Asp Ser Lys Ala Ser Leu Gly Asn Lys Leu Leu
                885                 890                 895

Leu Lys Ala Asn Val Thr Ser Glu Asn Asn Met Pro Arg Thr Asn Lys
            900                 905                 910

Thr Glu Phe Gln Leu Glu Leu Pro Val Lys Tyr Ala Val Tyr Met Val
            915                 920                 925

Val Thr Ser His Gly Val Ser Thr Lys Tyr Leu Asn Phe Thr Ala Ser
        930                 935                 940

Glu Asn Thr Ser Arg Val Met Gln His Gln Tyr Gln Val Ser Asn Leu
945                 950                 955                 960

Gly Gln Arg Ser Pro Pro Ile Ser Leu Val Phe Leu Val Pro Val Arg
                965                 970                 975

Leu Asn Gln Thr Val Ile Trp Asp Arg Pro Gln Val Thr Phe Ser Glu
            980                 985                 990

Asn Leu Ser Ser Thr Cys His Thr Lys Glu Arg Leu Pro Ser His Ser
            995                 1000                1005

Asp Phe Leu Ala Glu Leu Arg Lys Ala Pro Val Val Asn Cys Ser
    1010                1015                1020

Ile Ala Val Cys Gln Arg Ile Gln Cys Asp Ile Pro Phe Phe Gly
    1025                1030                1035

Ile Gln Glu Glu Phe Asn Ala Thr Leu Lys Gly Asn Leu Ser Phe
    1040                1045                1050

Asp Trp Tyr Ile Lys Thr Ser His Asn His Leu Leu Ile Val Ser
    1055                1060                1065

Thr Ala Glu Ile Leu Phe Asn Asp Ser Val Phe Thr Leu Leu Pro
    1070                1075                1080

Gly Gln Gly Ala Phe Val Arg Ser Gln Thr Glu Thr Lys Val Glu
    1085                1090                1095

Pro Phe Glu Val Pro Asn Pro Leu Pro Leu Ile Val Gly Ser Ser
    1100                1105                1110

Val Gly Gly Leu Leu Leu Leu Ala Leu Ile Thr Ala Ala Leu Tyr
    1115                1120                1125

```
                Lys Leu Gly Phe Phe Lys Arg     Gln Tyr Lys Asp Met     Met Ser Glu
                    1130                1135                    1140

Gly Gly Pro Pro Gly Ala Glu     Pro Gln
                    1145                1150

<210> SEQ ID NO 3
<211> LENGTH: 4745
<212> TYPE: DNA
<213> ORGANISM: Homo sapiens

<400> SEQUENCE: 3
ttttctgccc ttctttgctt tggtggcttc cttgtggttc ctcagtggtg cctgcaaccc        60
ctggttcacc tccttccagg ttctggctcc ttccagccat ggctctcaga gtccttctgt       120
taacagcctt gacttatgt catgggttca acttggacac tgaaaacgca atgaccttcc        180
aagagaacgc aaggggcttc gggcagagcg tggtccagct tcagggatcc agggtggtgg       240
ttggagcccc ccaggagata gtggctgcca accaaagggg cagcctctac cagtgcgact       300
acagcacagg ctcatgcgag cccatccgcc tgcaggtccc cgtggaggcc gtgaacatgt       360
ccctgggcct gtccctggca gccaccacca gccccctca gctgctggcc tgtggtccca       420
ccgtgcacca gacttgcagt gagaacacgt atgtgaaagg gctctgcttc ctgtttggat       480
ccaacctacg gcagcagccc cagaagttcc cagaggccct ccgagggtgt cctcaagagg       540
atagtgacat tgccttcttg attgatggct ctggtagcat catcccacat gactttcggc       600
ggatgaagga gtttgtctca actgtgatgg agcaattaaa aaagtccaaa accttgttct       660
ctttgatgca gtactctgaa gaattccgga ttcactttac cttcaaagag ttccagaaca       720
accctaaccc aagatcactg gtgaagccaa tacgcagct gcttgggcgg acacacacgg       780
ccacgggcat ccgcaaagtg gtacgagagc tgtttaacat caccaacgga gcccgaaaga       840
atgcctttaa gatcctagtt gtcatcacgg atggagaaaa gttttggcgat cccttgggat       900 atgaggatgt catccctgag gcagacagag agggagtcat cgctacgtc attggggtgg       960 gagatgcctt ccgcagtgag aaatcccgcc aagagcttaa taccatcgca tccaagccgc      1020
ctcgtgatca cgtgttccag gtgaataact tgaggctct gaagaccatt cagaaccagc      1080
ttcgggagaa gatctttgcg atcgagggta ctcagacagg aagtagcagc tcctttgagc      1140
atgagatgtc tcaggaaggc ttcagcgctg ccatcacctc taatgccccc ttgctgagca      1200
ctgtggggag ctatgactgg gctggtggag tctttctata tacatcaaag gagaaaagca      1260
ccttcatcaa catgaccaga gtggattcag acatgaatga tgcttacttg ggttatgctg      1320
ccgccatcat cttacggaac cgggtgcaaa gcctggttct gggggcacct cgatatcagc      1380
acatcggcct ggtagcgatg ttcaggcaga acactggcat gtgggagtcc aacgctaatg      1440
tcaagggcac ccagatcggc gcctacttcg gggcctccct ctgctccgtg gacgtggaca      1500
gcaacggcag caccgacctg gtcctcatcg gggcccccca ttactacgag cagacccgag      1560
ggggccaggt gtccgtgtgc cccttgccca ggggcagag ggctcggtgg cagtgtgatg      1620
ctgttctcta cggggagcag ggccaaccct ggggccgctt tgggcagcc ctaacagtgc      1680 tgggggacgt aaatggggac aagctgacgg acgtggccat tggggccca ggagaggagg      1740 acaaccgggg tgctgtttac ctgttcacg gaacctcagg atctggcatc agcccctccc      1800
atagccagcg gatagcaggc tccaagctct ctcccaggct ccagtatttt ggtcagtcac      1860
tgagtggggg ccaggacctc acaatggatg gactggtaga cctgactgta ggagcccagg      1920
ggcacgtgct gctgctcagg tcccagccag tactgagagt caaggcaatc atggagttca      1980
```

```
atcccaggga agtggcaagg aatgtatttg agtgtaatga tcaggtggtg aaaggcaagg    2040
aagccggaga ggtcagagtc tgcctccatg tccagaagag cacacgggat cggctaagag    2100
aaggacagat ccagagtgtt gtgacttatg acctggctct ggactccggc cgcccacatt    2160
cccgcgccgt cttcaatgag acaaagaaca gcacacgcag acagacacag gtcttggggc    2220
tgacccagac ttgtgagacc ctgaaactac agttgccgaa ttgcatcgag acccagtga    2280 gccccattgt gctgcgcctg aacttctctc tggtgggaac gccattgtct gctttcggga    2340
acctccggcc agtgctggcg gaggatgctc agagactctt cacagccttg tttcccttg    2400 agaagaattg tggcaatgac aacatctgcc aggatgacct cagcatcacc ttcagtttca    2460
tgagcctgga ctgcctcgtg gtgggtgggc ccgggagtt caacgtgaca gtgactgtga    2520
gaaatgatgg tgaggactcc tacaggacac aggtcacctt cttcttcccg cttgacctgt    2580
cctaccggaa ggtgtccacg ctccagaacc agcgctcaca gcgatcctgg cgcctggcct    2640
gtgagtctgc ctcctccacc gaagtgtctg gggccttgaa gagcaccagc tgcagcataa    2700 accacccat cttcccggaa aactcagagg tcaccttta tatcacgttt gatgtagact    2760
ctaaggcttc ccttggaaac aaactgctcc tcaaggccaa tgtgaccagt gagaacaaca    2820
tgcccagaac caacaaaacc gaattccaac tggagctgcc ggtgaaatat gctgtctaca    2880
tggtggtcac cagccatggg gtctccacta aatatctcaa cttcacggcc tcagagaata    2940
ccagtcgggt catgcagcat caatatcagg tcagcaacct ggggcagagg agcctcccca    3000
tcagcctggt gttcttggtg cccgtccggc tgaaccagac tgtcatatgg gaccgccccc    3060
aggtcacctt ctccgagaac ctctcgagta cgtgccacac caaggagcgc ttgccctctc    3120
actccgactt tctggctgag cttcggaagg ccccgtggt gaactgctcc atcgctgtct    3180
gccagagaat ccagtgtgac atcccgttct ttggcatcca ggaagaattc aatgctaccc    3240
tcaaaggcaa cctctcgttt gactggtaca tcaagacctc gcataaccac ctcctgatcg    3300
tgagcacagc tgagatcttg tttaacgatt ccgtgttcac cctgctgccg ggacagggg    3360 cgtttgtgag gtcccagacg gagaccaaag tggagccgtt cgaggtcccc aaccccctgc    3420
cgctcatcgt gggcagctct gtcggggac tgctgctcct ggccctcatc accgccgcgc    3480
tgtacaagct cggcttcttc aagcggcaat acaaggacat gatgagtgaa gggggtcccc    3540 cggggggccga accccagtag cggctccttc ccgacagagc tgcctctcgg tggccagcag    3600
gactctgccc agaccacacg tagcccccag gctgctggac acgtcggaca gcgaagtatc    3660
cccgacagga cgggcttggg cttccatttg tgtgtgtgca agtgtgtatg tgcgtgtgtg    3720
caagtgtctg tgtgcaagtg tgtgcacatg tgtgcgtgtg cgtgcatgtg cacttgcacg    3780
cccatgtgtg agtgtgtgca agtatgtgag tgtgtccaag tgtgtgtgcg tgtgtccatg    3840
tgtgtgcaag tgtgtgcatg tgtgcgagtg tgtgcatgtg tgtgctcagg ggcgtgtggc    3900
tcacgtgtgt gactcagatg tctctggcgt gtgggtaggt gacggcagcg tagcctctcc    3960
ggcagaaggg aactgcctgg gctcccttgt gcgtgggtga agccgctgct gggttttcct    4020
ccgggagagg ggacggtcaa tcctgtgggt gaagacagag ggaaacacag cagcttctct    4080
ccactgaaag aagtggggact tcccgtcgcc tgcgagcctg cggcctgctg gagcctgcgc    4140
agcttggatg gagactccat gagaagccgt gggtggaacc aggaacctcc tccacaccag    4200
cgctgatgcc caataaagat gcccactgag gaatgatgaa gcttcctttc tggattcatt    4260
tattatttca atgtgacttt aattttttgg atggataagc ttgtctatgg tacaaaaatc    4320
```

```
acaaggcatt caagtgtaca gtgaaaagtc tcccttttcca gatattcaag tcacctcctt    4380
aaaggtagtc aagattgtgt tttgaggttt ccttcagaca gattccaggc gatgtgcaag    4440
tgtatgcacg tgtgcacaca caccacacat acacacacac aagctttttt acacaaatgg    4500
tagcatactt tatattggtc tgtatcttgc ttttttttcac caatatttct cagacatcgg    4560
ttcatattaa gacataaatt acttttttcat tcttttatac cgctgcatag tattccattg    4620
tgtgagtgta ccataatgta tttaaccagt cttcttttga tatactattt tcattctctt    4680
gttattgcat caatgctgag ttaataaatc aaatatatgt catttttgca tatatgtaag    4740
gataa    4745

<210> SEQ ID NO 4
<211> LENGTH: 1153
<212> TYPE: PRT
<213> ORGANISM: Homo sapiens

<400> SEQUENCE: 4
```

Met Ala Leu Arg Val Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala

```
                290                 295                 300
Ser Lys Pro Pro Arg Asp His Val Phe Gln Val Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Phe Glu His Glu Met Ser Gln
                340                 345                 350

Glu Gly Phe Ser Ala Ala Ile Thr Ser Asn Gly Pro Leu Leu Ser Thr
                355                 360                 365

Val Gly Ser Tyr Asp Trp Ala Gly Gly Val Phe Leu Tyr Thr Ser Lys
                370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
                420                 425                 430

Ala Met Phe Arg Gln Asn Thr Gly Met Trp Glu Ser Asn Ala Asn Val
                435                 440                 445

Lys Gly Thr Gln Ile Gly Ala Tyr Phe Gly Ala Ser Leu Cys Ser Val
                450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Gln Arg Ala Arg Trp Gln Cys Asp Ala Val Leu Tyr Gly
                500                 505                 510

Glu Gln Gly Gln Pro Trp Gly Arg Phe Gly Ala Ala Leu Thr Val Leu
                515                 520                 525

Gly Asp Val Asn Gly Asp Lys Leu Thr Asp Val Ala Ile Gly Ala Pro
                530                 535                 540

Gly Glu Glu Asp Asn Arg Gly Ala Val Tyr Leu Phe His Gly Thr Ser
545                 550                 555                 560

Gly Ser Gly Ile Ser Pro Ser His Ser Gln Arg Ile Ala Gly Ser Lys
                565                 570                 575

Leu Ser Pro Arg Leu Gln Tyr Phe Gly Gln Ser Leu Ser Gly Gly Gln
                580                 585                 590

Asp Leu Thr Met Asp Gly Leu Val Asp Leu Thr Val Gly Ala Gln Gly
                595                 600                 605

His Val Leu Leu Leu Arg Ser Gln Pro Val Leu Arg Val Lys Ala Ile
                610                 615                 620

Met Glu Phe Asn Pro Arg Glu Val Ala Arg Asn Val Phe Glu Cys Asn
625                 630                 635                 640

Asp Gln Val Val Lys Gly Lys Glu Ala Gly Glu Val Arg Val Cys Leu
                645                 650                 655

His Val Gln Lys Ser Thr Arg Asp Arg Leu Arg Glu Gly Gln Ile Gln
                660                 665                 670

Ser Val Val Thr Tyr Asp Leu Ala Leu Asp Ser Gly Arg Pro His Ser
                675                 680                 685

Arg Ala Val Phe Asn Glu Thr Lys Asn Ser Thr Arg Arg Gln Thr Gln
                690                 695                 700

Val Leu Gly Leu Thr Gln Thr Cys Glu Thr Leu Lys Leu Gln Leu Pro
705                 710                 715                 720
```

```
Asn Cys Ile Glu Asp Pro Val Ser Pro Ile Val Arg Leu Asn Phe
            725                 730                 735

Ser Leu Val Gly Thr Pro Leu Ser Ala Phe Gly Asn Leu Arg Pro Val
            740                 745                 750

Leu Ala Glu Asp Ala Gln Arg Leu Phe Thr Ala Leu Phe Pro Phe Glu
            755                 760                 765

Lys Asn Cys Gly Asn Asp Asn Ile Cys Gln Asp Asp Leu Ser Ile Thr
770                 775                 780

Phe Ser Phe Met Ser Leu Asp Cys Leu Val Val Gly Gly Pro Arg Glu
785                 790                 795                 800

Phe Asn Val Thr Val Thr Val Arg Asn Asp Gly Glu Asp Ser Tyr Arg
                805                 810                 815

Thr Gln Val Thr Phe Phe Pro Leu Asp Leu Ser Tyr Arg Lys Val
            820                 825                 830

Ser Thr Leu Gln Asn Gln Arg Ser Gln Arg Ser Trp Arg Leu Ala Cys
            835                 840                 845

Glu Ser Ala Ser Ser Thr Glu Val Ser Gly Ala Leu Lys Ser Thr Ser
850                 855                 860

Cys Ser Ile Asn His Pro Ile Phe Pro Glu Asn Ser Glu Val Thr Phe
865                 870                 875                 880

Asn Ile Thr Phe Asp Val Asp Ser Lys Ala Ser Leu Gly Asn Lys Leu
                885                 890                 895

Leu Leu Lys Ala Asn Val Thr Ser Glu Asn Asn Met Pro Arg Thr Asn
            900                 905                 910

Lys Thr Glu Phe Gln Leu Glu Leu Pro Val Lys Tyr Ala Val Tyr Met
            915                 920                 925

Val Val Thr Ser His Gly Val Ser Thr Lys Tyr Leu Asn Phe Thr Ala
            930                 935                 940

Ser Glu Asn Thr Ser Arg Val Met Gln His Gln Tyr Gln Val Ser Asn
945                 950                 955                 960

Leu Gly Gln Arg Ser Leu Pro Ile Ser Leu Val Phe Leu Val Pro Val
                965                 970                 975

Arg Leu Asn Gln Thr Val Ile Trp Asp Arg Pro Gln Val Thr Phe Ser
            980                 985                 990

Glu Asn Leu Ser Ser Thr Cys His Thr Lys Glu Arg Leu Pro Ser His
995                 1000                1005

Ser Asp Phe Leu Ala Glu Leu Arg Lys Ala Pro Val Val Asn Cys
        1010                1015                1020

Ser Ile Ala Val Cys Gln Arg Ile Gln Cys Asp Ile Pro Phe Phe
        1025                1030                1035

Gly Ile Gln Glu Glu Phe Asn Ala Thr Leu Lys Gly Asn Leu Ser
        1040                1045                1050

Phe Asp Trp Tyr Ile Lys Thr Ser His Asn His Leu Leu Ile Val
        1055                1060                1065

Ser Thr Ala Glu Ile Leu Phe Asn Asp Ser Val Phe Thr Leu Leu
        1070                1075                1080

Pro Gly Gln Gly Ala Phe Val Arg Ser Gln Thr Glu Thr Lys Val
        1085                1090                1095

Glu Pro Phe Glu Val Pro Asn Pro Leu Pro Leu Ile Val Gly Ser
        1100                1105                1110

Ser Val Gly Gly Leu Leu Leu Leu Ala Leu Ile Thr Ala Ala Leu
        1115                1120                1125
```

Tyr Lys  Leu Gly Phe Phe Lys  Arg Gln Tyr Lys Asp  Met Met Ser
    1130              1135                 1140

Glu Gly  Gly Pro Pro Gly Ala  Glu Pro Gln
    1145             1150

<210> SEQ ID NO 5
<211> LENGTH: 32
<212> TYPE: DNA
<213> ORGANISM: Artificial
<220> FEATURE:
<223> OTHER INFORMATION: Primer

<400> SEQUENCE: 5 cccccccgggg tgttatttga tttcgttcta tg                                32

<210> SEQ ID NO 6
<211> LENGTH: 50
<212> TYPE: DNA
<213> ORGANISM: Artificial
<220> FEATURE:
<223> OTHER INFORMATION: Primer

<400> SEQUENCE: 6
cccggatccg tggtggtggt ggtggtgagc tgaatttgct tgagtcgttg              50

<210> SEQ ID NO 7
<211> LENGTH: 40
<212> TYPE: DNA
<213> ORGANISM: Artificial
<220> FEATURE:
<223> OTHER INFORMATION: Primer

<400> SEQUENCE: 7
cccggatcct ctagaaaggg cggattacta atgattaaac                         40

<210> SEQ ID NO 8
<211> LENGTH: 36
<212> TYPE: DNA
<213> ORGANISM: Artificial
<220> FEATURE:
<223> OTHER INFORMATION: Primer

<400> SEQUENCE: 8
cccctgcagt tatttctttt cattatcatt aagtac                             36

<210> SEQ ID NO 9
<211> LENGTH: 33
<212> TYPE: DNA
<213> ORGANISM: Artificial
<220> FEATURE:
<223> OTHER INFORMATION: Primer

<400> SEQUENCE: 9
cccggatccc ataaagactc tcaagaccaa aat                                33

<210> SEQ ID NO 10
<211> LENGTH: 34
<212> TYPE: DNA
<213> ORGANISM: Artificial
<220> FEATURE:
<223> OTHER INFORMATION: Primer

<400> SEQUENCE: 10
ccctctagat tatccttctt tataaggttt attg                               34

<210> SEQ ID NO 11
<211> LENGTH: 36
<212> TYPE: DNA
<213> ORGANISM: Artificial
<220> FEATURE:
<223> OTHER INFORMATION: Primer

<400> SEQUENCE: 11
tgactctaga ccaccatggc tctcagagtc cttctg                          36

<210> SEQ ID NO 12
<211> LENGTH: 40
<212> TYPE: DNA
<213> ORGANISM: Artificial
<220> FEATURE:
<223> OTHER INFORMATION: Primer

<400> SEQUENCE: 12
gctgctactt cctgtctgag tttgaggaca ccctcggagg                      40

<210> SEQ ID NO 13
<211> LENGTH: 40
<212> TYPE: DNA
<213> ORGANISM: Artificial
<220> FEATURE:
<223> OTHER INFORMATION: Primer

<400> SEQUENCE: 13
cctccgaggg tgtcctcaaa ctcagacagg aagtagcagc                      40

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
tttgcggccg cagcccaagc ccgtcctgtc                                 30

<210> SEQ ID NO 15
<211> LENGTH: 36
<212> TYPE: DNA
<213> ORGANISM: Artificial
<220> FEATURE:
<223> OTHER INFORMATION: Primer

<400> SEQUENCE: 15
tgactctaga ccaccatggc tctcagagtc cttctg                          36

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
tttgcggccg cagcccaagc ccgtcctgtc                                 30

<210> SEQ ID NO 17
<211> LENGTH: 57
<212> TYPE: DNA
<213> ORGANISM: Artificial
<220> FEATURE:
<223> OTHER INFORMATION: shRNA for CD11b

<400> SEQUENCE: 17
ccggcgcaat gaccttccaa gagaactcga gttctcttgg aaggtcattg cgtttttt    57

<210> SEQ ID NO 18
<211> LENGTH: 57
<212> TYPE: DNA
<213> ORGANISM: Artificial
<220> FEATURE:
<223> OTHER INFORMATION: shRNA for CD18

<400> SEQUENCE: 18
ccgggaaacc caggaagacc acaatctcga gattgtggtc ttcctgggtt tctttttt    57

<210> SEQ ID NO 19
<211> LENGTH: 38
<212> TYPE: DNA
<213> ORGANISM: Artificial
<220> FEATURE:
<223> OTHER INFORMATION: Primer

<400> SEQUENCE: 19
ccccggatcc tgtaattcag ctcataaaga ctctcaag                         38

<210> SEQ ID NO 20
<211> LENGTH: 34
<212> TYPE: DNA
<213> ORGANISM: Artificial
<220> FEATURE:
<223> OTHER INFORMATION: Primer

<400> SEQUENCE: 20
ccctctagat tatccttctt tataaggttt attg                              34

<210> SEQ ID NO 21
<211> LENGTH: 30
<212> TYPE: DNA
<213> ORGANISM: Artificial
<220> FEATURE:
<223> OTHER INFORMATION: Primer

<400> SEQUENCE: 21
tttcatatgg gatccaacct acggcagcag                                   30

<210> SEQ ID NO 22
<211> LENGTH: 117
<212> TYPE: DNA
<213> ORGANISM: Artificial
<220> FEATURE:
<223> OTHER INFORMATION: Primer

<400> SEQUENCE: 22
tttctcgagt tacttgtcat cgtcatcctt gtaatcgata tcatgatctt tataatcacc    60
gtcatggtct ttgtagtctc ctcctcctcc tcctcccgca aagatcttct cccgaag       117

<210> SEQ ID NO 23
<211> LENGTH: 29
<212> TYPE: DNA
<213> ORGANISM: Artificial
<220> FEATURE:
<223> OTHER INFORMATION: Primer

<400> SEQUENCE: 23
tttcatatgg gctccaacct gctgaggcc                                    29

```
<210> SEQ ID NO 24
<211> LENGTH: 120
<212> TYPE: DNA
<213> ORGANISM: Artificial
<220> FEATURE:
<223> OTHER INFORMATION: Primer

<400> SEQUENCE: 24
tttctcgagt tacttgtcat cgtcatcctt gtaatcgata tcatgatctt tataatcacc      60
gtcatggtct ttgtagtctc ctcctcctcc tcctcctgca aagatctttt cctgaagctg     120
```

METHODS OF TREATING AND PREVENTING *STAPHYLOCOCCUS AUREUS* INFECTIONS AND ASSOCIATED CONDITIONS

This application is a national stage application under 35 U.S.C. 371 from PCT Application No. PCT/US2013/032436, filed Mar. 15, 2013, which claims the benefit of U.S. Provisional Patent Application Ser. No. 61/641,543, filed May 2, 2012, which are hereby incorporated by reference in their entirety.

This invention was made with government support under grant number 1R56AI091856-01A1 awarded by the National Institutes of Health. The government has certain rights in this invention.

FIELD OF THE INVENTION

This invention relates to methods of treating and preventing *Staphylococcus aureus* infections, and to methods of identifying novel therapeutics for the treatment and prevention of *Staphylococcus aureus* infections.

BACKGROUND OF THE INVENTION

*Staphylococcus aureus* ("*S. aureus*") is a bacterium that commensally colonizes more than 25% of the human population. Importantly, this organism is capable of breaching its initial site of colonization, resulting in bacterial dissemination and disease. *S. aureus* is the leading cause of nosocomial infections, is the most common etiological agent of infectious endocarditis as well as skin and soft tissue infections, and is one of the four leading causes of food-borne illness. Altogether, *S. aureus* infects more than 1.2 million patients per year in U.S. hospitals. The threat of *S. aureus* to human health is further highlighted by the emergence of antibiotic-resistant strains (i.e., methicillin-resistant *S. aureus* (MRSA) strains), including strains that are resistant to vancomycin, an antibiotic considered the last line of defense against *S. aureus* infection. These facts highlight the importance of developing novel therapeutics against this important pathogen.

*S. aureus* produces a diverse array of virulence factors and toxins that enable this bacterium to neutralize and withstand attack by different kinds of immune cells, specifically subpopulations of white blood cells that make up the body's primary defense system. The production of these virulence factors and toxins allow *S. aureus* to maintain an infectious state (Nizet, "Understanding How Leading Bacterial Pathogens Subvert Innate Immunity to Reveal Novel Therapeutic Targets," *J. Allergy Clin. Immunol.* 120(1):13 22 (2007)). Among these virulence factors, *S. aureus* produces several bi-component leukotoxins, which damage membranes of host defense cells and erythrocytes by the synergistic action of two non-associated proteins or subunits (see Menestrina et al., "Mode of Action of Beta-Barrel Pore-Forming Toxins of the *Staphylococcal* Alpha-Hemolysin Family," *Toxicol.* 39(11):1661-1672 (2001)). Among these bi-component leukotoxins, gamma-hemolysin (HlgAB and HlgCB) and the Pantone-Valentine Leukocidin (PVL) are the best characterized.

The toxicity of the leukocidins towards mammalian cells involves the action of two components. The first subunit is named class S-subunit (i.e., "slow-eluted"), and the second subunit is named class F-subunit (i.e., "fast-eluted"). The S- and F-subunits act synergistically to form pores on white blood cells including monocytes, macrophages, dendritic cells and neutrophils (collectively known as phagocytes) (Menestrina et al., "Mode of Action of Beta-Barrel Pore-Forming Toxins of the *Staphylococcal* Alpha-Hemolysin Family," *Toxicol.* 39(11):1661 1672 (2001)). The mechanism by which the bi-component toxins form pores in target cell membranes is not entirely understood. The proposed mechanism of action of these toxins involves binding of the S-subunit to the target cell membrane, most likely through a receptor, followed by binding of the F-subunit to the S-subunit, thereby forming an oligomer which in turn forms a pre-pore that inserts into the target cell membrane (Jayasinghe et al., "The Leukocidin Pore: Evidence for an Octamer With Four LukF Subunits and Four LukS Subunits Alternating Around a Central Axis," *Protein. Sci.* 14(10):2550 2561 (2005)). The pores formed by the bi-component leukotoxins are typically cation-selective. Pore formation causes cell death via lysis, which in the cases of the target white blood cells, has been reported to result from an osmotic imbalance due to the influx of cations (Miles et al., "The *Staphylococcal* Leukocidin Bicomponent Toxin Forms Large Ionic Channels," *Biochemistry* 40(29):8514 8522 (2001)).

Designing effective therapy to treat MRSA infection has been especially challenging. In addition to the resistance to methicillin and related antibiotics, MRSA has also been found to have significant levels of resistance to macrolides (e.g., erythromycin), beta-lactamase inhibitor combinations (e.g., Unasyn, Augmentin) and fluoroquinolones (e.g. ciprofloxacin), as well as to clindamycin, trimethoprim/sulfamethoxisol (Bactrim), and rifampin. In the case of serious *S. aureus* infection, clinicians have resorted to intravenous vancomycin. However, as noted above there have been reports of *S. aureus* resistance to vancomycin. Thus, there is a need to develop new antibiotic drugs that effectively combat *S. aureus* infection.

The present invention is directed to overcoming these and other limitations in the art.

SUMMARY OF THE INVENTION

A first aspect of the present invention is directed to a method of preventing or treating *Staphylococcus aureus* infection and/or a condition resulting from a *S. aureus* infection in a subject. This method involves selecting a subject at risk of having or having *S. aureus* infection and administering a CD11b inhibitor to the selected subject under conditions effective to prevent or treat *S. aureus* infection and/or a condition resulting from a *S. aureus* infection in the subject.

Another aspect of the present invention relates to a transgenic non-human animal whose genome comprises a stably integrated expression construct that comprises a polynucleotide sequence encoding human CD11b. Other aspects of the present invention relate to methods of identifying candidate compounds suitable for preventing or treating *S. aureus* infection and/or conditions resulting from a *S. aureus* infection using the transgenic non-human animal of the present invention.

Another aspect of the present invention relates to a method of identifying compounds capable of preventing or treating *S. aureus* infection and/or a condition resulting from a *S. aureus* infection. This method involves providing a collection of candidate compounds and providing a population of cells expressing human CD11b. The method further involves treating the population of cells with an agent capable of inducing LukAB mediated cytotoxicity, and contacting the population of treated cells with one or more candidate compounds from the collection. The method further involves measuring LukAB mediated cytotoxicity level in the population of treated cells in the presence and absence of the one or more candidate compounds and comparing the measured level of LukAB mediated cytotoxicity in the presence and in the absence of the one or more candidate compound. A decrease in the level of LukAB mediated cytotoxicity in the presence of the one or more candidate compounds compared to in its absence of the one or more candidate compounds identifies a compound capable of preventing or treating S. aureus infection and/or a condition resulting from a S. aureus infection.

Another aspect of the present invention relates to a method of identifying candidate compounds capable of preventing or treating S. aureus infection and/or a condition resulting from a S. aureus infection. This method involves providing a collection of candidate compounds and providing an isolated CD11b receptor or a fragment thereof comprising a LukAB binding domain. The method further involves treating the isolated CD11b receptor or the fragment thereof with an agent comprising a labeled LukA, LukB, and/or labeled LukAB protein and contacting the treated, isolated CD11b receptor or the fragment thereof with one or more candidate compounds from the collection. The binding level of the labeled LukA, LukB, and/or labeled LukAB to the isolated CD11b receptor or fragment thereof is measured in the presence and in the absence of one or more candidate compounds, and the level of LukA, LukB, and/or LukAB binding to the isolated CD11b receptor or fragment thereof in the presence and absence of the one or more candidate compounds is compared. One or more candidate compounds that are capable of preventing or treating S. aureus infection and/or a condition resulting from a S. aureus infection are identified based on this comparison.

S. aureus infects more than 1.2 million patients per year in USA hospitals, with around 40,000 deaths per year in the USA. This bacterium is the leading cause of nosocomial and community acquired infections; is the most common etiological agent of infectious endocarditis, skin, and soft tissue infections; and is one of the four leading causes of foodborne illness. The threat of S. aureus to human health is further compounded by the emergence of antibiotic-resistant strains, including methicillin-resistant S. aureus (MRSA). These facts highlight the importance of identifying new targets for the development of novel therapeutics. The present invention relates to the discovery that CD11b is the human cellular receptor for the S. aureus virulence factor leukotoxin AB (LukAB). LukAB is responsible for the cytotoxic properties of both methicillin sensitive and methicillin resistant S. aureus towards human neutrophils, and identification of its cellular receptor on human cells enables a new therapeutic approach to protect against S. aureus infection. In addition, discovery of this virulence receptor allows for the generation of improved animal models and screening assays for studying S. aureus infection and identifying novel therapeutics.

BRIEF DESCRIPTION OF THE DRAWINGS

FIG. 1A is a graph of human polymorphonuclear leukocyte (PMN) viability upon intoxication with secreted proteins isolated from isogenic wildtype (WT) and ΔlukAB mutant MSSA and MRSA strains. The increased viability observed in cells treated with secreted proteins from ΔlukAB mutant strains was reversed by expressing lukAB in trans with a plasmid (ΔlukAB/plukAB). Host cell viability was monitored with CellTiter, a reagent that monitors cellular metabolic activity. FIG. 1B is a graph showing S. aureus survival in human whole blood and primary human PMNs. Colony forming units were normalized to input CFU. FIG. 1C is a graph showing bacterial burden in kidneys of mice infected with indicated strains 96-hrs post-infection. Results represent the average of PMNs/whole blood from more than 6 different donors (FIGS. 1A and 1B) and 20 mice per group (FIG. 1C)±S.E.M. * denote statistically significant difference compared to WT (ANOVA $p<0.05$).

FIG. 4A is a pull-down of biotinylated PMN-HL60 lysates with his-tagged LukAB using Ni-NTA beads, where samples were transferred to a nitrocellulose membrane and probed with DyLight streptavidin. FIG. 4B is an immunoblot of a pull-down of PMN-HL60 lysates with his-tagged leukotoxins as described above using an anti-CD11b antibody. FIG. 4C is a Sypro Ruby protein stain of a pull-down of purified Mac-1 with his-tagged leukotoxins as described above, and FIG. 4D shows the corresponding immunoblot with an anti-CD11b antibody.

FIG. 5A is a bar graph showing cell viability after intoxication of HL60 or PMN-HL60 cells with 10 μg/ml of LukAB for 1 hour. Cell viability was measured with the metabolic dye CellTiter. FIG. 5B is a flow cytometry plot of CD18 and CD11b surface levels in PMN-HL60 cells transduced with a CD18 shRNA virus compared to a non-targeting (NT) shRNA virus. FIG. 5C is a bar graph quantifying pore formation with intoxication of the NT and CD18 shRNA PMN-HL60 cells with 10 μg/ml of LukAB or PVL for 1 hr. Pore formation was measured with the fluorescent dye Ethidium bromide (EtBr). FIG. 5D shows CD18 and CD11b surface levels in HL60 cells and PMN-HL60 cells transduced with a with a CD11b shRNA virus or a non-targeting (NT) shRNA virus measured as described for FIG. 5B. FIG. 5E is a bar graph quantifying pore formation with intoxication of the NT and CD11b shRNA PMN-HL60 cells with 10 μg/ml of LukAB or PVL for 1 hour. Pore formation was measured with EtBr. FIG. 5F shows intoxication of CD11b transfected 293T cells with 40 μg/ml of LukAB or PVL for 2 hours. Percent depletion of CD11b[+] cells was determined by staining cells with an anti-CD11b antibody post intoxication and performing flow cytometry analysis. The bar graph of FIG. 5F depicts the average of two independent experiments. FACS plots are from a representative experiment. All other data is represented as the average of triplicate samples±standard deviation (SD) unless otherwise indicated. *** indicates $P<0.0001$ by one way analysis of variance.

FIG. 7A is a bar graph showing the viability of PMNs treated with 10 μg/ml of integrin-specific antibodies (α-CD11a, α-CD11c, and α-CD18), including three different anti-CD11b clones (α-CD11b), or no antibody (No Ab) followed by a 1-hour intoxication with 2.5 μg/ml of LukAB. Membrane damage was measured with the fluorescent dye SYTOX green. Results represent the mean from PMNs isolated from 8 donors±SEM. FIG. 7B shows the viability of PMNs treated with 10 μg/ml of LM2/1 or an isotype control then intoxicated and evaluated as described above. Results represent the mean from PMNs isolated from 4 donors±SEM. FIG. 7C shows CD11b surface levels on HL60 cells stably transduced with empty vector (EV), WT CD11b, or I-less CD11b virus compared to PMN-HL60s as determined by flow cytometry analysis with an anti-CD11b antibody. Viability of stably transduced HL60 cell lines described in FIG. 7C compared to PMN-HL60s after 1-hour intoxication with 10 μg/ml of LukAB where membrane damage (FIG. 7D) and cellular metabolism (FIG. 7E) were evaluated as described in FIG. 7A and FIG. 5A respectively. Data is represented as the average of triplicate samples±SD. * indicates $P<0.05$,  indicates $P<0.01$, and * indicates $P<0.0001$ by one way analysis of variance.

FIG. 8A is a bar graph showing pore formation in peritoneal exudate cells (PECs) following a 1-hour intoxication with 20 μg/ml of LukAB or 10 μg/ml of LukED as measured with EtBr. Data is represented as the average of triplicate samples±SD. FIG. 8B is a flow cytometry analysis showing Ly6G and CD11b surface levels on PECs using anti-Ly6G and anti-CD11b antibodies. FIG. 8C is a phylogenetic tree of the amino acid sequence alignment of human, gorilla, rabbit and mouse I-domains constructed with DNASTAR MegAline software using the CLUSTALW method. FIG. 8D shows results of a competition dot blot assay where purified recombinant human CD11b I-domain was incubated with 5 μg/ml fluorescently labeled LukAB (FITC-LukAB) and 10-fold excess (50 μg/ml) of unlabeled LukAB or unlabeled PVL. FITC-LukAB binding was quantified by densitometry. FIG. 8E is a dot blot of purified recombinant human or murine CD11b I-domain incubated with 5 μg/ml FITC-LukAB. FITC-LukAB binding was quantified by densitometry.

FIG. 9A is a graph showing viability of the non-target (NT) or CD11b shRNA PMN-HL60 cells described in FIG. 5B following a 2-hour infection with non-opsonized wild type (WT) CA-MRSA USA300 or an isogenic lukAB mutant (ΔlukAB) at the indicated multiplicity of infection (MOI). Membrane damage was measured with SYTOX green. Data is represented as the average of triplicate samples±SD. FIG. 9B is a graph showing viability of PMNs treated with 10 μg/ml of CD11b-specific antibodies (three different clones) followed by a 1 hour infection with the indicated MOI of non-opsonized WT USA300. Membrane damage was measured with SYTOX green. Results represent the mean from PMNs isolated from 8 donors±SEM. * indicates $P<0.05$, and *** indicates $P<0.0001$ by one way analysis of variance.

FIG. 11A is a graph showing viability of non-target (NT) or CD11b shRNA PMN-HL60 cells described in FIG. 5D following a 90 minute infection with various MOI of opsonized WT or ΔlukAB USA300. Membrane damage was measured with SYTOX green. Data is represented as the average of triplicate samples±SD. FIG. 11B is a graph showing the growth of opsonized WT or ΔlukAB USA300 upon infection of NT or CD11b shRNA PMN-HL60 cells at a MOI of 10. Bacterial colony forming units were determined by dilution plating after lysing the PMN-HL60 cells at 1, 2, or 3 hours post synchronization. To determine % growth, bacterial counts were normalized to input at time 0, which was set at 100%. Results represent the average of triplicate samples from 2 independent infections±SD. The photomicrographs of FIG. 11C show localization of CD11b in PMNs post-infection with opsonized GFP-USA300 at a MOI of 10 or in uninfected PMNs determined by staining with a fluorescently conjugated anti-CD11b antibody or an isotype control prior to infection. Cells were fixed post-synchronization and images were captured using an Applied Precision PersonalDV live-cell imaging system. A representative image for each condition is shown. FIG. 11D shows infection of PMNs pre-treated with the LM2/1 anti-CD11b antibody or an isotype control with GFP-USA300 at a MOI of 10. EtBr staining in red is indicative of pore formation. Images were captured using a fluorescent microscope at 0 and 30 minutes post-synchronization and representative images from 30 minutes are shown. FIG. 11E is a graph showing quantification of ethidium bromide positive PMNs per field of view obtained from images shown in FIG. 11D. Results represent the average of three independent counts from infections of PMNs isolated from two donors at (T0) and 30 (T30) minutes post-infection.  indicates $P<0.001$ and * indicates $P<0.0001$ by one way analysis of variance.

DETAILED DESCRIPTION OF THE INVENTION

Figures 1A, 1B, 1C:
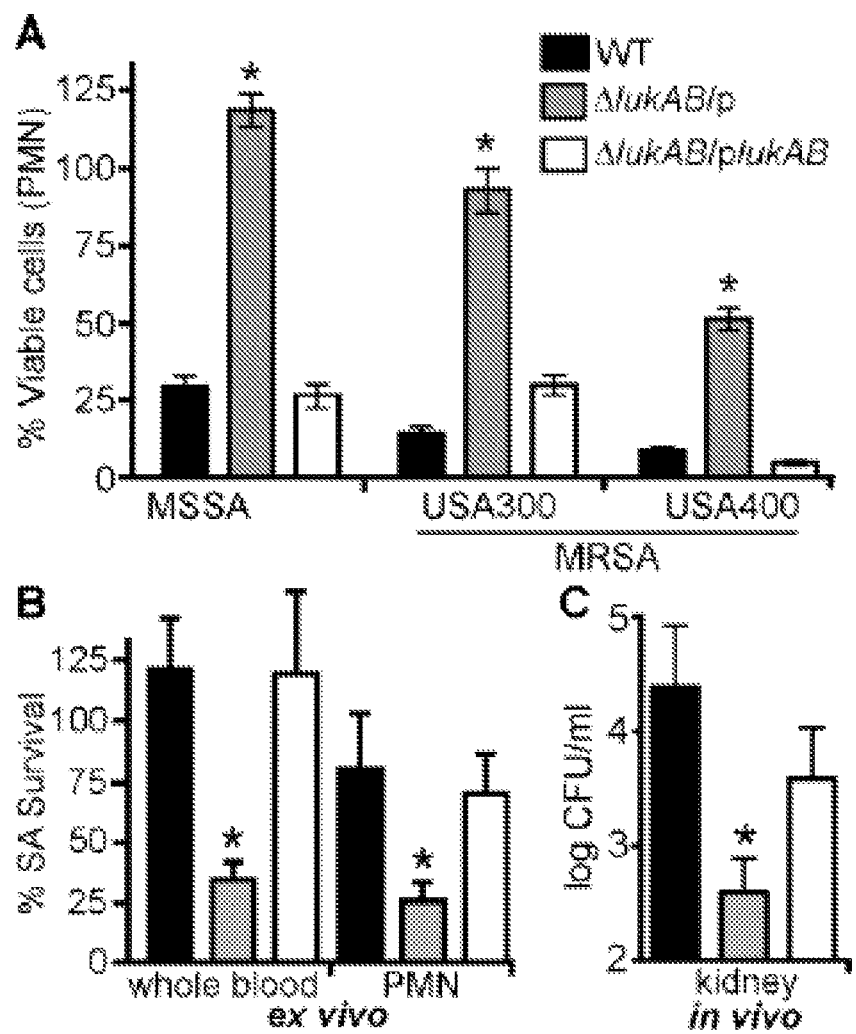
FIGS. 1A-1C show LukAB and S. aureus cytotoxicity.

A first aspect of the present invention is directed to a method of preventing or treating *Staphylococcus aureus* infection and/or a condition resulting from a *S. aureus* infection in a subject. This method involves selecting a subject at risk of having or having *S. aureus* infection and administering a CD11b inhibitor to the selected subject under conditions effective to prevent or treat *S. aureus* infection and/or a condition resulting from a *S. aureus* infection in the subject To date, the majority of *S. aureus* infections are due to MRSA (Moran et al., "Methicillin-Resistant *S. aureus* Infections Among Patients in the Emergency Department," *The New England Journal of Medicine* 355:666-674 (2006), which is hereby incorporated by reference in its entirety). Previously, the majority of MRSA infections were thought to be of nosocomial origin (HA-MRSA), however infections are now occurring in otherwise healthy individuals who have not had exposure to healthcare facilities, i.e., community-associated MRSA (CA-MRSA) (Klevens et al., "Invasive Methicillin-Resistant *Staphylococcus aureus* Infections in the United States," *Jama* 298:1763-1771 (2007) and Klevens et al., "Changes in the Epidemiology of Methicillin-Resistant *Staphylococcus aureus* in Intensive Care Units in US Hospitals, 1992-2003," *Clin. Infect. Dis.* 42:389-391 (2006), which are hereby incorporated by reference in their entirety). These CA-MRSA associated infections are more severe and result in higher mortality rates compared to HA-MRSA infections (Deleo et al., "Community-Associated Methicillin-Resistant *Staphylococcus aureus*," *Lancet* 375:1557-1568 (2010), which is hereby incorporated by reference in its entirety). Recent reports have suggested that the increased virulence of strains associated with CA-MRSA infections compared to those associated with HA-MRSA infections is primarily due to the enhanced ability of CA-MRSA-associated strains to evade neutrophil (PMNs)-mediated killing (Voyich et al., "Insights into Mechanisms Used by *Staphylococcus aureus* to Avoid Destruction by Human Neutrophils," *J. Immunol.* 175:3907-3919 (2005); Wang et al., "Identification of Novel Cytolytic Peptides as Key Virulence Determinants for Community-Associated MRSA," *Nat. Med.* 13:1510-1514 (2007); Li et al., "Evolution of Virulence in Epidemic Community-Associated Methicillin-Resistant *Staphylococcus aureus*," *Proc. Nat'l Acad. Sci. U.S.A.* 106:5883-5888 (2009); Dumont et al., "Characterization of a New Cytotoxin That Contributes to *Staphylococcus aureus* Pathogenesis," *Mol. Microbiol.* 79:814-825 (2011); and Alonzo III et al., "*Staphylococcus aureus* Leucocidin ED Contributes to Systemic Infection by Targeting Neutrophils and Promoting Bacterial Growth in Vivo," *Mol. Microbiol.* 83:423-435 (2012), which are hereby incorporated by reference in their entirety). *S. aureus* avoids PMN-mediated killing by targeting and killing PMNs with a collection of cytotoxins and cytolytic peptides (Wang et al., "Identification of Novel Cytolytic Peptides as Key Virulence Determinants for Community-Associated MRSA," *Nat. Med.* 13:1510-1514 (2007); Dumont et al., "Characterization of a New Cytotoxin That Contributes to *Staphylococcus aureus* Pathogenesis," *Mol. Microbiol.* 79:814-825 (2011); Alonzo III et al., "*Staphylococcus aureus* Leucocidin ED Contributes to Systemic Infection by Targeting Neutrophils and Promoting Bacterial Growth in Vivo," *Mol. Microbiol.* 83:423-435 (2012); Loffler et al., "*Staphylococcus aureus* Panton-Valentine Leukocidin is a Very Potent Cytotoxic Factor for Human Neutrophils," *PLoS Pathog.* 6:e1000715 (2010); and Ventura et al., "Identification of a Novel *Staphylococcus aureus* Two-Component Leukotoxin Using Cell Surface Proteomics," *PLoS One* 5:e11634 (2010), which are hereby incorporated by reference in their entirety). In this regard, *S. aureus* strains associated with human infections can produce up to four different bi-component leukotoxins. These bi-component leukotoxins are members of the β-barrel pore-forming family of toxins that exhibit marked selectivity towards host phagocytes. The cytotoxic properties of the *staphylococcal* leukotoxins have been attributed to the formation of octameric pores in target cell membranes in vitro, which result in cell swelling, ultimately leading to cell death (Ferreras et al., "The Interaction of *Staphylococcus aureus* Bi-Component Gamma-Hemolysins and Leucocidins With Cells and Lipid Membranes," *Biochim. Biophys. Acta* 1414:108-126 (1998); Jayasinghe & Bayley, "The Leukocidin Pore: Evidence for an Octamer With Four LukF Subunits and Four LukS Subunits Alternating Around a Central Axis," *Protein Sci.* 14:2550-2561 (2005); Sugawara-Tomita et al., "Stochastic Assembly of Two-Component *Staphylococcal* Gamma-Hemolysin into Heteroheptameric Transmembrane Pores With Alternate Subunit Arrangements in Ratios of 3:4 and 4:3," *J. Bacteriol.* 184:4747-4756 (2002); Menestrina et al., "Mode of Action of Beta-Barrel Pore-Forming Toxins of the *Staphylococcal* Alpha-Hemolysin Family," *Toxicon* 39:1661-1672 (2001), which are hereby incorporated by reference in their entirety). Among the four different bicomponent leukotoxins, Leukotoxin AB (LukAB) is primarily responsible for the cytotoxic properties of both MSSA and MRSA respectively, towards human neutrophils (see Examples infra and U.S. Patent Publication No. 2011/0274693 to Torres, which is hereby incorporated by reference in its entirety).

Given the large number of individual who contract MRSA annually, it is likely that a substantial proportion of these infections will be refractory to traditional courses of antibiotic treatment. An innovative approach to treat such infections is to inhibit *S. aureus* virulence factors, such as LukAB, which are responsible for killing PMNs, the most critical innate immune cell involved in defense against *S. aureus* infection. As described herein, applicants have identified CD11b as the cellular receptor for LukAB on human PMNs. Binding of LukAB to CD11b is the first step in LukAB cytotoxicity, which is followed by LukAB oligomerization and pore formation leading to cell death. Therefore, agents which inhibit the LukAB/CD11b interaction, such as CD11b inhibitors, are clinically useful for blocking LukAB cytotoxicity, in turn preventing depletion of PMNs, and promoting the natural clearance of *S. aureus* by the innate immune system. In a preferred embodiment of the present invention, the CD11b inhibitor selectively inhibits the CD11b/LukAB interaction without interfering with CD11b binding to its physiological ligands.

In accordance with this aspect of the present invention, suitable CD11b inhibitors include, without limitation, protein or peptide inhibitors, antibodies, and small molecules, many of which are known in the art as described below.

An exemplary peptide inhibitor of CD11b comprises a recombinant Neutrophil Inhibitory Factor (rNIF), also known as UK-279276. NIF is a 41-kDa glycoprotein isolated and cloned from the canine hookworm *Ancylostoma caninum* (Moyle et al., "A Hookworm Glycoprotein That Inhibits Neutrophil Function is a Ligand for the Integrin CD11b/CD18," *J. Biol. Chem.* 209(13):10008-10015(1994), which is hereby incorporated by reference in its entirety). NIF binds with high affinity to the CD11b/CD18 receptor complex (also known as Mac-1, Mo1, αMβ2, and CR3), thereby blocking CD11b/CD18 receptor binding to its physiological ligand on endothelial cells. In accordance with the present invention, therapeutic compositions comprising rNIF (UK-279276) will readily inhibit LukAB interaction with CD11b and prevent its subsequently induced cytotoxicity.

Another exemplary protein or peptide inhibitor suitable for use in the methods of the present invention is a recombinant soluble protein comprising the LukAB receptor binding domain. In a preferred embodiment of this aspect of the invention, the soluble protein comprises a recombinant human CD11b protein or a CD11b LukAB binding domain. An exemplary soluble protein comprising the LukAB binding domain is a soluble protein comprising the I-domain of CD11b or a fragment thereof. The I-domain of CD11b spans amino acid residues 147-337 of SEQ ID NO: 2 (NCBI Accession No. NP_000632) and residues 147-337 of SEQ ID NO: 4 (NCBI Accession No. NP_001139280). Another exemplary soluble protein comprising a CD11b protein is the soluble human CD11b/CD18 receptor described by Dana et al., "Expression of a Soluble and Functional Form of the Human β2 Integrin CD11b/CD18," *Proc. Natl. Acad. Sci. USA* 88:3106-3110 (1991), which is hereby incorporated by reference in its entirety. In accordance with this aspect of the present invention, therapeutic compositions of the present invention comprising the soluble LukAB receptor binding protein will bind the *S. aureus* LukAB virulence factor, preventing its interaction with CD11b expressing target cells (e.g. phagocytes) and its subsequently induced cytotoxicity.

In another embodiment of this aspect of the invention, the CD11b inhibitor is a CD11b or CD11b/CD18 specific antibody. As used herein, the term "antibody" is meant to include intact immunoglobulins derived from natural sources or from recombinant sources, as well as immunoreactive portions (i.e. antigen binding portions) of intact immunoglobulins. Antibodies of the present invention include monoclonal antibodies, polyclonal antibodies, antibody fragments, diabodies, tribodies, pentabodies, nanobodies, genetically engineered forms of the antibodies, and combinations thereof. Suitable antibodies includes full length (i.e., naturally occurring or formed by normal immunoglobulin gene fragment recombinatorial processes) immunoglobulin molecules (e.g., an IgG antibody) and immunologically active fragments thereof (i.e., including the specific binding portion of the full-length immunoglobulin molecule), which again may be naturally occurring or synthetic in nature. Accordingly, the term "antibody fragment" includes a portion of an antibody such as F(ab')$_2$, F(ab)$_2$, Fab', Fab, Fv, scFv and the like. Regardless of structure, an antibody fragment binds with the same antigen that is recognized by the full-length antibody, and, in the context of the present invention, specifically binds CD11b or CD11b/CD18 and prevents LukAB binding. In a preferred embodiment, an antibody of the present invention, binds to the LukAB binding domain of CD11b, i.e., the I-domain of CD11b, but does not bind to other domains of CD11b so as to allow other physiological ligands of the CD11b/CD18 receptor to bind to the receptor while specifically blocking *S. aureus* LukAB binding. Methods of making and screening antibodies and antibody fragments are well-known in the art.

Monoclonal antibodies of the present invention may be derived from any mammalian animal, for example, and without limitation, a rodent, rabbit, dog, goat, horse, camel, llama, chicken, human.

Methods for monoclonal antibody production may be carried out using techniques well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., Cd11b or fragment thereof) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In another embodiment of the present invention, monoclonal CD11b antibodies or antibody fragments can be isolated from antibody phage libraries generated using the techniques described in McCafferty et al., "Phage Antibodies: Filamentous Phage Displaying Antibody Variable Domains," *Nature* 348:552-554 (1990), which is hereby incorporated by reference in its entirety. Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., *BioTechnology* 10:779-783 (1992), which is hereby incorporated by reference in its entirety), as well as combinatorial infection and in vivo recombination as a strategy for constructing very large phage libraries (Waterhouse et al., *Nuc. Acids. Res.* 21:2265-2266 (1993), which is hereby incorporated by reference in its entirety). Thus, these techniques are viable alternatives to traditional monoclonal antibody hybridoma techniques for isolation of monoclonal antibodies.

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate monoclonal antibodies.

The CD11b antibody can also be a humanized or chimeric antibody. "Humanized" forms of non-human (e.g., rodent) antibodies are chimeric antibodies that contain minimal sequences derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992), which are hereby incorporated by reference in their entirety.

Chimeric antibodies preferably have constant regions derived substantially or exclusively from human antibody constant regions and variable regions derived substantially or exclusively from the sequence of the variable region from a mammal other than a human. The chimerization process can be made more effective by also replacing the variable regions—other than the hyper-variable regions or the CDRs, of a murine (or other non-human mammalian) antibody with the corresponding human sequences. The variable regions other than the CDRs are also known as the variable framework regions (FRs). Yet other monoclonal antibodies of the present invention are bi-specific, in that they have specificity for both LukA and/or LukB and CD11b. Bispecific antibodies are preferably human or humanized.

As described in the Examples herein, CD11b specific antibodies are known in the art (see also Dana et al., "Two Functional Domains in the Phagocyte Membrane Glycoprotein Mo1 Identified with Monoclonal Antibodies," *J. Immunol.* 137: 3259-3263 (1986) and Jaeschke et al., "Functional Inactivation of Neutrophils with Mac-1 (CD11b/CD18) Monoclonal Antibody Protects Against Ischemia-Reperfusion Injury in Rat Liver," Hepatology 17(5) 915-923 (1993), which are hereby incorporated by reference in their entirety). A particularly suitable antibody is the murine LM2/1 CD11b antibody (Santa Cruz) that binds the human I-domain of CD11b. Similar antibodies, i.e., human or humanized antibodies, have the same antigen binding domain as the LM2/1 CD11b antibody are also suitable for use in the methods of the present invention. A number of other human CD11b and CD11b/CD18 antibodies are also commercially available, see e.g., anti-CR3 (CD11b/CD18) antibodies and 2LPM19c (anti-CD11b antibody) from DAKO (Carpinteria, Calif.) and αM-44 antibody (CD11b) from Santa Cruz Biotechnology (Santa Cruz, Calif.).

In another embodiment of this aspect of the present invention, a suitable CD11b inhibitor is a small molecule inhibitor. Suitable small molecule CD11b inhibitors are known in the art and include 2-[4-(3,4-dihydro-2H-quinolin-1-yl)-buta-1,3-dienyl]-1-thylnaptho[1,2-d]thiazol-1-ium; chloride (Compound 1) and derivative thereof, and 1-ethyl-2-/3-/1-ethylbenzothiazolin-2-ylidiene/propenyl/-thiazolium; iodide (Compound 2) and derivatives thereof (Bansal et al., "Small Molecule Antagonists of Complement Receptor Type 3 Bock Adhesion and Adhesion-Dependent Oxidative Burst in Human Polymorphonuclear Leukocytes," *J. Pharm. Exp. Therap.* 304(3):1016-1024 (2003), which is hereby incorporated by reference in its entirety). Suitable derivatives of these small molecule inhibitors (i.e., Compounds 1 and 2) include any derivative compounds that maintain the ability to block ligand binding to the CD11b/CD18 receptor complex, measured using an in vitro ligand binding assay or cellular adhesion assay. Exemplary derivative small molecule inhibitors that are also suitable for use in the methods of the present invention are described by Bansal et al., "Small Molecule Antagonists of Complement Receptor Type 3 Bock Adhesion and Adhesion-Dependent Oxidative Burst in Human Polymorphonuclear Leukocytes," *J. Pharm. Exp. Therap.* 304(3):1016-1024 (2003), which is hereby incorporated by reference in its entirety.

Another small molecule inhibitor of CD11b that is suitable for use in the methods of the present invention comprises N-[9H-(2,7-dimethylfluorenyl-9-methoxy)carbonyl]-L-leucine (NPC 15669) (see Bator et al., "N-[9H-(2,7-dimethylfluorenyl-9-methoxy)carbonyl]-L-leucine, NPC 15669, Prevents Neutrophil Adherence to Endothelium and Inhibits CD11b/CD18 Upregulation," *Immunopharmacology* 23(2):139-49 (1992), which is hereby incorporated by reference in its entirety).

A suitable subject for treatment in accordance with the methods of the present invention includes, without limitation, any animal, preferably, a mammal, more preferably a human. Suitable subjects include both immunocompromised and non-immunocompromised infants, juveniles, and adults. In one embodiment of the present invention the subject has or is at risk of having a methicillin-resistant *S. aureus* (MRSA) infection. In another embodiment of the present invention, the subject has or is at risk of having a methicillin sensitive *S. aureus* (MSSA) infection. Other suitable subjects include those subjects which may have or are at risk for developing a condition resulting from a *S. aureus* infection, i.e., a *S. aureus* associated condition, such as, for example, skin wounds and infections, tissue abscesses, folliculitis, osteomyelitis, pneumonia, scalded skin syndrome, septicemia, septic arthritis, myocarditis, endocarditis, and toxic shock syndrome.

In one embodiment of the present invention, the CD11b inhibitor is administered prophylactically to prevent, delay, or inhibit the development of *S. aureus* infection in a subject at risk of getting a *S. aureus* infection or associated condition. In some embodiments of the present invention, prophylactic administration of a CD11b inhibitor is effective to fully prevent *S. aureus* infection in an individual. In other embodiments, prophylactic administration is effective to prevent the full extent of infection that would otherwise develop in the absence of such administration, i.e., substantially prevent or inhibit *S. aureus* infection in an individual.

In another embodiment of the present invention, the CD11b inhibitor is administered therapeutically to an individual having a *S. aureus* infection to inhibit further development of the infection, i.e., to inhibit the spread of the infection to other cells in an individual.

The therapeutic compositions of the present invention can be administered as part of a combination therapy in conjunction with another active agent, depending upon the nature of the *S. aureus* infection that is being treated. Such additional active agents include anti-infective agents, antibiotic agents, and antimicrobial agents.

Representative anti-infective agents that may be useful in the present invention include vancomycin and lysostaphin. Other anti-infective agents include a LukAB inhibitor as described in U.S. Patent Application Publication No. 2011/0274693 to Torres et al., which is hereby incorporated by reference in its entirety; a LukED inhibitor or antibody as described in U.S. Patent Publication No. 2013/0017203 to Torres et al., which is hereby incorporated by reference in its entirety; and a CCR5 inhibitor 2013/0039885 to Torres et al., which is hereby incorporated by reference in its entirety.

Representative antibiotic agents and antimicrobial agents that may be useful in the present invention include penicillinase-resistant penicillins, cephalosporins and carbapenems, including vancomycin, lysostaphin, penicillin G, ampicillin, oxacillin, nafcillin, cloxacillin, dicloxacillin, cephalothin, cefazolin, cephalexin, cephradine, cefamandole, cefoxitin, imipenem, meropenem, gentamycin, teicoplanin, lincomycin and clindamycin. Dosages of these antibiotics are well known in the art (see, e.g., MERCK MANUAL OF DIAGNOSIS AND THERAPY (Beers & Berkow eds., 2004), which is hereby incorporated by reference in its entirety). The anti-infective, antibiotic and/or antimicrobial agents may be combined prior to administration, or administered concurrently (as part of the same composition or by way of a different composition) or sequentially with the CD11b inhibitor compositions of the present invention. In certain embodiments, the administering is repeated.

Therapeutic compositions of the present invention may be administered in a single dose, or in accordance with a multi-dosing protocol. For example, in one embodiment of the present invention, relatively few doses of the therapeutic composition are administered, such as one or two doses. In another embodiment of the present invention, the therapeutic composition is administered more frequently, e.g., daily until the level of infection decreases or is gone. In embodiments that include conventional antibiotic therapy, which generally involves multiple doses over a period of days or weeks, the antibiotics can be taken one, two or three or more times daily for a period of time, such as for at least 5 days, 10 days or even 14 or more days, while the CD11b inhibitor composition is administered only once or twice. However, the different dosages, timing of dosages, and relative amounts of the therapeutic composition and antibiotics can and should be selected and adjusted by one of ordinary skill in the art based on the subject and infection being treated.

In the context of using CD11b inhibitory compositions of the present invention to prevent a S. aureus infection, the concentration of the inhibitory CD11b compositions must be adequate to achieve the prevention or substantial prevention of S. aureus infection, particularly the prevention of S. aureus in susceptible populations (i.e., an infant, juvenile, adult, or an immunocompromised infant, juvenile, or adult). In the context of using therapeutic compositions to treat a S. aureus infection, the dosage of a CD11b inhibitory composition is one that is adequate to inhibit LukAB mediated cytotoxicity and is capable of achieving a reduction in a number of symptoms, a decrease in the severity of at least one symptom, or a delay in the further progression of at least one symptom, or even a total alleviation of the infection.

A therapeutically effective amount of a CD11b inhibitor for inhibiting LukAB mediated cytotoxicity can be determined in accordance with standard procedures, which take numerous factors into account, including, for example, the concentrations of these active agents in the composition, the mode and frequency of administration, the severity of the S. aureus infection to be treated (or prevented), and subject details, such as age, weight and overall health and immune condition. General guidance can be found, for example, in REMINGTON'S PHARMACEUTICAL SCIENCES (Mack Publishing Company 1990), which is hereby incorporated by reference in its entirety. A clinician may administer a CD11b inhibitory composition, until a dosage is reached that provides the desired or required prophylactic or therapeutic effect. The progress of this therapy can be easily monitored by conventional assays.

The agents of the present invention can be administered by parenteral, topical, intravenous, oral, subcutaneous, intraperitoneal, intranasal or intramuscular means for prophylactic and/or therapeutic treatment.

The pharmaceutical agents of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the pharmaceutical agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Another aspect of the present invention relates to a transgenic non-human animal whose genome comprises a stably integrated expression construct that comprises a polynucleotide sequence encoding human CD11b.

Suitable nucleotide sequences encoding human CD11b are known in the art and are shown below as SEQ ID NO: 1 (NCBI Accession No. NM_000632) and SEQ ID NO: 3 (NCBI Accession No. NM_001145808). The corresponding CD11b amino acid sequences are also shown below as SEQ ID NO: 2 (NCBI Accession No. NP_000632) and SEQ ID NO: 4 (NM_00001139280), respectively.

SEQ ID NO: 1

```
tggcttcctt gtggttcctc agtggtgcct gcaaccnctg gttcacctcc ttccaggttc   60
tggctccttc cagccatggc tctcagagtc cttctgttaa cagccttgac cttatgtcat  120
gggttcaact tggacactga aaacgcaatg accttccaag agaacgcaag gggcttcggg  180
cagagcgtgg tccagcttca gggatccagg gtggtggttg gagcccccca ggagatagtg  240
gctgccaacc aaaggggcag cctctaccag tgcgactaca gcacaggctc atgcgagccc  300
atccgcctgc aggtccccgt ggaggccgtg aacatgtccc tgggcctgtc cctggcagcc  360
accaccagcc cccctcagct gctggcctgt ggtcccaccg tgcaccagac ttgcagtgag  420
aacacgtatg tgaaagggct ctgcttcctg tttggatcca acctacggca gcagcccag  480
aagttcccag aggccctccg agggtgtcct caagaggata gtgacattgc cttcttgatt  540
gatggctctg gtagcatcat cccacatgac tttcggcgga tgaaggagtt tgtctcaact  600
gtgatggagc aattaaaaaa gtccaaaacc ttgttctctt tgatgcagta ctctgaagaa  660
ttccggattc actttacctt caaagagttc cagaacaacc ctaacccaag atcactggtg  720
aagccaataa cgcagctgct tgggcggaca cacacgccaa cgggcatccg caaagtggta  780
cgagagctgt ttaacatcac caacggagcc cgaaagaatg cctttaagat cctagttgtc  840
atcacggatg gagaaaagtt tggcgatccc ttgggtatatg aggatgtcat ccctgaggca  900
gacagagagg gagtcattcg ctacgtcatt gggggtggga atgccttccg cagtgagaaa  960
tcccgccaag agcttaatac catcgcatcc aagccgcctc agtcacgt gttccaggtg 1020
aataactttg aggctctgaa gaccattcag aaccagcttc gggagaagat ctttgcgatc 1080
gagggtactc agacaggaag tagcagctcc tttgagcatg agatgtctca ggaaggcttc 1140
agcgctgcca tcacctctaa tggcccctg ctgagcactg tggggagcta tgactgggct 1200
ggtgagtct ttctatatac atcaaaggag aaaagcacct tcatcaactat gaccagagtg 1260
gattcagaca tgaatgatgc ttacttgggt tatgctgccg ccatcatctt acggaaccgg 1320
gtgcaaagcc tggttctggg ggcacctcga tatcagcaca tcggcctggt agcgatgttc 1380
aggcagaaca ctggcatgtg ggagtccaac gctaatgtca agggcaccca gatcggcgcc 1440
tacttcgggg cctccctctg ctccgtggac gtggacagca acggcagcac cgacctggtc 1500
ctcatcgggg cccccattta ctacgagcag acccgagggg gccaggtgtc cgtgtgcccc 1560
ttgcccaggg ggagggctcg gtggcagtgt gatgctgttc tctacgggga gcagggccaa 1620
ccctggggcc gctttggggc agccctaaca gtgctggggg acgtaaatgg ggacaagctg 1680
acggacgtgg ccattgggc cccaggagag gaggacaacc ggggtgctgt ttacctgttt 1740
cacggaacct caggatctgg catcagcccc cccatagcc agcggatagc aggctccaag 1800
ctctctccca ggctccagta ttttggtcag tcactgagtg ggggccagga cctcacaatg 1860
gatgactgga tagacctgac tgtaggagcc caggggcacg tgctgctgct caggtcccag 1920
ccagtactga gagtcaaggc aatcatggag ttcaatccca gggaagtggc aaggaatgta 1980
tttgagtgta ataatcaggt ggtgaaaggc aaggaagccg gagaggtcag agtctgcctn 2040
catgtccaga agagcacacg ggatcggcta agagaaggac agatccagag tgttgtgact 2100
tatgacctgg ctctggactc cggccgccca cattcccgcg ccgtcttcaa tgagacaaag 2160
aacagcacac gcagacagac acaggtcttg gggctgaccc agcttgtga gaccctgaaa 2220
ctacagttgc cgaattgcat cgaggaccca gtgagcccca ttgtgctgcg cctgaacttc 2280
tctctggtgg gaacgccatt gtctgctttc gggaacctcc ggccagtgct ggcggaggat 2340
gctcagagac tcttcacagc cttgtttccc tttgagaaga attgtggcaa tgacaacatc 2400
tgccaggatg acctcagcat caccttcagt ttcatgagcc tggactgcct cgtggtgggt 2460
ggggccggg agttcaacgt gacagtgact gtgagaaatg atggtgagga ctcctacagg 2520
acacaggtca ccttcttctt cccgcttgac ctgtcctacc ggaaggtgtc cacactccag 2580
aaccagcgct cacagcgatc ctggcgcctg gcctgtgagt ctgcctcctc caccgaagtg 2640
tctgggccct tgaagagcac cagctgcagc ataaaccacc ccatcttccc ggaaaactca 2700
gaggtcacct taatatcac gttttgatgta gactctaagg cttcccttgg aaacaaactg 2760
ctcctcaagg ccaatgtgac cagtgagaac aacatgccca gaaccaacaa aaccgaattc 2820
caactgagc tgccggtgaa atatgctgtc tacatggtgg tcaccagcca tgggtctcc 2880
actaaatatc tcaacttcac ggcctcagag aataccagtc gggtcatgca gcatcaatat 2940
caggtcagca acctggggca gaggagcccc cccatcagcc tggtgttctt ggtgcccgtc 3000
cggctgaacc agactgtcat atgggaccgc ccccaggtca ccttctccga gaacctctcg 3060
agtacgtgcc acaccaagga gcgcttgccc tctcactccg actttctggc tgagcttcgg 3120
aaggcccccg tggtgaactg ctccatcgct gtctgccaga gaatccagtg tgacatcccg 3180
ttctttggca tccaggaaga attcaatgct accctcaagg gcaacctctc gtttgactgg 3240
tacatcaaga cctcgcataa ccacctcctg atcgtgagca cagctgagat cttgttaac 3300
gattccgtgt tcaccctgct gccgggacag gggcgtttg tgaggtccca gacggagacc 3360
aaagtggagc cgttcgaggt ccccaacccc ctgccgctca tcgtgggcag ctctgtcggg 3420
ggactgctgc tcctggccct catcaccgcc gcgctgtaca agctcggctt cttcaagcgg 3480
caatacaagg acatgatgag tgaaggggt cccccgtggg cccgaaccca gtagccggcc 3540
cttcccgaca gagctgcctc tcggtggcca gcaggactct gcccagacca cacgagcccc 3600
caggctgctg gacacgtcgg acagcgaagt atccccgaca ggacgggctt gggcttccat 3660
ttgtgtgtgt gcaagtgtgt atgtgcgtgt gtgcgagtgt gtgcaagtgt ctgtgtgcaa 3720
gtgtgtgcac gtgtgcgtgt gcgtgcatgt gcactcgcac gcccatgtgt gagtgtgtgt 3780
aagtatgtga gtgtgtccag tgtgtgtgcg tgtgtccatg tgtgtgcagt gtgtgcatgt 3840
gtgcgagtgt gtgcatgtgt gtgctcaggg gctgtggctc acgtgtgtga ctcagagtgt 3900
ctctggcgtg tgggtaggtg acggcagcgt agcctctccg gcagaaggga actgcctggg 3960
ctcccttgtg cgtggggtaag ccgctgctgg gtttctctcc agggaggggg acggtcaatc 4020
ctgtgggtga agagagaggg aaacacagca gcatctctcc actgaaagaa gtgggacttc 4080
ccgtcgcctg cgagcctgcg gcctgctgga gcctgcgcag cttggatgga tactccatga 4140
gaaaagccgt gggtggaacc aggagcctcc tccacaccag cgctgatgcc caataaagat 4200
gcccactgag gaatcatgaa gcttcctttc tggattcatt tattatttca atgtgacttt 4260
aattttttgg atggataagc ctgtctatgt tacaaaaatc acaaggcatt caagtgtaca 4320
gtgaaaagtc tcccttttcca gatattcaag tcacctcctt aaaggtagtc aagattgtgt 4380
tttgaggttt ccttcagaca gattccaggc gatgtgcaag tgtatgcacg tgtgcacaca 4440
ccacacacat acacacacac aagctttttt acacaaatgg tagcatactt tatattggtc 4500
tgtatcttgc ttttttttcac caatatttct cagacatcgg ttcatattaa gacataaatt 4560
acttttttcat tcttttatac cgctgcatag tattccattg tgtagtgta ccataatgta 4620
tttaaccagt cttcttttga tatactattt tcatctcttg ttattgcatc tgctgagtta 4680
ataaatcaaa tatatgtcaa aaaaaaaaaa aaaaaaaaa aaaaaaaaa aaaaaaaat 4740
```

SEQ ID NO: 2

```
Met Ala Leu Arg Val Leu Leu Thr Ala Leu Thr Leu Cys His Gly
1               5                  10                 15
Phe Asn Leu Asp Thr Glu Asn Ala Met Thr Phe Gln Glu Asn Ala Arg
            20                  25                  30
Gly Phe Gly Gln Ser Val Val Gln Leu Gln Gly Ser Arg Val Val
        35                  40                  45
Gly Ala Pro Gln Glu Ile Val Ala Ala Asn Gln Arg Gly Ser Leu Tyr
50                  55                  60
Gln Cys Asp Tyr Ser Thr Gly Ser Cys Glu Pro Ile Arg Leu Gln Val
65                  70                  75                  80
Pro Val Glu Ala Val Asn Met Ser Leu Gly Leu Ser Leu Ala Ala Thr
                85                  90                  95
Thr Ser Pro Pro Gln Leu Leu Ala Cys Gly Pro Thr Val His Gln Thr
            100                 105                 110
Cys Ser Glu Asn Thr Tyr Val Lys Gly Leu Cys Phe Leu Phe Gly Ser
        115                 120                 125
Asn Leu Arg Gln Gln Pro Gln Lys Phe Pro Glu Ala Leu Arg Gly Cys
    130                 135                 140
Pro Gln Glu Asp Ser Asp Ile Ala Phe Leu Ile Asp Gly Ser Gly Ser
145                 150                 155                 160
Ile Ile Pro His Asp Phe Arg Arg Met Lys Glu Phe Val Ser Thr Val
                165                 170                 175
Met Glu Gln Leu Lys Lys Ser Lys Thr Leu Phe Ser Leu Met Gln Tyr
            180                 185                 190
Ser Glu Phe Arg Ile His Phe Thr Phe Lys Glu Phe Gln Asn Asn
        195                 200                 205
Pro Asn Pro Arg Ser Leu Val Lys Pro Ile Thr Gln Leu Leu Gly Arg
    210                 215                 220
Thr His Thr Ala Thr Gly Ile Arg Lys Val Val Arg Glu Leu Phe Asn
225                 230                 235                 240
Ile Thr Asn Gly Ala Arg Lys Asn Ala Phe Lys Ile Leu Val Val Ile
                245                 250                 255
Thr Asp Gly Glu Lys Phe Gly Asp Pro Leu Gly Tyr Glu Asp Val Ile
            260                 265                 270
Pro Glu Ala Asp Arg Glu Gly Val Ile Arg Tyr Val Ile Gly Val Gly
        275                 280                 285
Asp Ala Phe Arg Ser Glu Lys Ser Arg Gln Glu Leu Asn Thr Ile Ala
    290                 295                 300
Ser Lys Pro Pro Arg Asp His Val Phe Gln Val Asn Asn Phe Glu Ala
305                 310                 315                 320
Leu Lys Thr Ile Gln Asn Gln Leu Arg Glu Lys Ile Phe Ala Ile Glu
                325                 330                 335
Gly Thr Gln Thr Gly Ser Ser Ser Phe Glu His Glu Met Ser Gln
            340                 345                 350
Glu Gly Phe Ser Ala Ala Ile Thr Ser Asn Gly Pro Leu Leu Ser Thr
        355                 360                 365
Val Gly Ser Tyr Asp Trp Ala Gly Gly Val Phe Leu Tyr Thr Ser Lys
    370                 375                 380
Glu Lys Ser Thr Phe Ile Asn Met Thr Arg Val Asp Ser Asp Met Asn
385                 390                 395                 400
Asp Ala Tyr Leu Gly Tyr Ala Ala Ala Ile Ile Leu Arg Asn Arg Val
                405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
        435                 440                 445
Lys Gly Thr Gln Ile Gly Ala Tyr Phe Gly Ala Ser Leu Cys Ser Val
    450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
                485                 490                 495
Pro Arg Gly Gln Arg Ala Arg Trp Gln Cys Asp Ala Val Leu Tyr Gly
            500                 505                 510
Glu Gln Gly Gln Pro Trp Gly Arg Phe Gly Ala Ala Leu Thr Val Leu
        515                 520                 525
Gly Asp Val Asn Gly Asp Lys Leu Thr Asp Val Ala Ile Gly Ala Pro
    530                 535                 540
Gly Glu Glu Asp Asn Arg Gly Ala Val Tyr Leu Phe His Gly Thr Ser
545                 550                 555                 560
Gly Ser Gly Ile Ser Pro Ser His Ser Gln Arg Ile Ala Gly Ser Lys
                565                 570                 575
Leu Ser Pro Arg Leu Gln Tyr Phe Gly Gln Ser Leu Ser Gly Gly Gln
            580                 585                 590
Asp Leu Thr Met Asp Gly Leu Val Asp Leu Thr Val Gly Ala Gln Gly
        595                 600                 605
His Val Leu Leu Leu Arg Ser Gln Pro Val Leu Arg Val Lys Ala Ile
    610                 615                 620
Met Glu Phe Asn Pro Arg Glu Val Ala Arg Asn Val Phe Glu Cys Asn
625                 630                 635                 640
```

-continued

```
Asp Gln Val Val Lys Gly Lys Glu Ala Gly Glu Val Arg Val Cys Leu
                645                 650                 655
His Val Gln Lys Ser Thr Arg Asp Arg Leu Arg Glu Gly Gln Ile Gln
            660                 665                 670
Ser Val Val Thr Tyr Asp Leu Ala Leu Asp Ser Gly Arg Pro His Ser
        675                 680                 685
Arg Ala Val Phe Asn Glu Thr Lys Asn Ser Thr Arg Arg Gln Thr Gln
    690                 695                 700
Val Leu Gly Leu Thr Gln Thr Cys Glu Thr Leu Lys Leu Gln Leu Pro
705                 710                 715                 720
Asn Cys Ile Glu Asp Pro Val Ser Pro Ile Val Leu Arg Leu Asn Phe
                725                 730                 735
Ser Leu Val Gly Thr Pro Leu Ser Ala Phe Gly Asn Leu Arg Pro Val
            740                 745                 750
Leu Ala Glu Asp Ala Gln Arg Leu Phe Thr Ala Leu Phe Pro Phe Glu
        755                 760                 765
Lys Asn Cys Gly Asn Asp Asn Ile Cys Gln Asp Leu Ser Ile Thr
    770                 775                 780
Phe Ser Phe Met Ser Leu Asp Cys Leu Val Val Gly Gly Pro Arg Glu
785                 790                 795                 800
Phe Asn Val Thr Val Thr Val Arg Asn Asp Gly Glu Asp Ser Tyr Arg
                805                 810                 815
Thr Gln Val Thr Phe Phe Pro Leu Asp Leu Ser Tyr Arg Lys Val
            820                 825                 830
Ser Thr Leu Gln Asn Gln Arg Ser Gln Arg Ser Trp Arg Leu Ala Cys
        835                 840                 845
Glu Ser Ala Ser Ser Thr Glu Val Ser Gly Ala Leu Lys Ser Thr Ser
    850                 855                 860
Cys Ser Ile Asn His Pro Ile Phe Pro Glu Asn Ser Glu Val Thr Phe
865                 870                 875                 880
Asn Ile Thr Phe Asp Val Asp Ser Lys Ala Ser Leu Gly Asn Lys Leu
                885                 890                 895
Leu Leu Lys Ala Asn Val Thr Ser Glu Asn Asn Met Pro Arg Thr Asn
            900                 905                 910
Lys Thr Glu Phe Gln Leu Glu Leu Pro Val Lys Tyr Ala Val Tyr Met
        915                 920                 925
Val Val Thr Ser His Gly Val Ser Thr Lys Tyr Leu Asn Phe Thr Ala
    930                 935                 940
Ser Glu Asn Thr Ser Arg Val Met Gln His Gln Tyr Gln Val Ser Asn
945                 950                 955                 960
Leu Gly Gln Arg Ser Pro Pro Ile Ser Leu Val Phe Leu Val Pro Val
                965                 970                 975
Arg Leu Asn Gln Thr Val Ile Trp Asp Arg Pro Gln Val Thr Phe Ser
            980                 985                 990
Glu Asn Leu Ser Ser Thr Cys His Thr Lys Glu Arg Leu Pro Ser His
        995                 1000                1005
Ser Asp Phe  Leu Ala Glu Leu Arg  Lys Ala Pro Val Val  Asn Cys
    1010             1015              1020
Ser Ile Ala  Val Cys Gln Arg Ile  Gln Cys Asp Ile Pro  Phe Phe
    1025             1030              1035
Gly Ile Gln  Glu Glu Phe Asn Ala  Thr Leu Lys Gly Asn  Leu Ser
    1040             1045              1050
Phe Asp Trp  Tyr Ile Lys Thr Ser  His Asn His Leu Leu  Ile Val
    1055             1060              1065
Ser Thr Ala  Glu Ile Leu Phe Asn  Asp Ser Val Phe Thr  Leu Leu
    1070             1075              1080
Pro Gly Gln  Gly Ala Phe Val Arg  Ser Gln Thr Glu Thr  Lys Val
    1085             1090              1095
Glu Pro Phe  Glu Val Pro Asn Pro  Leu Pro Leu Ile Val  Gly Ser
    1100             1105              1110
Ser Val Gly  Gly Leu Leu Leu Leu  Ala Leu Ile Thr Ala  Ala Leu
    1115             1120              1125
Tyr Lys Leu  Gly Phe Phe Lys Arg  Gln Tyr Lys Asp Met  Met Ser
    1130             1135              1140
Glu Gly Gly  Pro Pro Gly Ala Glu  Pro Gln
    1145             1150
```

SEQ ID NO: 3

```
ttttctgccc ttctttgctt tggtggcttc cttgtggttc ctcagtggtg cctgcaaccc    60
ctggttcacc tccttccagg ttctggctcc ttccagccat ggctctcaga gtccttctgt   120
taacagcctt gacctatgt catgggttca acttggacac tgaaaacgca atgaccttcc    180
aagagaacgc aagggcttc gggcagagcg tggtccagct tcagggatcc agggtgtgga    240
ttggagcccc caggagata gtggctgcca accaaagggg cagcctctac cagtgcgact    300
acagcacagg ctcatgcgag cccatccgcc tgcaggtccc cgtggaggcc gtgaacatgt    360
ccctgggcct gtccctggca gccaccacca gccccctca gctgctggcc tgtggtccca    420
ccgtgcacca gactttgcagt gagaacacgt atgtgaaagg gctctgcttc ctgtttggat    480
ccaacctacg gcagcagccc cagaagttcc agaggccct ccgagggtgt cctcaagagg    540
atagtgacat tgccttcttg attgatggct ctggtagcat catcccacat gactttcggc    600
ggatgaagga gtttgtctca actgtgatgg agcaattaaa aaagtccaaa accttgttct    660
ctttgatgca gtactctgaa gaattccgga ttcactttac cttcaagag ttccagaaca    720
accctaaccc aagatcactg gtgaagccaa taacgcagct gcttgggcgg acacacacgg    780
```

-continued

```
ccacgggcat ccgcaaagtg gtacgagagc tgtttaacat caccaacgga gcccgaaaga  840
atgcctttaa gatcctagtt gtcatcacgg atggagaaaa gtttggcgat cccttgggat  900
atgaggatgt catccctgag gcagacagag agggagtcat tcgctacgtc attggggtgg  960
gagatgcctt ccgcagtgag aaatcccgcc aagagcttaa taccatcgca tccaagccgc 1020
ctcgtgatca cgtgttccag gtgaataact ttgaggctct gaagaccatt cagaaccagc 1080
ttcgggagaa gatctttgcg atcgagggta ctcagacagg aagtagcagc tcctttgagc 1140
atgagatgtc tcaggaaggc ttcagcgctg ccatcacctc taatggcccc ttgctgagca 1200
ctgtggggag ctatgactgg gctggtggag tctttctata tacatcaaag gagaaaagca 1260
ccttcatcaa catgaccaga gtggattcag acatgaatga tgcttacttg ggttatgctg 1320
ccgccatcat cttacggaac cgggtgcaaa gcctggttct ggggcaccct cgatatcagc 1380
acatcggcct ggtagcgatg ttcaggcaga acactggcat gtgggagtcc aacgctaatg 1440
tcaagggcac ccagatcggc gcctacttcg gggcctccct ctgctccgtg gacgtggaca 1500
gcaacggcag caccgacctg gtcctcatcg ggcccccca ttactacgag cagacccgag 1560
ggggccaggt gtccgtgtgc cccttgccca gggggcagag ggctcggtgg cagtgtgatg 1620
ctgttctcta cggggagcag ggccaaccct ggggccgctt tggggcagcc ctaacagtgc 1680
tgggggacgt aaatggggac aagctgacgg acgtggccat tggggcccca ggagaggagg 1740
acaaccgggg tgctgtttac ctgtttcacg gaacctcagg atctggcatc agcccctccc 1800
atagccagcg gatagcaggc tccaagctct ctcccaggct ccagtatttt ggtcagtcac 1860
tgagtggggg ccaggacctc acaatggatg gactggtaga cctgactgta ggagcccagg 1920
ggcacgtgct gctgctcagg tcccagccag tactgagagt caaggcaatc atggagttca 1980
atcccaggga agtggcaagg aatgtatttg agtgtaatga tcaggtggtg aaaggcaagg 2040
aagccggaga ggtcagagtc tgcctccatg tccagaagga cacacgggat cggctaagag 2100
aaggacagat ccagagtgtt gtgacttatg acctggctct ggactccggc cgcccacatt 2160
cccgcgccgt cttcaatgag acaaagaaca gcacacgcag acagacacag gtcttgggc 2220
tgacccgac ttgtgagacc ctgaaactac agttgccgaa ttgcatcgag gacccagtga 2280
gcccattgt gctgcgcctg aacttctctc tggtgggaac gccattgtct gctttcgggg 2340
acctccggcc agtgctggcg gaggatgctc agagactctt cacagccttg tttccctttg 2400
agaagaattg tggcaatgac aacatctgcc aggatgacct cagcatcacc ttcagtttca 2460
tgagcctgga ctgcctcgtg gtgggtgggc ccgggagtt caacgtgaca gtgactgtga 2520
gaaatgatgg tgaggactcc tacaggacac aggtcacctt cttcttcccg cttgacctgt 2580
cctaccggaa ggtgtccacg ctccagaacc agcgctcaca gcgatcctcg cgcctggcct 2640
gtgagtctgc ctcctccacc gaagtgtctg gggccttgaa gagcaccagc tgcagcataa 2700
accaccccat cttcccggaa aactcagagg tcacctttaa tatcacgttt gatgtagact 2760
ctaaggcttc ccttggaaac aaactgctcc tcaaggccaa tgtgaccagt gagaacaaca 2820
tgcccagaac caacaaaacc gaattccaac tggagctgcc gtgaaatat gctgtctaca 2880
tggtggtcac cagccatggg gtctccacta aatatctcaa cttcacggcc tcagaaata 2940
ccagtcgggt catgcagcat caatatcagg tcagcaacct ggggcagagg agcctcccca 3000
tcagcctggt gttcttggtg cccgtccggc tgaaccagac tgtcatatgg gaccgccccc 3060
aggtcacctt ctccgagaac ctctcgagta cgtgccacac caaggagcgc ttgccctctc 3120
actccgactt tctggctgag cttcggaagg ccccgtggt gaactgctcc atcgctgtct 3180
gccagagaat ccagtgtgac atcccgttct ttggcatcca ggaagaattc aatgctaccc 3240
tcaaaggcaa cctctcgttt gactggtaca tcaagacctc gcataaccac ctcctgatcg 3300
tgagcacagc tgagatcttg tttaacgatt ccgtgttcac cctgctgccg ggacagggg 3360
cgtttgtgag gtcccagacg gagaccaaag tggagccgtt cgaggtcccc aaccccctgc 3420
cgctcatcgt gggcagctct gtcggggac tgctgctcct ggccctcatc accgccgcgc 3480
tgtacaagct cggcttcttc aagcggcaat acaaggacat gatgagtgaa ggggtccccc 3540
cggggccga accccagtag cggctccttc ccgacagagt gcctctcgg tggccagcag 3600
gactctgccc agaccacacg tagccccag gctgctggac acgtcggaca gcgaagtatc 3660
cccgacagga cgggcttggg cttccatttg tgtgtgtgca agtgtgtatg tgcgtgtgtg 3720
caagtgtctg tgtgcaagtg tgtgcacatg tgtgcgtgtg cgtgcatgtg cacttgcacg 3780
cccatgtgtg agtgtgtgca agtatgtgag tgtgtccaag tgtgtgtgtg tgtgtccatg 3840
tgtgtgcaag tgtgtgcatg tgtgcgagtg tgtgcatgtg tgtgctcagg ggcgtgtggc 3900
tcacgtgtgt gactcagatg tctctggcgt gtgggtaggt gacggcagcg tagcctctcc 3960
ggcagaaggg aactgcctgg gctcccttgt gcgtgggtga agccgctgct gggttttcct 4020
ccgggagagg ggacggtcaa tcctgtgggt gaagacagag ggaaacacag cagcttctct 4080
ccactgaaag aagtgggact tcccgtcgcc tgcgagcctg cggcctgctg gagcctgcgc 4140
agcttggatg gagactccat gagaagccgt gggtggaacc aggaacctcc tccacaccag 4200
cgctgatgcc caataaagat gcccactgag gaatgatgaa gcttcctttc tggattcatt 4260
tattatttca atgtgacttt aatttttgg atggataagc ttgtctatgg tacaaaaatc 4320
acaaggcatt caagtgtaca gtgaaaagtc tcccttttcca gatattcaag tcacctcctt 4380
aaaggtagtc aagattgtgt tttgaggttt ccttcagaca gattccaggc gatgtgcaag 4440
tgtatgcacg tgtgcacaca caccacacat acacacacac aagctttttt acacaaatgg 4500
tagcatactt tatattggtc tgtatcttgc tttttttcac caatatttct cagacatcgg 4560
ttcatattaa gacataaatt acttttttcat tcttttatac cgctgcatag tattccattg 4620
tgtgagtgta ccataatgta tttaaccagt cttccttttga tatactatttt tcattctctt 4680
gttattgcat caatgctgag ttaataaatc aaatatatgt catttttgca tatatgtaag 4740
gataa                                                              4745
```

SEQ ID NO: 4

| | | | | | | | | | | | | | | |
|---|---|---|---|---|---|---|---|---|---|---|---|---|---|---|
Met Ala Leu Arg Val Leu Leu Thr Ala Leu Thr Leu Cys His Gly
1               5                  10                 15
Phe Asn Leu Asp Thr Glu Asn Ala Met Thr Phe Gln Glu Asn Ala Arg
                20                 25                 30
Gly Phe Gly Gln Ser Val Val Gln Leu Gln Gly Ser Arg Val Val Val
            35                 40                 45
Gly Ala Pro Gln Glu Ile Val Ala Ala Asn Gln Arg Gly Ser Leu Tyr
        50                 55                 60
Gln Cys Asp Tyr Ser Thr Gly Ser Cys Glu Pro Ile Arg Leu Gln Val
65                 70                 75                 80
Pro Val Glu Ala Val Asn Met Ser Leu Gly Leu Ser Leu Ala Ala Thr
                85                 90                 95

-continued

```
Thr Ser Pro Pro Gln Leu Leu Ala Cys Gly Pro Thr Val His Gln Thr
            100                 105                 110
Cys Ser Glu Asn Thr Tyr Val Lys Gly Leu Cys Phe Leu Phe Gly Ser
        115                 120                 125
Asn Leu Arg Gln Gln Pro Gln Lys Phe Pro Glu Ala Leu Arg Gly Cys
    130                 135                 140
Pro Gln Glu Asp Ser Asp Ile Ala Phe Leu Ile Asp Gly Ser Gly Ser
145                 150                 155                 160
Ile Ile Pro His Asp Phe Arg Arg Met Lys Glu Phe Val Ser Thr Val
                165                 170                 175
Met Glu Gln Leu Lys Lys Ser Lys Thr Leu Phe Ser Leu Met Gln Tyr
            180                 185                 190
Ser Glu Glu Phe Arg Ile His Phe Thr Phe Lys Glu Phe Gln Asn Asn
        195                 200                 205
Pro Asn Pro Arg Ser Leu Val Lys Pro Ile Thr Gln Leu Leu Gly Arg
    210                 215                 220
Thr His Thr Ala Thr Gly Ile Arg Lys Val Val Arg Glu Leu Phe Asn
225                 230                 235                 240
Ile Thr Asn Gly Ala Arg Lys Asn Ala Phe Lys Ile Leu Val Val Ile
                245                 250                 255
Thr Asp Gly Glu Lys Phe Gly Asp Pro Leu Gly Tyr Glu Asp Val Ile
            260                 265                 270
Pro Glu Ala Asp Arg Glu Gly Val Ile Arg Tyr Val Ile Gly Val Gly
        275                 280                 285
Asp Ala Phe Arg Ser Glu Lys Ser Arg Gln Glu Leu Asn Thr Ile Ala
    290                 295                 300
Ser Lys Pro Pro Arg Asp His Val Phe Gln Val Asn Asn Phe Glu Ala
305                 310                 315                 320
Leu Lys Thr Ile Gln Asn Gln Leu Arg Glu Lys Ile Phe Ala Ile Glu
                325                 330                 335
Gly Thr Gln Thr Gly Ser Ser Ser Phe Glu His Glu Met Ser Gln
            340                 345                 350
Glu Gly Phe Ser Ala Ala Ile Thr Ser Asn Gly Pro Leu Leu Ser Thr
        355                 360                 365
Val Gly Ser Tyr Asp Trp Ala Gly Gly Val Phe Leu Tyr Thr Ser Lys
    370                 375                 380
Glu Lys Ser Thr Phe Ile Asn Met Thr Arg Val Asp Ser Asp Met Asn
385                 390                 395                 400
Asp Ala Tyr Leu Gly Tyr Ala Ala Ala Ile Ile Leu Arg Asn Arg Val
                405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
        435                 440                 445
Lys Gly Thr Gln Ile Gly Ala Tyr Phe Gly Ala Ser Leu Cys Ser Val
    450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
                485                 490                 495
Pro Arg Gly Gln Arg Ala Arg Trp Gln Cys Asp Ala Val Leu Tyr Gly
            500                 505                 510
Glu Gln Gly Gln Pro Trp Gly Arg Phe Gly Ala Ala Leu Thr Val Leu
        515                 520                 525
Gly Asp Val Asn Gly Asp Lys Leu Thr Asp Val Ala Ile Gly Ala Pro
    530                 535                 540
Gly Glu Glu Asp Asn Arg Gly Ala Val Tyr Leu Phe His Gly Thr Ser
545                 550                 555                 560
Gly Ser Gly Ile Ser Pro Ser His Ser Gln Arg Ile Ala Gly Ser Lys
                565                 570                 575
Leu Ser Pro Arg Leu Gln Tyr Phe Gly Gln Ser Leu Ser Gly Gly Gln
            580                 585                 590
Asp Leu Thr Met Asp Gly Leu Val Asp Leu Thr Val Gly Ala Gln Gly
        595                 600                 605
His Val Leu Leu Leu Arg Ser Gln Pro Val Leu Arg Val Lys Ala Ile
    610                 615                 620
Met Glu Phe Asn Pro Arg Glu Val Ala Arg Asn Val Phe Glu Cys Asn
625                 630                 635                 640
Asp Gln Val Val Lys Gly Lys Glu Ala Gly Glu Val Arg Val Cys Leu
                645                 650                 655
His Val Gln Lys Ser Thr Arg Asp Arg Leu Arg Glu Gly Gln Ile Gln
            660                 665                 670
Ser Val Val Thr Tyr Asp Leu Ala Leu Asp Ser Gly Arg Pro His Ser
        675                 680                 685
Arg Ala Val Phe Asn Glu Thr Lys Asn Ser Thr Arg Arg Gln Thr Gln
    690                 695                 700
Val Leu Gly Leu Thr Gln Thr Cys Glu Thr Leu Lys Leu Gln Leu Pro
705                 710                 715                 720
Asn Cys Ile Glu Asp Pro Val Ser Pro Ile Val Leu Arg Leu Asn Phe
                725                 730                 735
Ser Leu Val Gly Thr Pro Leu Ser Ala Phe Gly Asn Leu Arg Pro Val
```

```
                      740                      745                         750
Leu Ala Glu Asp Ala Gln Arg Leu Phe Thr Ala Leu Phe Pro Phe Glu
                755                      760                 765
Lys Asn Cys Gly Asn Asp Asn Ile Cys Gln Asp Asp Leu Ser Ile Thr
770                      775                      780
Phe Ser Phe Met Ser Leu Asp Cys Leu Val Val Gly Gly Pro Arg Glu
785                      790                      795                 800
Phe Asn Val Thr Val Thr Val Arg Asn Asp Gly Glu Asp Ser Tyr Arg
                    805                      810                 815
Thr Gln Val Thr Phe Phe Pro Leu Asp Leu Ser Tyr Arg Lys Val
                820                      825                 830
Ser Thr Leu Gln Asn Gln Arg Ser Gln Arg Ser Trp Arg Leu Ala Cys
                835                      840                 845
Glu Ser Ala Ser Ser Thr Glu Val Ser Gly Ala Leu Lys Ser Thr Ser
850                      855                      860
Cys Ser Ile Asn His Pro Ile Phe Pro Glu Asn Ser Glu Val Thr Phe
865                      870                      875                 880
Asn Ile Thr Phe Asp Val Asp Ser Lys Ala Ser Leu Gly Asn Lys Leu
                    885                      890                 895
Leu Leu Lys Ala Asn Val Thr Ser Glu Asn Asn Met Pro Arg Thr Asn
                900                      905                 910
Lys Thr Glu Phe Gln Leu Glu Leu Pro Val Lys Tyr Ala Val Tyr Met
            915                      920                 925
Val Val Thr Ser His Gly Val Ser Thr Lys Tyr Leu Asn Phe Thr Ala
930                      935                      940
Ser Glu Asn Thr Ser Arg Val Met Gln His Gln Tyr Gln Val Ser Asn
945                      950                      955                 960
Leu Gly Gln Arg Ser Leu Pro Ile Ser Leu Val Phe Leu Val Pro Val
                    965                      970                 975
Arg Leu Asn Gln Thr Val Ile Trp Asp Arg Pro Gln Val Thr Phe Ser
                980                      985                 990
Glu Asn Leu Ser Ser Thr Cys His Thr Lys Glu Arg Leu Pro Ser His
                995                      1000                    1005
Ser Asp Phe Leu Ala Glu Leu Arg Lys Ala Pro Val  Val Asn Cys
    1010                      1015                1020
Ser Ile Ala Val Cys Gln Arg  Ile Gln Cys Asp Ile Pro Phe Phe
    1025                      1030                 1035
Gly Ile  Gln Glu Glu Phe Asn Ala Thr Leu Lys Gly Asn Leu Ser
    1040                      1045                1050
Phe Asp Trp Tyr Ile Lys Thr Ser His Asn His Leu  Leu Ile Val
    1055                      1060                 1065
Ser Thr Ala Glu Ile Leu Phe Asn Asp Ser Val Phe  Thr Leu Leu
    1070                      1075                 1080
Pro Gly Gln Gly Ala Phe Val Arg Ser Gln Thr Glu  Thr Lys Val
    1085                      1090                 1095
Glu Pro Phe Glu Val Pro Asn Pro Leu Pro Leu Ile  Val Gly Ser
    1100                      1105                 1110
Ser Val Gly Gly Leu Leu Leu Leu Ala Leu Ile Thr  Ala Ala Leu
    1115                      1120                 1125
Tyr Lys Leu Gly Phe Phe Lys Arg Gln Tyr Lys Asp  Met Met Ser
    1130                      1135                 1140
Glu Gly Gly Pro Pro Gly Ala Glu Pro Gln
    1145                      1150
```

A polynucleotide sequence encoding a human CD11b protein or polypeptide can be integrated into the genome of the transgenic mouse by any standard method well known to those skilled in the art. Any of a variety of techniques known in the art can be used to introduce the transgene into an animal to produce the founder line of transgenic animals (see e.g., Hogan et al., Manipulating the Mouse Embryo: A Laboratory Manual (Cold Spring Harbor Laboratory, 1986); Hogan et al., Manipulating the Mouse Embryo: A Laboratory Manual (Cold Spring Harbor Laboratory, 1994), and U.S. Pat. No. 5,602,299 to Lazzarini; U.S. Pat. No. 5,175,384 to Krimpenfort; U.S. Pat. No. 6,066,778 to Ginsburg; and U.S. Pat. No. 6,037,521 to Sato et al, which are hereby incorporated by reference in their entirety). Such techniques include, but are not limited to, pronuclear microinjection (U.S. Pat. No. 4,873,191 to Wagner et al., which is hereby incorporated by reference in its entirety); retrovirus mediated gene transfer into germ lines (Van der Putten et al., *Proc. Natl. Acad. Sci. USA* 82:6148-6152 (1985), which is hereby incorporated by reference in its entirety); gene targeting in embryonic stem cells (Thompson et al., *Cell* 56:313-321 (1989), which is hereby incorporated by reference in its entirety); electroporation of embryos (Lo et al., *Mol. Cell. Biol.* 3:1803-1814 (1983), which is hereby incorporated by reference in its entirety); and sperm-mediated gene transfer (Lavitrano et al., *Cell* 57:717-723 (1989), which is hereby incorporated by reference in its entirety).

For example, embryonic cells at various developmental stages can be used to introduce transgenes for the production of transgenic animals. Different methods are used depending on the stage of development of the embryonic cell. The zygote is a good target for micro-injection, and methods of microinjecting zygotes are well known to (see U.S. Pat. No. 4,873,191 to Wagner et al., which is hereby incorporated by reference in its entirety). In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., *Proc. Natl. Acad. Sci. USA* 82:4438-4442 (1985), which is hereby incorporated by reference in its entirety). As a consequence, all cells of the transgenic non-human animal will carry the incorporated transgene. This will in general also be reflected in the efficient transmission of the transgene to offspring of the founder since 50% of the germ cells will harbor the transgene.

The transgenic animals of the present invention can also be generated by introduction of the targeting vectors into embryonic stem (ES) cells. ES cells are obtained by culturing pre-implantation embryos in vitro under appropriate conditions (Evans et al., *Nature* 292:154-156 (1981); Bradley et al., *Nature* 309:255-258 (1984); Gossler et al., *Proc. Natl. Acad. Sci. USA* 83:9065-9069 (1986); and Robertson et al., *Nature* 322:445-448 (1986), which are hereby incorporated by reference in their entirety). Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (reviewed in Jaenisch, *Science* 240:1468-1474 (1988), which is hereby incorporated by reference in its entirety). Prior to the introduction of transfected ES cells into the blastocoel, the transfected ES cells can be subjected to various selection protocols to enrich for ES cells that have integrated the transgene if the transgene provides a means for such selection. Alternatively, PCR can be used to screen for ES cells that have integrated the transgene. This technique obviates the need for growth of the transfected ES cells under appropriate selective conditions prior to transfer into the blastocoel.

In addition, retroviral infection can also be used to introduce transgenes into a non-human animal. The developing non-human embryo can be cultured in vitro to the blastocyst stage. During this time, the blastomeres can be targets for retroviral infection (Janenich, *Proc. Natl. Acad. Sci. USA* 73:1260-1264 (1976), which is hereby incorporated by reference in its entirety). The viral vector system used to introduce the transgene is typically a replication-defective retrovirus carrying the transgene (Jahner et al., *Proc. Natl. Acad. Sci. USA* 82:6927-6931 (1985); Van der Putten et al. *Proc. Natl. Acad. Sci. USA* 82:6148-6152 (1985)). Transfection is easily and efficiently obtained by culturing the blastomeres on a monolayer of virus-producing cells. Alternatively, infection can be performed at a later stage. Additional means of using retroviruses or retroviral vectors to create transgenic animals known to the art involves the micro-injection of retroviral particles or mitomycin C-treated cells producing retrovirus into the perivitelline space of fertilized eggs or early embryos (WO 90/08832 to Onions, which is hereby incorporated by reference in its entirety).

The present invention provides transgenic non-human animals that carry the transgene in all their cells, as well as animals that carry the transgene in some, but not all their cells, i.e., expression of the transgene is controlled by a cell specific promoter and/or enhancer elements placed upstream of the transgene. In one embodiment of the present invention, the transgenic animal expressing human CD11b, expresses the CD11b transgene in leukocytes only. In accordance with this embodiment of the invention, a leukocyte specific promoter sequence is operably linked to the polynucleotide sequence encoding human CD11b. Suitable leukocyte specific promoters include, without limitation, the LSP1 promoter (Malone et al, "Leukocyte-Specific Expression of the pp52 (LSP1) Promoter is Controlled by the cis-acting pp52 Silencer and Anti-Silencer Elements," *Gene* 268:9-16 (2001), which is hereby incorporated by reference in its entirety), macrosialin promoter (Li et al., "The Macrosialin Promoter Directs High Levels of Transcriptional Activity in Macrophages Dependent on Combinatorial Interactions Between Pu.1 and c-Jun," *J. Biol. Chem.* 273:5389-5399 (1998), which is hereby incorporated by reference in its entirety), lysozyme promoter (Bonifer et al., "Tissue Specific and Position Independent Expression of the Complete Gene Domain for the Chicken Lysozyme in Transgenic Mice," *EMBO J.* 9:2843-48 (1990), which is hereby incorporated by reference in its entirety), and the myeloid specific CD11b promoter to promote the expression of the human CD11b only in cells that normally express CD11b (e.g., granulocytes, monocytes, macrophages and Natural Killer cells) (Pahl et al., "Characterization of the Myeloid-Specific CD11b Promoter," *Blood* 79:865-870 (1992) and Hickstein et al., "Identification of the Promoter of the Myelomonocytic Leukocyte Integrin CD11b," *Proc. Natl. Acad. Sci. USA* 89:2105-09 (1992), which are hereby incorporated by reference in their entirety). Expression or cloning constructs suitable for driving transgene expression in a transgenic animal are well known in the art. Other components of the expression construct include a strong polyadenylation site, appropriate restriction endonuclease sites, and introns to ensure the transcript is spliced.

The polynucleotides encoding human CD11b can be inserted into any non-human animal. In one embodiment the animal is a rodent, for example, a mouse. Suitable strains of mice commonly used in the generation of transgenic models include, without limitation, CD-1® Nude mice, NU/NU mice, BALB/C Nude mice, BALB/C mice, NIH-III mice, SCID® mice, outbred SCID® mice, SCID Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice.

The transgenic animals are screened and evaluated to select those animals having a phenotype wherein human CD11b is expressed on all cells or on leukocytes specifically. Initial screening can be performed using, for example, Southern blot analysis or PCR techniques to analyze animal cells to verify that integration of the transgene has taken place. The level of mRNA expression of the transgene in the cells of the transgenic animals can also be assessed using techniques which include, but are not limited to, Northern blot analysis of tissue samples obtained from the animal, in situ hybridization analysis, and reverse transcriptase-PCR (rt-PCR). In addition, surface expression of human CD11b can be evaluated by flow cytometry using human-specific anti-CD11b antibodies conjugated with fluorescent molecules. The transgenic non-human mammals can be further characterized to identify those animals having a phenotype useful in methods of the invention. In particular, the transgenic non-human animal can be exposed to *S. aureus* and leukocyte cell death can be examined.

Another aspect of the present invention relates to methods of identifying candidate compounds suitable for preventing or treating *S. aureus* infection and/or conditions resulting from a *S. aureus* infection using the transgenic non-human animal of the present invention. In one embodiment of this aspect of the invention, the method of identifying candidate compounds involves providing a collection of candidate compounds. The method further involves exposing the transgenic animal expressing human CD11b to an agent capable of inducing LukAB mediated leukocyte death and administering the one or more candidate compounds to the transgenic animal. The method further involves measuring LukAB mediated leukocyte death level in the transgenic animal to which the one or more candidate compounds are administered and comparing that level of LukAB mediated leukocyte death in the transgenic animal to which the one or more candidate compounds are administered to a control level of LukAB mediated leukocyte death in a transgenic animal to which the one or more candidate compounds was not administered. A control level of LukAB mediated cell death is the level of LukAB mediated cell death in a transgenic animal administered the LukAB agent but not the candidate compound. A candidate compound that reduces the level of LukAB mediated leukocyte death in the transgenic animal compared to the control level is identified as a compound suitable for preventing or treating S. aureus and/or conditions resulting from a S. aureus infection.

In accordance with this method of the present invention, agents capable of inducing LukAB mediated leukocyte death, or cell death of any cell expressing the human CD11b protein, include, without limitation, S. aureus particularly a MRSA or MSSA strain, a composition comprising an isolated LukA, LukB or LukAB protein complex, a composition comprising a recombinantly produced LukA, LukB, or LukAB protein complex, or a prokaryotic and/or eukaryotic cells engineered to produced LukA, LukB or LukAB protein complex.

In one embodiment of this aspect of the invention, the candidate compound is administered prior to exposing the transgenic animal to the agent capable of inducing LukAB cytotoxicity as a means for identifying a suitable prophylactic agent. Alternatively, the candidate compound is administered after exposure of the transgenic animal to the LukAB agent as a means for identifying a suitable therapeutic agent.

Another method of the present invention for identifying candidate compounds suitable for preventing or treating S. aureus infection and/a condition resulting from a S. aureus infection using the transgenic rodent involves the steps of providing a collection of candidate compounds exposing the transgenic animal expressing human CD11b to S. aureus and administering a one or more candidate compounds from the collection to the transgenic animal. The method further involves measuring S. aureus infection level in the transgenic animal to which the one or more candidate compounds was administered, comparing the S. aureus infection level in the transgenic animal to which the one or more candidate compounds was administered to a control S. aureus infection level in a transgenic animal that was exposed to S. aureus but not administered the one or more candidate compounds, and identifying a candidate compound that reduces S. aureus infection level in the transgenic animal compared to the control S. aureus infection level as a compound suitable for preventing or treating S. aureus and/or conditions resulting from a S. aureus infection.

Measuring S. aureus infection level encompasses evaluation or measurement of any one or more indicators of S. aureus infection, including, without limitation, animal survival, cell viability, inflammatory response, bacterial burden, and infection related pathology. A candidate compound that increases animal survival and/or cell viability, reduces the inflammatory response or bacterial burden in the animal, and improves pathology of infection is a compound that is suitable for preventing or treating S. aureus and/or a condition resulting from a S. aureus infection.

In one embodiment of this aspect of the invention, the candidate compound is administered prior to exposing the transgenic animal to S. aureus as a means for identifying suitable prophylactic agents. Alternatively, the candidate compound is administered after exposure of the transgenic animal to S. aureus as a means for identifying suitable therapeutic agents.

Another aspect of the present invention relates to a method of identifying a compound capable of preventing or treating S. aureus infection and/or conditions resulting from a S. aureus infection. This method is typically carried out in vitro, i.e., in cell culture. This method involves providing a collection of candidate compounds and providing a population of cells expressing human CD11b. The method further involves treating the population of cells with an agent capable of inducing LukAB mediated cytotoxicity, and contacting the population of treated cells with one or more candidate compounds from the collection. The method further involves measuring LukAB mediated cytotoxicity level in the population of treated cells in the presence and absence of the one or more candidate compounds and comparing the measured level of LukAB mediated cytotoxicity in the presence and in the absence of the one or more candidate compound. A decrease in the level of LukAB mediated cytotoxicity in the presence of the one or more candidate compounds compared to in its absence of the one or more candidate compounds identifies a compound capable of preventing or treating S. aureus infection and/or a condition resulting from a S. aureus infection.

Cells expressing human CD11b that are suitable for use in accordance with this aspect of the invention include human leukocytes, such as monocytes, granulocytes, macrophages, and natural killer cells. Other suitable cells include any nucleated cell that has been engineered to express CD11b, e.g., cells stably or transiently transfected with an expression construct containing a human CD11b polynucleotide sequence (e.g., an expression construct comprising the nucleotide sequence of SEQ ID NOs: 1 or 3).

As described herein, this method of the present invention is designed to identify agents that inhibit some aspect of the cascade of events that leads to LukAB-mediated cytotoxicity and lysis of human phagocytes. The targeted events that are part of the cascade include for example, binding of LukA and/or LukB to the CD11b receptor on phagocytes, binding of LukB to LukA (LukAB oligomerization), and blockage of the membrane pore formed by the LukAB oligomer. The assay utilizes any mammalian or non-mammalian cell expressing the human CD11b protein or a fragment thereof that comprises the LukAB binding domain, suitable culture medium, and isolated or recombinant LukA and/or LukB, or S. aureus. The assay further includes a labeled marker of cytotoxicity that is exposed to the cells before, during, or after the cells expressing human CD11b are contacted with an agent capable of inducing LukAB cytotoxicity. The labeled marker of cytotoxicity may comprise a cell viability dye, a cell impermeable dye, and/or an indicator of cell lysis.

The person of skill will appreciate that the following protocols are merely illustrative and that various operating parameters such as reaction conditions, choice of detectable label and apparati (e.g., instrumentation for detection and quantification) may be varied as deemed appropriate. The following methods are generally directed to identifying agents that inhibit LukAB cytotoxicity, without necessarily revealing the exact event in the cascade that is affected.

To identify inhibitors of CD11b-LukAB cytotoxicity, cells expressing human CD11b (e.g., human phagocytes or murine phagocytes transfected with human CD11b) are plated in 384-well clear-bottom black tissue culture treated plate (Corning) at $5\times10^3$ cells/well in a final volume of 50 µl of RPMI (Gibco) supplemented with 10% of heat inactivated fetal bovine serum (FBS). Cells may then be contacted/mixed/reacted/treated with the test compound/molecule (~5 µl/different concentrations) and then intoxicated with LukA and LukB, which in preferred embodiments are substantially purified (5 ul of a ~0.001-2 µM solution), preferably added together, under culture conditions to allow for intoxication of the phagocytes by LukA and LukB, e.g., for 1 hr at 37° C., 5% $CO_2$, As controls, cells may be treated with culture medium (100% viable) and with 0.1% v/v Triton X100 (100% death).

In these embodiments, cells treated as described above may then be incubated with a dye to monitor cell viability such as CellTiter (Promega) (which enables determination of cell viability via absorbance by measuring the number of viable cells in a culture by quantification of the metabolic activity of the cells) and incubated for an additional time period (e.g., about 2 hrs at 37° C., 5% $CO_2$). Cell viability may then be determined such as by measuring the colorimetric reaction at 492 nm using a plate reader e.g., Envision 2103 Multi-label Reader (Perkin-Elmer). Percent viable cells may be calculated such as by using the following equation: % Viability=$100\times[(Ab_{492}Sample-Ab_{492}Triton X)/(Ab_{492}Tissue$ culture media)]. An increase in the percent viability suggests inhibition of LukAB cytotoxicity.

A variation of this assay is referred to as a membrane damage assay. In these embodiments, cells treated as described above (e.g., up to and including treating of the cells with test compound/molecule and then intoxicating the cells with purified LukA or LukAB may then be incubated with a cell-impermeable fluorescent dye such as SYTOX green (0.1 µM; Invitrogen) (in accordance with manufacturer's instructions) and incubated e.g., for an additional 15 minutes at room temperature in the dark. Fluorescence, as an indicator of membrane damage, may then be measured using a plate reader such as Envision 2103 Multilabel Reader (Perkin-Elmer) at Excitation 485 nm, Emission 535 nm. A decrease in fluorescence suggests inhibition of LukAB cytotoxicity.

Together these assays facilitate the identification of compounds that inhibit or reduce LukAB cytotoxic effects towards cells expressing human CD11b. Additional methods may be used, independently or in conjunction with the methods described above, particularly if the above methods reveal inhibitory activity, that will enable a person skilled in the field to determine more precisely what event in the biochemical cascade is being affected or targeted by the agent. These events include binding of LukA, LukB or LukAB to the CD11b receptor, binding of LukB to LukA (LukAB oligomerization), and blockage of the membrane pore formed by the LukAB oligomer.

To screen for inhibitors that block or reduce LukA, LukB, or LukAB binding to target cells, which is believed to be the first step in the intoxication process, cells expressing human CD11b (e.g., PMN-HL60 cells) may be plated in 384-well flat-bottom tissue culture treated plates (Corning) at $2.5\times10^3$ cells/well in a final volume of 50 µl of RPMI (Gibco) supplemented with 10% of heat inactivated fetal bovine serum (FBS). Cells may then be treated with the test compound/molecule (~5 µl/different concentrations) and intoxicated with purified, fluorescently labeled LukA, LukB, or LukAB (e.g., FITC, Cy3, Cy5, APC, PE) 5 ul of a ~0.01-2 µM solution for 1 hr at 37° C., 5% $CO_2$. To evaluate the efficacy of the tested compounds/molecules, the cell-associated fluorescence may be measured as an indicator of LukA, LukB, or LukAB binding to CD11b, e.g., using an automated fluorescence microscopic imaging system designed for high content screening and high content analysis (e.g., Cellomics ArrayScan ECS Reader (Thermo Scientific) (Excitation 485 nm, Emission 535 nm)).

To screen for inhibitors that block or reduce LukA/LukB interaction, which is believed to be the second step in the intoxication process, cells expressing human CD11b (e.g., PMN-HL60 cells) may be plated in 384-well flat-bottom tissue culture treated plates (Corning) at $2.5\times10^3$ cells/well in a final volume of 50 µl of RPMI (Gibco) supplemented with 10% of heat inactivated fetal bovine serum (FBS). Cells may then be treated with the test compound/molecule and then intoxicated with a mixture of purified LukA and purified LukB where LukB is fluorescently-labeled with a fluorescence molecule such as FITC, Cy3, Cy5, APC, and PE, and allowed to stand to complete the intoxication process (e.g., for 1 hr at 37° C., 5% $CO_2$). To evaluate the efficacy of the tested compounds/molecules, cell-associated LukB-FITC fluorescence may be measured as an indicator of LukA/LukB-FITC interaction, using for example, an automated fluorescence microscopic imaging system designed for high content screening and high content analysis (e.g., a Cellomics ArrayScan ECS Reader (Thermo Scientific) (Excitation 485 nm, Emission 535 nm)).

To screen for inhibitors that block or inhibit formation of the LukAB pore, the effector molecule that leads to cell lysis, cells expressing human CD11b (e.g., PMN-HL60 cells) may be plated in 384-well clear-bottom black tissue culture treated plate (Corning) at $2.5\times10^3$ cells/well in a final volume of 50 µl of RPMI (Gibco) supplemented with 10% of heat inactivated fetal bovine serum (FBS) and 50 µM of the ethidium bromide cation dye. LukAB pores facilitate the uptake of this dye. Cells may then be treated with the test compound/molecule (~5 µl containing different concentrations) and then intoxicated with purified LukAB (0.001-2 µM) for 10-20 minutes at 37° C., 5% $CO_2$. Fluorescence, as an indicator of membrane damage, may then be measured using a plate reader such as Envision 2103 Multilabel Reader (Perkin-Elmer). A decrease in fluorescence suggests inhibition of LukAB pores. As controls, PMN-HL60 cells may be treated with culture medium (negative control) and with 0.01% v/v Triton X100 (positive control).

Another aspect of the present invention relates to a method of identifying candidate compounds capable of preventing or treating S. aureus infection and/or a condition resulting from a S. aureus infection. This method involves providing a collection of candidate compounds and providing an isolated CD11b receptor or a fragment thereof comprising a LukAB binding domain. The method further involves treating the isolated CD11b receptor or the fragment thereof with an agent comprising a labeled LukA, LukB, and/or labeled LukAB protein and contacting the treated, isolated CD11b receptor or the fragment thereof with one or more candidate compounds from the collection. The binding level of the labeled LukA, LukB, and/or labeled LukAB to the isolated CD11b receptor or fragment thereof is measured in the presence and in the absence of one or more candidate compounds, and the level of LukA, LukB, and/or LukAB binding to the isolated CD11b receptor or fragment thereof in the presence and absence of the one or more candidate compounds is compared. One or more candidate compounds that are capable of preventing or treating S. aureus infection and/or a condition resulting from a S. aureus infection are identified based on this comparison.

In accordance with this aspect of the present invention, a decrease in LukA, LukB, and/or LukAB binding to the isolated CD11b receptor or fragment thereof in the presence of the candidate compound compared to in its absence identifies a compound capable of preventing or treating *S. aureus* infection and/or a condition resulting from a *S. aureus* infection.

In accordance with this aspect of the present invention, methods of carrying out in vitro ligand binding assays in the presence and in the absence of candidate CD11b inhibitor agents are well known in the art (see e.g., Bansal et al., "Small Molecule Antagonists of Complement Receptor Type 3 Block Adhesion and Adhesion-Dependent Oxidative Burst in Human Polymorphonuclear Leukocytes," *J. Pharm. Exp. Therap.* 304(3):1016-24 (2003), which is hereby incorporated by reference in its entirety). These methods typically involve isolation and purification of CD11b or CD11b/CD18 receptor complex from suitable cells, e.g., human PMNs using the method described by Cai et al., "Energetics of Leukocyte Integrin Activation," *J. Biol. Chem.* 270:14358-65 (1995) and modified by, Bansal et al., "Small Molecule Antagonists of Complement Receptor Type 3 Block Adhesion and Adhesion-Dependent Oxidative Burst in Human Polymorphonuclear Leukocytes," *J. Pharm. Exp. Therap.* 304(3):1016-24 (2003) both of which are hereby incorporated by reference in their entirety. Alternatively, CD11b, a fragment thereof, or CD11b/CD18 can be recombinantly produced. When a peptide or polypeptide of CD11b comprising the LukAB binding domain is utilized in the method of the present invention, the desired peptide or polypeptide can be synthetically produced. This aspect of the present invention further involves purification and labeling of isolated or recombinant LukA, LukB and LukAB proteins. The polynucleotides sequences encoding LukA and LukB and methods of synthesizing or isolating LukA and LukB are described in detail in U.S. Patent Publication No. 2011/0274693 to Torres et al., which is hereby incorporated by reference in its entirety. Finally, methods of measuring labeled LukA, LukB, and/or LukAB binding to the isolated CD11b receptor, fragment thereof, or CD11b/CD18 receptor complex in the presence and absence of a candidate CD inhibitor are fully described in Bansal et al., "Small Molecule Antagonists of Complement Receptor Type 3 Block Adhesion and Adhesion-Dependent Oxidative Burst in Human Polymorphonuclear Leukocytes," *J. Pharm. Exp. Therap.* 304(3):1016-24 (2003), which is hereby incorporated by reference in its entirety.

EXAMPLES

The following examples are provided to illustrate embodiments of the present invention but are by no means intended to limit its scope.

Materials and Methods for Examples 1-7

Cell Culture.

HL60 and HEK293T cells were maintained at 37° C. with 5% $CO_2$ in RPMI and DMEM, respectively, both supplemented with 10% fetal bovine serum (FBS; Atlanta Biologicals) and penicillin (100 U/ml) and streptomycin (0.1 mg/ml) (Mediatech) unless stated otherwise. HL60 cells were differentiated into PMN-HL60 cells with 1.5% dimethyl sulfoxide (DMSO; Sigma Aldrich) for 72 hours at ~2.5×10$^5$. Transduced HL60 cells were maintained in 2 µg/ml puromycin.

Isolation of Primary Human PMNs.

Blood samples were obtained from anonymous healthy donors as buffy coats (New York Blood Center). The New York City Blood Center obtained written informed consent from all participants involved in the study. PMNs were isolated by Dextran gradient.

His-LukAB Purification from *S. aureus*.

To co-purify recombinant LukAB from *S. aureus* a construct was generated where LukA was fused to an N-terminal 6×-Histidine (His) tag. The construct was generated through multiple cloning steps by first PCR-amplifying the lukAB promoter region and lukA signal sequence from *S. aureus* Newman genomic DNA where nucleotides encoding a 6×-His tag were added after the lukA signal sequence (ss) using the following primers:

```
                                       (SEQ ID NO: 5)
5'-CCCCCCGGGGTGTTATTTGATTTCGTTCTATG-3'
and (SEQ ID NO: 6)
5'-CCCGGATCCGTGGTGGTGGTGGTGGTGAGCTGAAT
TTGCTTGAGTCGTTG-3'.
```

The amplified sequences were cloned into the pOS1 plasmid (Schneewind et al., "Sorting of Protein A to the Staphylococcal Cell Wall," *Cell* 70(2):267-281 (1992), which is hereby incorporated by reference in its entirety) using XmaI and BamHI. Then lukB with the lukAB intergenic region was PCR-amplified from *S. aureus* Newman genomic DNA with the following primers: 5'-CCCGGATCCTCTA-GAAAGGGCGGATTACTAATGATTAAAC-3' (SEQ ID NO: 7) and 5'-CCCCTGCAGTTATTTCTTTTCATTAT-CATTAAGTAC-3' (SEQ ID NO: 8). This sequence was cloned into the pOS1 P$_{lukAB}$-sslukA-6His vector with BamHI and PstI. Finally mature lukA was PCR-amplified with the following primers: 5'-CCCGGATC-CCATAAAGACTCTCAAGACCAAAAT-3' (SEQ ID NO: 9) and 5'-CCCTCTAGATTATCCTTCTTTATAAGGTTT-ATTG-3' (SEQ ID NO: 10). This sequence was cloned into the pOS1 P$_{lukAB}$-sslukA-6His-lukB vector with BamHI and XbaI to yield P$_{lukAB}$-sslukA-6His-lukA-lukB. Recombinant plasmids were transformed into *Escherichia coli* CH5α and transformants selected by ampicillin resistance. Positive clones were transformed into *S. aureus* Newman ΔlukAB (Dumont et al., "Characterization of a New Cytotoxin That Contributes to *Staphylococcus aureus* Pathogenesis," *Mol. Microbiol.* 79(3):814-825 (2011), which is hereby incorporated by reference in its entirety).

The protein was purified from *S. aureus* by growing the strain in tryptic soy broth (TSB) with 10 µg/ml chloramphenicol for 5 hrs at 37° C., 180 rpm to an OD$_{600}$ of ~1.5. The bacteria were then pelleted at 4000 rpm, 4° C. for 15 minutes and the supernatant was collected and filtered through 0.2 µm filters. The culture supernatant was incubated with nickel-NTA resin (Qiagen) in the presence of 10 mM immidazole for 30 minutes at 4° C. with agitation. The sample was applied to a column and washed with tris buffered saline (TBS: 50 mM Tris, 150 mM NaCl, pH 7.5) supplemented with 25 mM imidazole, and eluted with 500 mM imidazole. The protein was dialyzed in 1×TBS+10% glycerol at 4° C. overnight.

Biochemical Studies to Detect the Interaction of LukAB with Mac-1.

For detection of pull-down products with streptavidin, PMN-HL60 cells were incubated with EZ-link sulfo-NHS-LC-Biotin (Thermo Scientific) in cold PBS for 30 minutes at 4° C. with rotation. To quench the reaction cells were then washed with cold 100 mM glycine in cold PBS. The cells were resuspended in cold TBS with EDTA-free protease inhibitor cocktail (Thermo Scientific) and solubilized with 1% N-octyl-β-D-glucopyranoside (Affimetrix) for 30 minutes at 4° C. with rotation. The samples were centrifuged at 15000 rpm, 4° C. for 30 minutes and the supernatant containing the solubilized portion was collected. The solubilized portion (from approximately 2×10$^6$ cells) was incubated with 10 µg (5 µg/million cells) of His-LukAB or mock incubated with TBS for 30 minutes at 4° C. with rotation. The samples were incubated with 50 µl of nickel resin in the presence of 10 mM immidazole for 1 hour at 4° C. with rotation. The resin was washed with 1× PBS+50 mM Immidazole and the proteins were eluted with 1×PBS+500 mM Immidazole. The samples were boiled in 4×SDS boiling buffer and run on a 4-15% SDS-PAGE gradient (BioRad) at 80 V, followed by transfer to a nitrocellulose membrane at 30 V for 1 hour. The membrane was blocked with 0.01% tween in PBS for 1 hour, and then incubated with Streptavidin-Dylight 680 (Thermo Scientific) at 1:1000 for 1 hour. The membrane was dried and scanned using an Odyssey infrared imaging system (LI-COR Biosciences).

Pull-downs with PMN-HL60s lysates were also performed with His-tagged LukAB, His-tagged LukED (Alonzo et al., "*Staphylococcus aureus* Leucocidin ED Contributes to Systemic Infection by Targeting Neutrophils and Promoting Bacterial Growth In Vivo," *Mol. Microbiol.* 83(2):423-435 (2012), which is hereby incorporated by reference in its entirety) or His-tagged PVL (Alonzo et al., "CCR5 is a Receptor for *Staphylococcus aureus* Leukotoxin ED," *Nature* 493(7430):51-55 (2013), which is hereby incorporated by reference in its entirety) as described above without biotinylation where the samples were run on a 15% SDS-PAGE and transferred to a nitrocellulose membrane at 1 amp for 1 hour. The membrane was probed with an anti-CD11b antibody (clone 23843, R&D Systems), which was detected using an AlexaFluor-680-conjugated anti-rabbit secondary (Invitrogen) antibody diluted 1:25,000, and the Odyssey imaging system.

For the pull-down with purified LukAB and purified Mac-1, 4 µg recombinant Mac-1 (R&D Systems) was incubated with 4 µg of purified recombinant His-LukAB, His-LukED, His-PVL, or PBS in the presence of 0.1% N-octyl-β-D-glucopyranoside for 30 minutes at 4° C. with rotation. The samples were incubated with 100 µl nickel resin, washed, and eluted as described above. The boiled samples in 4× SDS buffer were run on 4-15% gradient gels. One set of samples was processed by immunoblot with an anti-CD11b antibody as described above. For the other set of samples, the gel was stained with the total protein stain Sypro Ruby (Invitrogen) at the manufactures instructions.

PMNs (2×10$^7$) were solubilized with 1% N-octyl-β-D-glucopyranoside, the soluble portion was incubated with 20 µg His-LukAB, and complexes were purified with nickel resin as described above. The samples were run on a 4-15% gradient gel and stained with Sypro Ruby. The entire lane was excised from the gel and subjected to mass spectrometry analysis.

Fluorescence Activated Cell Sorting (FACS) Analysis.

Cells were stained with fluorescently-conjugated antibodies for 30 minutes on ice, then washed with 1× PBS+2% FBS+0.05% sodium azide (FACS buffer). For unconjugated anitbodies, cells were stained with primary antibodies antibodies for 30 minutes on ice, washed with FACS buffer, stained for 30 min on ice with fluorescently-conjugated secondary antibody, then washed with FACS buffer. All FACS data were acquired on an LSRII flow cytometer (BD Biosciences) using FACSDiva software. Data were analysed using Flowjo software (Treestar).

Antibodies for FACS Analysis.

Antibodies used for surface staining of primary human cells and human cell lines included the following: anti-CD11b-APC (clone ICRF44), anti-CD18-PE/Cy5 (clone TS1/18), anti-CD11a-FITC (clone HI111), and anti-CD11c-PerCP/Cy5.5 (clone Bu15) (Biolegend). Antibodies for mapping the interaction between LukAB and CD11b included the un-conjugated versions of the human specific antibodies listed above as well as the LM2/1 (Santa Cruz) and CBRM1/5 (BioLegend) anti-CD11b clones. To detect the I-less CD11b, goat anti-CD11b (polyclonal) with anti-goat IgG-APC (R&D Systems) was used.

Antibodies used for surface staining of primary murine cells 293T cells expressing murine Mac-1 included the following: anti-CD11b-APC (clone M1/70), and anti-Ly-6G-FITC (clone 1A8) (BD Pharmingen).

Transfection of HEK293T Cells with CD11b cDNA.

HEK293T cells were incubated with the pCMV6-XL5 plasmid containing full-length human CD11b cDNA (OriGene) or empty vector using Lipofectamine 2000 (Invitrogen) at the manufacturers instructions. Transfection efficiency was between 70-80% as determined with a GFP-producing control vector, and CD11b surface levels were determined 48 hours later by flow cytometry. At this time susceptibility to LukAB or PVL was determined by adding 40 µg/ml of each toxin or PBS to the cells for 2 hours at 37° C., 5% $CO_2$. The cells were then washed and stained with α-CD11b-APC (clone ICRF44). Depletion of CD11b$^+$ cells was measured by flow cytometry where the % of CD11b$^+$ cells with PBS treatment was normalized to 100%.

Generation of the hCD11b I-Less Mutant by Overlap PCR.

Deletion of the I domain from human CD11b was achieved by overlap PCR where a 5' segment upstream of the I-domain and a 3' segment downstream of the I-domain were amplified from the pCMV6-XL5 vector containing human CD11b cDNA (OriGene). For amplification of the 5' segment of CD11b without the 5'UTR but with a Kozak sequence the following primers were used:

(SEQ ID NO: 11)
5'-TGACTCTAGACCACCATGGCTCTCAGAGTCCTTCTG-3'
and (SEQ ID NO: 12)
5'-GCTGCTACTTCCTGTCTGAGTTTGAGGACACCCTCGGAGG-3'.

For amplification of the 3' segment of CD11b the following primers were used:

(SEQ ID NO: 13)
5'-CCTCCGAGGGTGTCCTCAAACTCAGACAGGAAGTAGCAGC-3'
and (SEQ ID NO: 14)
5'-TTTGCGGCCGCAGCCCAAGCCCGTCCTGTC-3'.

The two segments were joined by overlap PCR using the following primers: 5'-TGACTCTAGACCACCATGGCTCTCAGAGTCCTTCTG-3' (SEQ ID NO: 15) and 5'-TTTGCGGCCGCAGCCCAAGCCCGTCCTGTC-3' (SEQ ID NO: 16). Wild type (WT) human CD11b was also amplified from the OriGene plasmid with this last set of primers. The amplified sequences were cloned into pLenti-CMV-GFP-Puro (Addgene) using XbaI and NotI resulting in the pLenti-CMV-hCD11b-puro and pLenti-CMV-I-less.hCD11b-puro constructs. Recombinant plasmids were transformed into *E. coli* RecA⁻ 5α (New England BioLabs) and transformants were selected by ampicillin resistance.

Lentivirus-Based Knockdown of Human CD11b and CD18 and Overexpression of CD11b.

Lentiviral shRNA expression vector stocks were produced as described previously (Unutmaz et al., "Cytokine Signals are Sufficient for HIV-1 Infection of Resting Human T Lymphocytes," *J. Exp. Med.* 189(11):1735-1746 (1999), which is hereby incorporated by reference in its entirety) by calcium phosphate co-transfection of HEK293T cells with the following plasmids: pMDG gag-pol, pRSV-Rev, pVSV-G Env, and pLKO.1 CD11b or CD18 shRNA constructs purchased from SIGMA MISSION TRC 1.5 library. The following shRNA sequences were used: 5'-CCGGCG-CAATGACCTTCCAAGAGAACTCGAGTTCTCTTG-GAAGGTCATTGCG TTTTT-3' (SEQ ID NO: 17) for CD11b and 5'-CCGGGAAACCCAGGAAGACCA-CAATCTCGAGATTGTGGTCTTCCTGGGTTTC TTTTT-3' (SEQ ID NO: 18) for CD18. Supernatants were collected 48 hrs later, centrifuged, filtered to remove cell debris, and titered on Jurkat cells as described previously (Unutmaz et al., "Cytokine Signals are Sufficient for HIV-1 Infection of Resting Human T Lymphocytes," *J. Exp. Med.* 189(11): 1735-1746 (1999), which is hereby incorporated by reference in its entirety). HL60 cells were transduced with the respective viruses or empty vector control virus for 72 hours followed by selection with 2 μg/ml puromycin, which was determined to kill ~95-99% of untransduced cells. Surviving cells were expanded knockdown was confirmed by flow cytometry.

Lentiviral expression vector stocks were generated by co-transfecting HEK293T cells with the following plasmids: pMDG gag-pol, pRSV-Rev, pVSV-G Env, and pLenti-CMV-hCD11b-puro or pLenti-CMV-I-less.hCD11b-puro as previously described (Hofmann et al., "The Vpx Lentiviral Accessory Protein Targets SAMHD1 for Degradation in the Nucleus," *J. Virol.* 86(23):12552-12560 (2012), which is hereby incorporated by reference in its entirety) using Lipofectamine 2000. Virus was collected and HL60 cells were transduced as described above. Surviving cells were expanded and WT and I-less CD11b surface levels were confirmed by flow cytometry. Cells were sorted using the BD Biosciences FACSAria cell sorter to collect the top 25% of cells staining with an α-CD11b antibody.

Elicitation of Peritoneal Exudate Cells (PECs).

Murine PECs were elicited with heat killed *S. aureus* as described previously (Alonzo et al., "CCR5 is a Receptor for *Staphylococcus aureus* Leukotoxin ED," *Nature* 493(7430): 51-55 (2013), which is hereby incorporated by reference in its entirety).

Generation of FITC-LukAB.

To generate recombinant N-terminal fluorescein labeled LukAB, the mature protein coding sequence of LukA from *S. aureus* Newman genomic DNA was PCR-amplified where a cysteine was added to the N-terminus after the signal sequence using the following primers: 5'-CCCCGGATCC TGTAATTCAGCTCATAAAGACTCTCAAG-3' (SEQ ID NO: 19) and 5'-CCCTCTAGATTATCCTTCTT-TATAAGGTTTATTG-3' (SEQ ID NO: 20). Amplified sequences were cloned into the P*lukAB*-sslukA-6His-lukB using BamH1 and Xbal as described above. Recombinant plasmids were transformed into *E. coli* CH5α and transformants were selected by ampicillin resistance. Positive clones were transformed into *S. aureus* Newman ΔlukAB (Dumont et al., "Characterization of a New Cytotoxin That Contributes to *Staphylococcus aureus* Pathogenesis," *Mol. Microbiol.* 79(3):814-825 (2011), which is hereby incorporated by reference in its entirety). The protein was purified from *S. aureus* as described above and labeled with 20 fold molar excess Alexa Fluor-488 C5 maleimide (Invitrogen) overnight at 4° C. with agitation. Excess dye was removed through dialysis with 10 kDa molecular weight cutoff dialysis cassettes in TBS with 10% glycerol. Activity of the labeled protein was confirmed by cytotoxicity assays.

Purification of Flag-Tagged CD11b I-Domains from *E. coli*.

To generate recombinant human and mouse CD11b I domain with a C-terminal 3× Flag tag and N-terminal 6×-His tag, human and mouse I domain was amplified from the pCMV6-XL5 and pCMV-Entry human and mouse CD11b cDNA constructs (OriGene) respectively. For human I-domain amplification with a C-terminal 6×-glycine linker followed by a 3×-Flag tag the following primers were used:

(SEQ ID NO: 21)
5'-TTT*CATATG*GGATCCAACCTACGGCAGCAG-3'
and (SEQ ID NO: 22)
5'-TTT*CTCGAG*TTA<u>CTTGTCATCGTCATCCTTGTAATCGATATCAT
GATCTTTATAATCACCGTCATGGTCTTTGTAGTCTCCTCCTCCTCC
TCCCGCAAAGATCTTCTCCCGAAG</u>-3'.

For murine I-domain amplification with a C-terminal 6×-glycine linker followed by a 3×-Flag tag the following primers were used:

(SEQ ID NO: 23)
5'-TTT*CATATG*GGCTCCAACCTGCTGAGGCC-3'
and (SEQ ID NO: 24)
5'-TTT*CTCGAG*TTA<u>CTTGTCATCGTCATCCTTGTAATCGATATCATG
ATCTTTATAATCACCGTCATGGTCTTTGTAGTCTCCTCCTCCTCCTCC
CTGCAAAGATCTTTTCCTGAAGCTG</u>-3'.

Amplified sequences were cloned into the pET15b vector (Novagen) with NdeI and XhoI so that the vector-encoded 6×-His tag is at the N-terminus of the I domains. Recombinant plasmids were transformed into *E. coli* T7 LysY lacQ and transformants and were selected by ampicillin resistance.

To purify the proteins from *E. coli*, the strains were grown at 37° C., 180 rpm in Luria-Bertani (LB) broth supplemented with 100 μg/ml ampicillin to an $OD_{600}$ of 0.5, and then induced with 1 mM IPTG for 3 hours at 37° C., 180 rpm. Bacteria were lysed through and lysates were incubated with nickel resin. His-tagged I domains were eluted with 500 mM imidazole.

Dot Blot Analysis to Determine LukAB-CD11b I-Domain Interactions.

5-0.156 μg of purified recombinant human and mouse CD11b I domain were absorbed to PVDF membranes using a dot blot vacuum (BioRad). The membranes were blocked with 2% BSA in 1×TBS for 1 hour followed by incubation with 5 μg/ml purified FITC-LukAB in TBS+2% BSA for 1 hour. For competition assays, 10-fold excess (50 μg/ml) unlabeled purified LukAB or PVL was also incubated with the membranes. Binding of FITC-LukAB was detected using the Odyssey infrared imaging system and quantified by densitometry using the AlphaImager software.

Surface Plasmon Resonance Analysis of LukAB Binding to Mac-1 and CD11b I-Domains.

Surface Plasmon resonance (SPR) was run using the Biacore T100 system (GE) as described previously (Huergo et al., "The Campylobacter Jejuni Dps Protein Binds DNA in the Presence of Iron or Hydrogen Peroxide," *J. Bacteriol.* (2013), which is hereby incorporated by reference in its entirety). Briefly, recombinant MAC-1 (R&D Systems), or recombinant I-Domain (mouse and human) were immobilized onto flow cell 2-4 of a series S sensor chip CM5 (GE) using the NHS capture kit, and flow cell 1 was run as a blank immobilization. LukAB and its mutants were run at concentrations ranging from 0.625-25 ug/mL using multi cycle kinetics with at least three experiments performed for each interaction. Single cycle kinetics was utilized to optimize concentrations prior to completion of multi cycle kinetics. The running buffer for all SPR experiments was 1×PBS at pH 6.8.

Cytotoxicity Assays.

Cells were intoxicated as described previously (Dumont et al., "Characterization of a New Cytotoxin That Contributes to *Staphylococcus aureus* Pathogenesis," *Mol. Microbiol.* 79(3):814-825 (2011), which is hereby incorporated by reference in its entirety). Briefly, $1\times10^5$ cells/well were intoxicated for 1-2 hours at 37° C., 5% $CO_2$ with the indicated concentrations of purified recombinant LukAB. Cell membrane damage, toxin pore formation, or cellular metabolism was evaluated with SYTOX green (Invitrogen), ethidium bromide (MP biomedicals), or CellTiter (Promega) respectively. For experiments with anti-Integrin antibodies, the antibodies were added 30 minutes prior to intoxication at room temperature and were present during the intoxication.

In Vitro and Ex Vivo Infections with *S. Aureus*.

These infections were performed as described previously with ΔlukAB, ΔlukAB chromosomally complimented with lukAB (ΔlukAB::lukAB) or the wild type (WT) USA300 clonal type LAC strains. Briefly, to determine killing of PMNs or PMN-HL60s by extracellular *S. aureus*, normalized USA300 was incubated with $1\times10^5$ cells/well at multiplicity of infections (MOIs) of 100, 50, 10, or 1, at 37° C., 5% $CO_2$ for 1-2 hours. For experiments with anti-Integrin antibodies, the antibodies were added 30 minutes prior to infection at room temperature and were present during the infection. Membrane disruption was evaluated using SYTOX green.

To determine growth rebound of phagocytosed *S. aureus* upon infection with PMN-HL60s, opsonized USA300 was synchronized with $1\times10^5$ PMN-HL60s/well at an MOI of 10 through centrifugation. At 30, 60, 120, and 180 min post-synchronization the PMN-H160s were lysed with saponin and serially diluted. Recovered bacteria were determined by counting colony-forming units CFUs.

PMN or PMN-HL60 membrane damage following infection with opsonized *S. aureus* was also determined by preparing the PMNs and bacteria as described above, where SYTOX green was added at 1-2 hours post synchronization.

Fluorescence Microscopy.

PMNs were infected with opsonized LAC WT, ΔlukAB, and ΔlukAB::lukAB strains transformed with pOS1-$P_{sarA}$-sodRBS-sgfp to constitutively express GFP.

To determine the location of CD11b in PMNs phagocytosing *S. aureus*, PMNs were pre-stained with the anti-CD11b-APC (ICRF44) antibody or respective isotype control (mouse IgG1κ-APC, clone MOPC-21, BioLegend) for 30 min on ice. PMNs were then plated at $3\times10^6$ cells in 35 mm glass bottom microwell dishes (20 mm microwell, 1.5 thickness, uncoated, MatTek) and synchronized with GFP-USA300 at a MOI of 10. A plate of PMNs was mock infected to detect CD11b staining in the absence of infection. Polyclonal anti-LukA antibody affinity purified from rabbit sera and Lysostaphin (Ambi Products LLC) were added to eliminate the effect of extracellular bacteria. After a 10-minute incubation with lysostaphin at 37° C., 5% $CO_2$ the cells were fixed with 2% paraformaldehyde and 0.1 M lysine in 1×PBS for 30 minutes on ice. The plates were washed with 1×PBS and stored in 1×PBS at 4° C. until imaging. Images were captured using a 60× oil objective on an Applied Precision PersonalDV live-cell imaging system comprised of am Olympus IX-71 inverted microscope, a CoolSnap HQ2 CCD camera, and SoftWorx suite with z-stack capabilities. Images were processed using ImageJ software.

To image GFP-USA300 and ethidium bromide incorporation in the presence of neutralizing antibody, PMNs were pre-treated with anti-CD11b (LM2/1, Santa Cruz) antibody or the respective isotype control (mouse IgG1, Santa Cruz) for 30 minutes at room temperature. PMNs were then infected as described above and images were captured at 0 and 30 minutes post-synchronization using a 40× objective on a Axiovert 40 CFL fluorescent microscope (Zeiss), Axiocam ICc 1 (Zeiss), and the Zen software from Zeiss.

Statistics. Data were analyzed using a one-way ANOVA and Tukey's multiple comparisons post-test (GraphPad Prism version 5.0; GraphPad Software) unless indicated otherwise. Data presented here are from one of at least three independent experiments that gave similar results unless otherwise indicated Example 1

LukAB Mediates the Cytotoxic Properties of *S. Aureus* in Human Neutrophils

Human polymorphonuclear cells were exposed to secreted proteins isolated from isogenic wildtype and lukAB mutant (ΔlukAB) methicillin sensitive *S. aureus* (MSSA) and methicillin resistant *S. aureus* (MRSA) strains. Exposure of the PMNs to secreted proteins from wildtype *S. aureus* strains resulted in potent cell death as examined by the CellTiter assay (FIG. 1A; black bars). In contrast, exposure of PMNs to secreted proteins from the lukAB mutant strains resulted in significantly reduced cell death. (FIG. 1A; grey bars). The lack of cytotoxic activity exerted by the ΔlukAB strain was reversed by transforming the strain with a plasmid expressing lukAB (ΔlukAB/pLukAB) as shown in FIG. 1A (white bars). These data indicate that LukAB is responsible for the cytotoxic properties of both MSSA and MRSA strains towards human neutrophils.

The importance of LukAB is further supported by the findings that LukAB is critical for *S. aureus* survival during ex vivo infection of human whole blood and primary human PMNs (FIG. 1B; compare black (WT) and white (ΔlukAB/pLukAB) bars to grey bars (ΔlukAB). Additionally, the contribution of LukAB to *S. aureus* pathogenesis in vivo using a mouse model of kidney abscess formation has been determined. In this model, mice are challenged with a retro-orbital injection containing *S. aureus* and then euthanized 96 hours post-infection. Bacterial burden in kidney homogenates are used as a measure of *S. aureus* pathogenesis. Using this model, an isogenic mutant lacking lukAB exhibits a ~100-fold decrease in bacterial burden in renal tissue compared to WT CA-MRSA (FIG. 1C; grey bar). The phenotype of the lukAB mutant was partially complemented by expressing lukAB in trans with a plasmid (FIG. 1C; white bar). Collectively, these data indicate that LukAB is a virulence factor critical for *S. aureus* pathogenesis.

Figure 2:
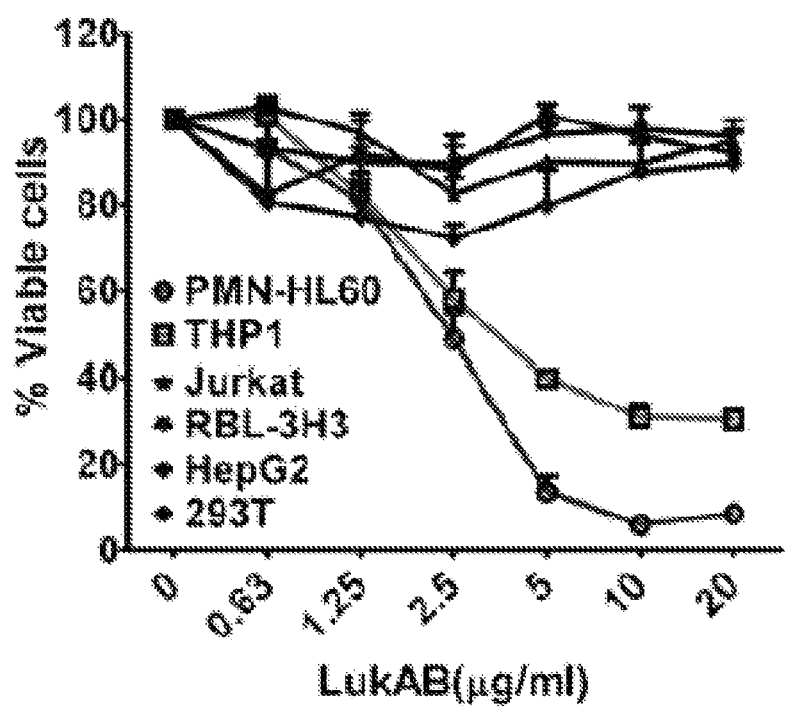
FIG. 2 is a dose response of LukAB induced cytotoxicity in different human cells. The graph shows viability of indicated cells upon intoxication with purified LukAB. Host cell viability was monitored with CellTiter, a reagent that monitors cellular metabolic activity. Results represent the average of triplicate samples+S.E.M.

Experiments with purified recombinant toxin have revealed that LukAB is necessary and sufficient for targeting and killing a variety of human cells including human PMNs, monocytes (both primary and THPI cells), macrophages, and dendritic cells (FIG. 2; see also Dumont et al., "Characterization of a New Cytotoxin that Contributes to *Staphylococcus aureus* Pathogenesis," *Mol. Microbiol.* 79(3):814-25, which is hereby incorporated by reference in its entirety). In contrast, mast cells (RBL3H3), lymphocytes (Jurkats), epithelial cells (HepG2 and 293T), and red blood cells are highly refractory to LukAB (FIG. 2). In addition, differentiation of the human myeloid cell line HL60 into PMN-like cells ("PMN-HL60") renders these cells highly susceptible to LukAB cytotoxicity (FIG. 2).

Figure 3:
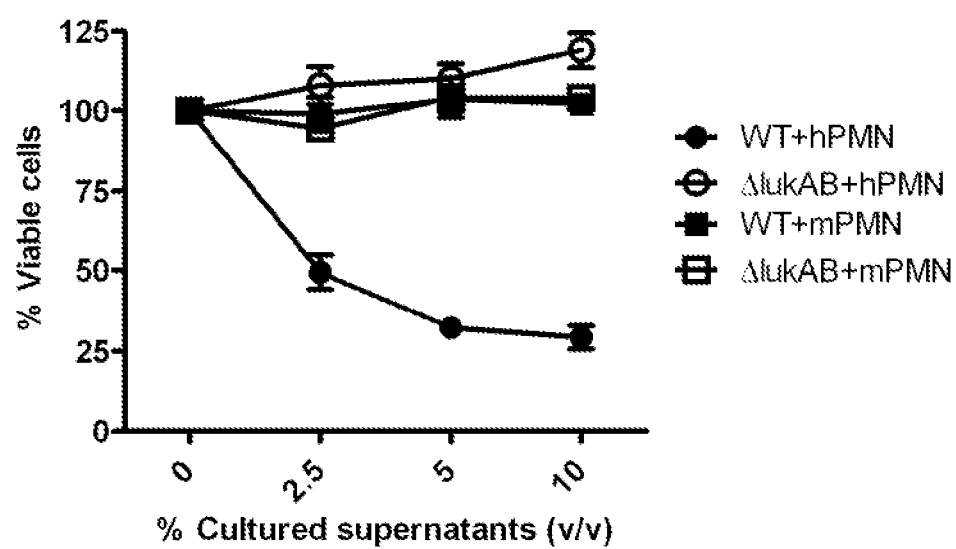
FIG. 3 show LukAB and S. aureus cytotoxicity towards primary neutrophils. The graph shows viability of human (hPMN) and primary murine (mPMN) neutrophils upon intoxication with secreted proteins isolated from isogenic wildtype (WT) and ΔlukAB mutant MSSA strains. Host cell viability was monitored with CellTiter, a reagent that monitors cellular metabolic activity. Results represent the average of at least six independent samples±S.E.M.

The data presented above indicate that LukAB targets and kills human phagocytes (FIG. 2). Importantly, experiments employing primary murine neutrophils have revealed that LukAB appears to be human specific, since no or little cytotoxicity is observed when secreted proteins isolated from isogenic wildtype *S. aureus* are incubated with murine cells (FIG. 3). These data have tremendous implications because they suggest that murine models of infection do not fully measure the contribution of LukAB, which based on the studies with human cell lines, is the most important leukotoxin produced by *S. aureus*. Thus, identification of the cellular determinant(s) that render human phagocytes susceptible to LukAB would enable the generation of transgenic animals that would better represent the pathobiology of *S. aureus* infection in humans.

Example 2

LukAB Directly Interacts with Integrin αM/β2 (Mac-1 or CR3)

Figures 4A, 4B, 4C, 4D:
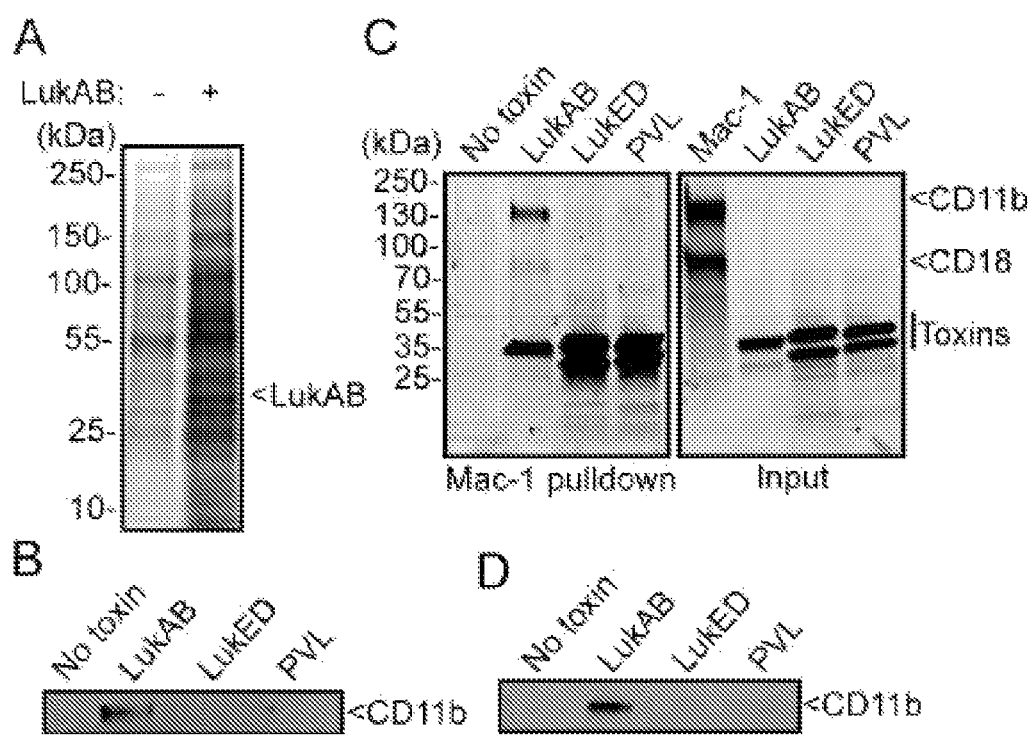
FIGS. 4A-4D show that LukAB directly interacts with the human integrin Mac-1 (CD11b/CD18).

To identify host proteins that interact with LukAB, a pull-down assay was performed with PMN-HL60 cells, which are short-lived neutrophil-like cells differentiated from the HL60 myeloid cell line that are extremely sensitive to LukAB (Dumont et al., "Characterization of a New Cytotoxin That Contributes to *Staphylococcus aureus* Pathogenesis," *Mol. Microbiol.* 79(3):814-825 (2011), which is hereby incorporated by reference in its entirety). The lysates were incubated with a His-tagged LukAB and a nickel column was used to isolate toxin-host protein complexes. The surface proteins on the PMN-HL60 cells were biotinylated prior to incubation with LukAB so that the host proteins could be visualized using fluorescently conjugated streptavidin (FIG. 4A). By employing this technique, a large number of host proteins were observed to be associated with LukAB (FIG. 4A). The pull-down was repeated with primary human PMNs isolated from human blood without biotinylation, and the identity and quantity of the cellular factors enriched in the pull-down with LukAB were determined by mass spectrometry. The most abundant LukAB-interacting cellular surface proteins were CD18 and CD11b (Table 1), which are respectively the α and β components of the integrin complex known as integrin αM/β2, CR3, or Mac-1, herein referred to as Mac-1. The association of LukAB, but not LukED or PVL, with CD11b was confirmed by immunoblot with a CD11b specific antibody (FIG. 4B). A specific and direct interaction between LukAB and Mac-1 was established when a pull-down was conducted with purified recombinant toxin and purified receptor. A total protein stain revealed that LukAB, but not LukED or PVL, could pull down both the CD11b and CD18 subunits of the purified Mac-1 complex which are about 150 and 95 kDa respectively (FIG. 4C). Immunoblot further validated the presence of CD11b in the pull-down with LukAB but not the other toxins (FIG. 4D).

TABLE 1

Mass spectometry analysis of LukAB-interacting cellular factors

| Identified Proteins (≥3 peptides) | Accession Number | Molecular Weight | # of peptides |
|---|---|---|---|
| Integrin alpha-M | ITAM_HUMAN | 127 kDa | 17 |
| Serum albumin | ALBU_HUMAN (+2) | 69 kDa | 13 |
| Integrin beta 2 | B4E0R1_HUMAN (+1) | 77 kDa | 12 |
| Cntm_P13645 | Cntm_P13645 | 24 kDa | 10 |
| Pyruvate kinase isozymes M1/M2 | KPYM_HUMAN | 58 kDa | 9 |
| cDNA FLJ78440 | A8K494_HUMAN (+2) | 78 kDa | 8 |
| Plastin-2 | PLSL_HUMAN (+2) | 70 kDa | 8 |
| Myeloperoxidase | PERM_HUMAN | 84 kDa | 7 |
| Actin | ACTG_HUMAN (+1) | 42 kDa | 7 |
| cDNA FLJ55635 | B4E0S6_HUMAN (+1) | 90 kDa | 7 |
| Glyceraldehyde-3-phosphate dehydrogenase | G3P_HUMAN (+2) | 36 kDa | 6 |
| Coronin-1A | COR1A_HUMAN | 51 kDa | 6 |
| Bactericidal permeability-increasing protein | BPI_HUMAN | 54 kDa | 6 |
| cDNA FLJ55493 | B4DMF5_HUMAN (+3) | 57 kDa | 5 |
| Protein S100-A8 | S10A8_HUMAN | 11 kDa | 5 |
| Mitogen-activated protein kinase 1 | MK01_HUMAN | 41 kDa | 5 |
| cDNA FLJ75120 | A8K345_HUMAN (+1) | 42 kDa | 5 |
| Hemoglobin subunit beta | HBB_HUMAN | 16 kDa | 5 |
| Adipocyte plasma membrane-associated protein | APMAP_HUMAN | 46 kDa | 5 |
| ATP synthase subunit beta | A8K4X0_HUMAN (+2) | 57 kDa | 5 |
| Putative uncharacterized protein LCN2 | A6NII8_HUMAN (+7) | 23 kDa | 5 |
| Heat shock 70kDa protein 1A | A8K5I0_HUMAN (+1) | 70 kDa | 5 |
| Malic enzyme | B2R8J2_HUMAN (+1) | 65 kDa | 5 |
| Endoplasmic reticulum resident protein ERp44 | ERP44_HUMAN | 47 kDa | 4 |
| Peptidoglycan recognition protein | PGRP_HUMAN | 22 kDa | 4 |
| SFPQ protein | Q6PIX2_HUMAN (+3) | 55 kDa | 4 |
| Hemoglobin subunit alpha | HBA_HUMAN (+1) | 15 kDa | 4 |
| Adenylyl cyclase-associated protein | B2RDY9_HUMAN (+4) | 52 kDa | 4 |
| Transketolase | A8K089_HUMAN (+6) | 68 kDa | 4 |
| cDNA, FLJ92148 | B2R4M6_HUMAN (+1) | 13 kDa | 4 |

TABLE 1-continued

Mass spectometry analysis of LukAB-interacting cellular factors

| Identified Proteins (≥3 peptides) | Accession Number | Molecular Weight | # of peptides |
|---|---|---|---|
| cDNA FLJ76817 | A8K525_HUMAN (+2) | 54 kDa | 3 |
| CD63 antigen | CD63_HUMAN (+1) | 26 kDa | 3 |
| Alpha-enolase | ENOA_HUMAN | 47 kDa | 3 |
| E3 ubiquitin-protein ligase CBL | CBL_HUMAN | 100 kDa | 3 |
| Guanine nucleotide-binding protein G(i) | GNAI2_HUMAN (+1) | 40 kDa | 3 |
| cDNA FLJ53963 | B4E3A8_HUMAN (+1) | 39 kDa | 3 |
| 6-phosphogluconate dehydrogenase | 6PGD_HUMAN (+3) | 53 kDa | 3 |
| Catalase | CATA_HUMAN | 60 kDa | 3 |
| Glucose-6-phosphate isomerase | G6PI_HUMAN (+3) | 63 kDa | 3 |
| Myosin-9 | MYH9_HUMAN (+1) | 227 kDa | 3 |
| Beta-adrenergic receptor kinase 1 | ARBK1_HUMAN | 80 kDa | 3 |
| Protein tyrosine phosphatase | B1ALS2_HUMAN (+2) | 147 kDa | 3 |
| Alpha-actinin-1 | ACTN1_HUMAN (+5) | 103 kDa | 3 |

In order to better characterize the direct interaction of LukAB with Mac-1 surface plasmon resonance (SPR) analysis was performed, which indicated that LukAB binds to Mac-1 in a dose-dependent and saturable manner resulting in a dissociation constant (Kd) of approximately 38.4 nM (Table 2).

TABLE 2

SPR analysis of LukAB/Mac-1 interactions

| Protein + LukAB | Disassociation constant (Kd) |
|---|---|
| human recombinant Mac-1 | $3.84 \times 10^{-8}$ M ($\pm 2.61 \times 10^{-8}$) |
| human recombinant I domain | $1.92 \times 10^{-9}$ M ($\pm 1.13 \times 10^{-9}$) |
| murine recombinant I domain | 1.06M ($\pm 0.89$) |

Example 3

Figures 5A, 5B, 5C, 5D, 5E, 5F:
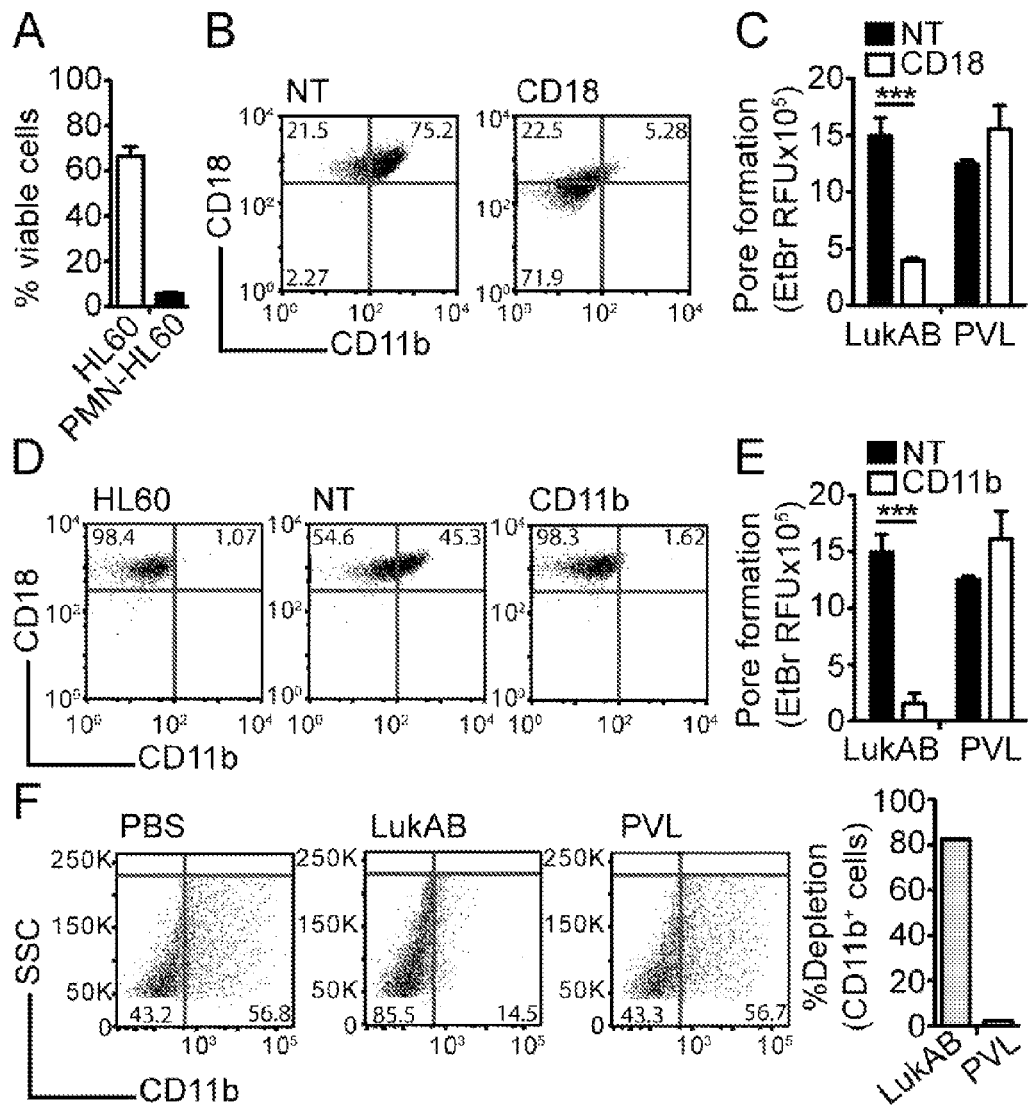
FIGS. 5A-5F demonstrate that CD11b is necessary and sufficient for LukAB-mediated killing of host cells.

The CD11b Subunit of Mac-1 is Necessary and Sufficient to Render Cells Susceptible to LukAB In order to provide a link between the susceptibility of cells to LukAB and Mac-1, HL60 cells were transduced with viruses containing non-targeting shRNA (NT shRNA) or with CD18 shRNA. To enhance the susceptibility of these cells to LukAB, the stably-transduced HL60 cell lines were differentiated to PMN-HL60s (FIG. 5A), and the effect of the shRNAs on the cell surface levels of CD18 and CD11b were confirmed by flow cytometry (FIG. 5B). Compared to NT shRNA cells, the CD18 shRNA cells were markedly depleted of CD18 (FIG. 5B). Because CD18 is required for the stability and surface localization of all the integrin α subunits (Weber et al., "Characterization of Lymphocyte Function-Associated Antigen 1 (LFA-1)-Deficient T Cell Lines: The AlphaL and Beta2 Subunits are Interdependent for Cell Surface Expression," J. Immunol. 158(1):273-279 (1997); Springer et al., "Inherited Deficiency of the Mac-1, LFA-1, p150,95 Glycoprotein Family and Its Molecular Basis," J. Exp. Med. 160(6):1901-1918 (1984), which are hereby incorporated by reference in their entirety), CD11b was also depleted in the CD18 shRNA cells (FIG. 5B). Thus, by targeting CD18 a Mac-1 depleted cell line was generated. Intoxication of the CD18 shRNA cells with purified LukAB revealed that Mac-1 is required for the formation of LukAB pores (FIG. 5C). In contrast, PVL formed pores in a Mac-1 independent manner, indicating that LukAB and PVL exploit different cellular determinants to exert their cytotoxicity (FIG. 5C).

Figure 6:
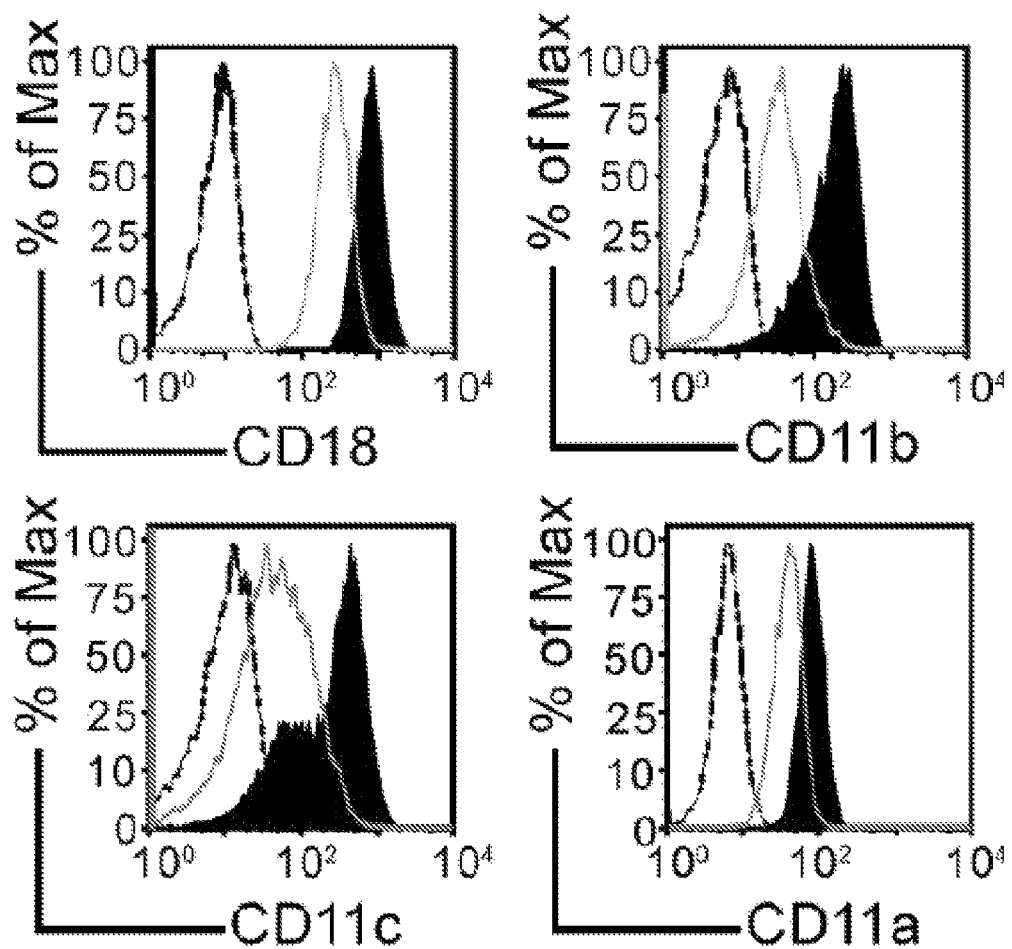
FIG. 6 shows that knockdown of CD18 results in depletion of multiple β2 integrins on the PMN-HL60 cell surface. CD18, CD11b, CD11c, and CD11a cell surface levels as determined by flow cytometry with specific antibodies in NT (solid black) and CD18 shRNA (grey line) in PMN-HL60 cells compared to an isotype control antibodies (black line).

In addition to Mac-1, PMN-HL60s are decorated with CD11a/CD18 (LFA) and CD11c/CD18 (p150/95), and depletion of CD18 resulted in a reduction in the surface levels of these β2 integrins as well (FIG. 6). To ensure that the knockdown of the Mac-1 complex was responsible for the increased resistance to LukAB and not the general knockdown of β2 integrins, HL60 cells were stably transduced with CD11b-targeting shRNA. This strategy resulted in marked depletion of CD11b with no notable effect on CD18 levels (FIG. 5D). In fact, the Mac-1 levels observed on the cells transduced with the CD11b-targeting shRNA resembled those of the parental HL60 cells (FIG. 5D). Depletion of CD11b rendered the cells resistant to LukAB pores, but not to PVL pores (FIG. 5E). These findings demonstrate that CD11b is crucial for rendering cells susceptible to LukAB.

To determine whether CD11b is sufficient to render cells susceptible to LukAB, a gain of function experiment was performed. It has been shown that HEK293T cells can support CD11b surface localization in the absence of CD18 (Solovjov et al., "Distinct Roles for the Alpha and Beta Subunits in the Functions of Integrin AlphaMbeta2," J. Biol. Chem. 280(2):1336-1345 (2005), which is hereby incorporated by reference in its entirety). Therefore, these cells were transiently transfected with either a plasmid encoding CD11b or an empty plasmid, and CD11b surface levels were determined via flow cytometry (FIG. 5F). Intoxication of these cells with LukAB, but not PVL, resulted in depletion of the majority (80-90%) of the CD11b+ HEK293T cells, confirming that CD11b is necessary and sufficient to render cells susceptible to LukAB (FIG. 5F).

Example 4

Figures 7A, 7B, 7C, 7D, 7E:
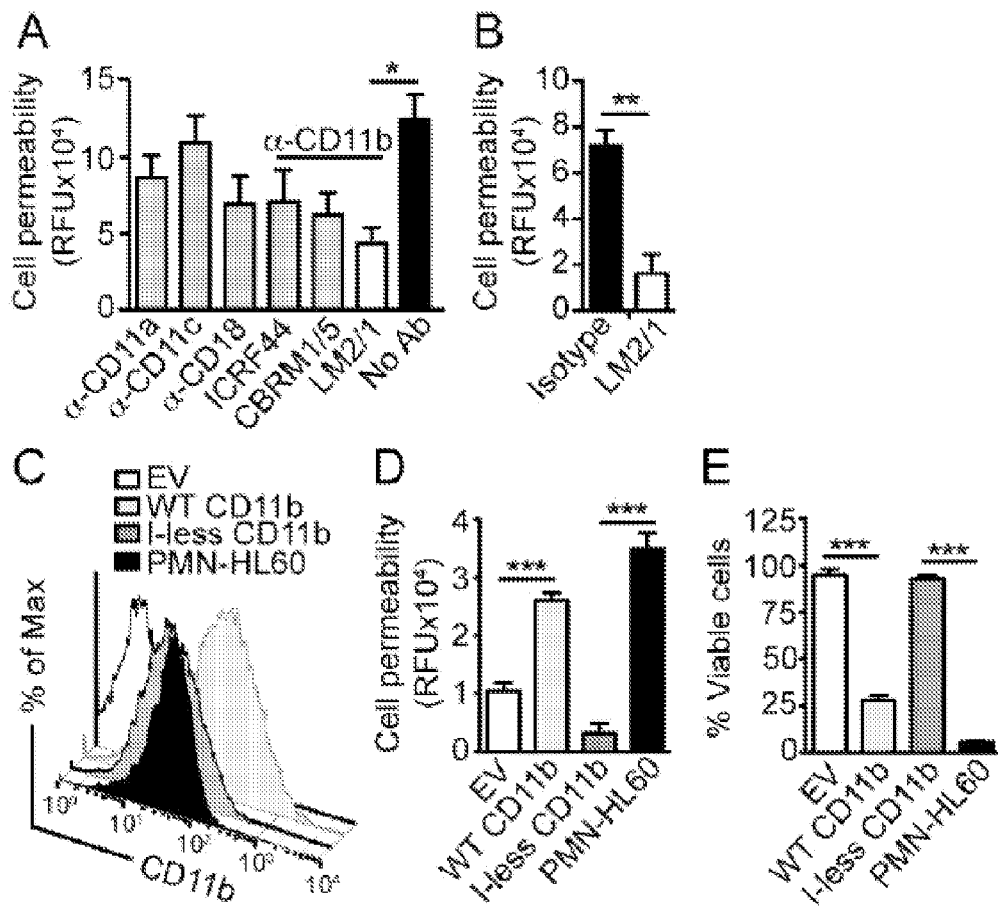
FIGS. 7A-7E demonstrate that LukAB targets the I-domain of CD11b to kill cells.

The I-domain of CD11b is Required for LukAB-Mediated Toxicity Towards Target Cells Whether LukAB cytotoxicity could be blocked with CD11b specific antibodies was examined. Prior to intoxication with LukAB, primary PMNs were pre-treated with three different antibodies targeting CD11b, as well as antibodies against CD18, CD11a, and CD11c. Although all three CD11b antibodies and the CD18 antibody displayed some degree of blocking LukAB toxicity, only the LM2/1 CD11b antibody significantly inhibited LukAB activity when compared to an untreated cells or an isotype control (FIGS. 7A-7B).

The LM2/1 antibody recognizes the CD11b I-domain (or A-domain), which is where most endogenous Mac-1 ligands bind through a metal ion-dependent adhesion site (MIDAS) (Arnaout et al., "Integrin Structure, Allostery, and Bidirectional Signaling," *Annu. Rev. Cell Dev. Biol.* 21:381-410 (2005), which is hereby incorporated by reference in its entirety). Based on the LM2/1 blocking data, it was hypothesized that the I-domain of CD11b was required for LukAB-mediated killing of target cells. To address this possibility, a mutated CD11b was constructed where the I-domain was deleted using overlap PCR as previously described (Yalamanchili et al., "Folding and Function of I Domain-Deleted Mac-1 and Lymphocyte Function-Associated Antigen-1," *J. Biol. Chem.* 275(29):21877-21882 (2000), which is hereby incorporated by reference in its entirety). It has been established that the deletion of the I-domain does not affect the interaction of CD11b with CD18 or the interaction between Mac-1 and endogenous ligands that do not require the I-domain (Yalamanchili et al., "Folding and Function of I Domain-Deleted Mac-1 and Lymphocyte Function-Associated Antigen-1," *J. Biol. Chem.* 275(29):21877-21882 (2000), which is hereby incorporated by reference in its entirety). HL60 cells were transduced with virus made from constructs containing wild type (WT) CD11b, I-less CD11b, or an empty vector control. These cells were chosen because they are highly resistant to LukAB and have low levels of CD11b (FIGS. 5A and 5D). If the I-domain is necessary for cytotoxicity, exogenous WT CD11b would render these cells as susceptible as PMN-HL60 cells, where as an I-less version of CD11b would not. Following transduction and stable integration, the levels of CD11b on the surface of the HL60 cell lines was evaluated by flow cytometry with an α-CD11b antibody that recognizes both the WT and I-less versions of CD11b (FIG. 7C). Both WT and I-less CD11b were surface exposed at levels comparable to or higher than that of PMN-HL60 cells (FIG. 7C). Exogenous WT CD11b rendered HL60 cells susceptible to LukAB as evidenced by increased membrane damage and cell death compared to the empty vector control HL60 cells (FIGS. 7D-7E). The level of susceptibility exhibited by the HL60 cells with exogenous WT CD11b was comparable to differentiated PMN-HL60 cells. In contrast, HL60 cells with exogenous I-less CD11b were highly resistant to LukAB-mediated cytotoxicity despite having equivalent levels of surface CD11b to PMN-HL60 cells (FIG. 7C-7E).

Example 5

Figures 8A, 8B, 8C, 8D, 8E:
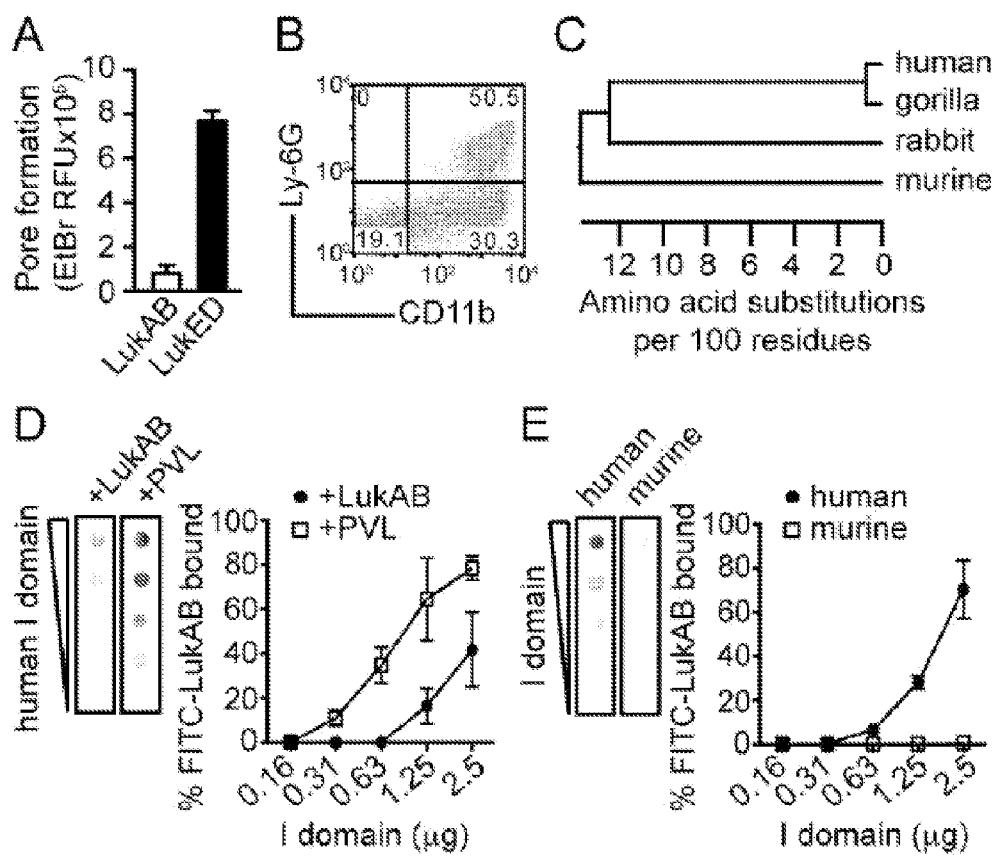
FIGS. 8A-8E shows that LukAB preferentially binds to the human CD11b I-domain compared to the murine CD11b I-domain.

LukAB Displays Higher Affinity for Human CD11b I-Domain Compared to Murine CD11b I-Domain Purified LukAB has been shown to be highly cytotoxic towards human and monkey PMNs, intermediately toxic towards rabbit PMNs, and least toxic towards murine PMNs (FIG. 3) (Malachowa et al., "*Staphylococcus aureus* Leukotoxin GH Promotes Inflammation," *J. Infect. Dis.* 206(8): 1185-1193 (2012), which is hereby incorporated by reference in its entirety). These findings suggest that LukAB targets blood-purified PMNs in a species-specific manner. Murine peritoneal exudate cells (PECs), which are highly susceptible to LukED, are resistant to LukAB (FIG. 8A). PECs mostly consist of recruited PMNs (Ly6G$^+$/CD11b$^+$), and monocytes and macrophages (Ly6G$^-$/CD11b$^+$), all of which have high levels of surface CD11b (FIG. 8B).

In view of the species specificity of LukAB together with the necessity of the CD11b I-domain for toxin activity (FIG. 7C-7D), the conservation of this domain from different species was examined. Alignment of the amino acid sequences of the human, gorilla, rabbit, and mouse CD11b I-domains revealed that as expected, gorilla is the most similar to human (98.6% identity), followed by rabbit (79.1% identity), and then murine (78.1% identity) (FIG. 8C). These data correlate with the tropism of LukAB towards PMNs from these species (Malachowa et al., "*Staphylococcus aureus* Leukotoxin GH Promotes Inflammation," *J. Infect. Dis.* 206(8):1185-1193 (2012), which is hereby incorporated by reference in its entirety). To investigate if these differences could influence LukAB binding to the CD11b I-domain, a dot blot assay to detect LukAB-CD11b I-domain interaction was developed. A dose-dependent interaction between fluorescently labeled LukAB and the human CD11b I-domain was observed, which was competed off with excess unlabeled LukAB but not with unlabeled PVL (FIG. 8D). Comparison of LukAB binding to human versus murine CD11b I-domain using this assay revealed that LukAB preferentially binds to the human CD11b I domain (FIG. 8E). SPR analysis revealed that LukAB binds to the human CD11b I-domain with an approximate Kd of 1.92 nM, ~8-9 logs lower than that of the LukAB-murine CD11b I-domain interaction at 1.06 M (Table 1).

Example 6

Figures 9A, 9B:
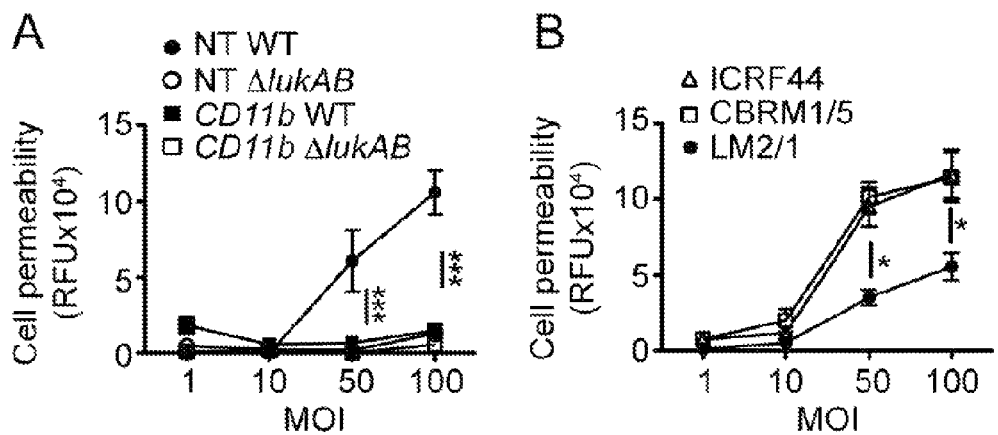
FIGS. 9A-9B demonstrate that CD11b renders cells susceptible to LukAB-mediated killing by extracellular S. aureus in ex vivo infections.

Extracellular *S. Aureus* Utilize CD11b to Cause LukAB-Mediated Cell Damage During Infection To establish a role for CD11b in *S. aureus* infections the NT or CD11b shRNA PMN-HL60 cells were infected with the CA-MRSA USA300 strain LAC or an isogenic mutant lacking LukAB (ΔlukAB). WT USA300 killed the NT PMN-HL60 cells in a LukAB-dependent manner (FIG. 9A). In contrast, when CD11b surface levels are reduced in these cells by shRNA (CD11b), the WT USA300 no longer causes cell damage and instead resembles the lukAB mutant strain (FIG. 9A).

Ex vivo infection of purified human PMNs with the USA300 strain was performed, and whether LukAB-mediated cell damage could be blocked through pre-treatment with anti-CD11b antibodies prior to infection was tested. These experiments revealed that the anti-I-domain LM2/1 antibody successfully neutralized USA300-mediated cell damage (FIG. 9B), thus establishing a role for LukAB-mediated targeting of the CD11b I-domain during *S. aureus*-PMN interaction.

Example 7

Figures 10A, 10B:
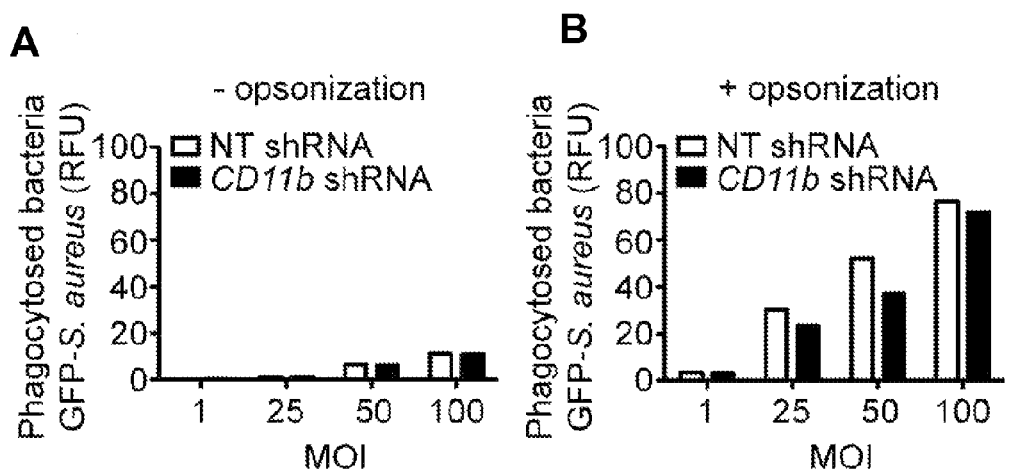
FIGS. 10A-10B shows that knockdown of CD11b does not affect opsonization-mediated phagocytosis of S. aureus by PMN-HL60 cells. Amount of phagocytosed bacteria in NT and CD11b shRNA PMN-HL60 cells infected with various MOI of GFP-USA300 with (FIG. 10B) or without (FIG. 10A) opsonization as determined by flow cytometry. Infections were performed in the presence of lysostaphin to eliminate GIP signal from extracellular bacteria.

Phagocytosed *S. Aureus* Exploits LukAB-Mediated Targeting of CD11b to Cause Cell Damage and Promote Escape from within It was recently established that LukAB-mediated cell damage post-phagocytosis promotes the early escape of USA300 from within PMNs and subsequent USA300 outgrowth. To determine if CD11b contributes to the intracellular cytotoxic activity of LukAB, the NT and CD11b shRNA PMN-HL60 cells were infected with opsonized USA300 and synchronized to promote phagocytosis. Importantly, depletion of CD11b did not influence phagocytosis of USA300 (FIGS. 10A-10B). Under these conditions, knockdown of CD11b abolished cell damage caused by the WT USA300 (FIG. 11A).

Figures 11A, 11B, 11C, 11D, 11E:
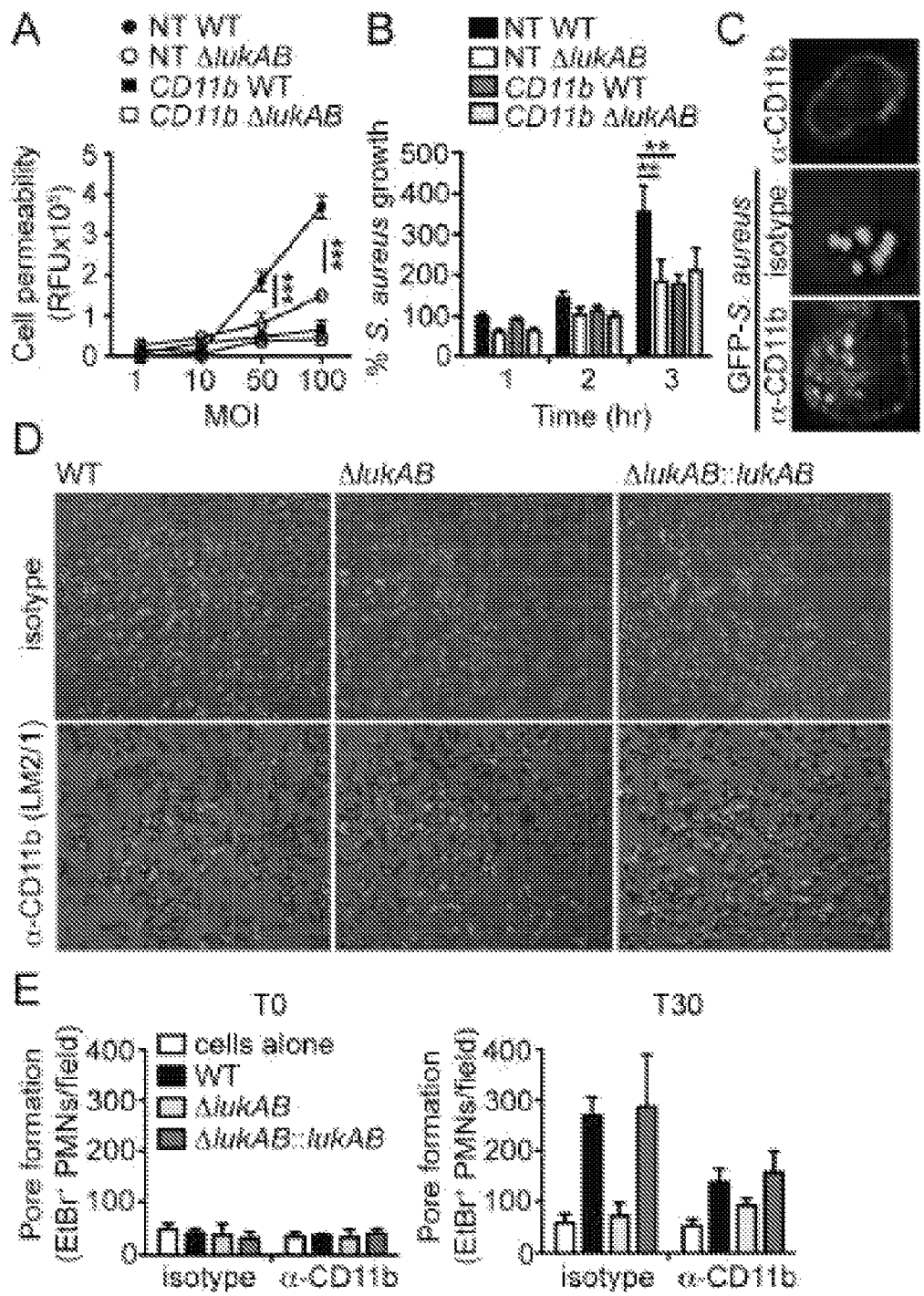
FIG. 11A-11E demonstrate that LukAB-mediated cellular damage and growth rebound of phagocytosed S. aureus is dependent on CD11b.

These experiment revealed that, phagocytosed USA300 employs LukAB to prevent PMN-HL60-mediated growth restriction (FIG. 11B). However, knockdown of CD11b eliminated the growth advantage of WT USA300 compared to the ΔlukAB mutant strain (FIG. 11B).

In order for CD11b to be utilized by phagocytosed *S. aureus* to escape from within PMNs, CD11b must be present in the phagosomal membrane surrounding *S. aureus*. To determine the location of CD11b during phagocytosis of *S. aureus*, human PMNs were pre-stained with a fluorescently labeled α-CD11b antibody or a fluorescently labeled isotype control, followed by infection with GFP-USA300. Infected cells were fixed post synchronization and imaged using an Applied Precision Personal DV live-cell imaging system with z-stack capability. In uninfected human PMNs the CD11b staining is dispersed across the plasma membrane of the cell (FIG. 11C). However, upon infection with USA300, CD11b was found to be associated with the phagocytosed GFP-USA300 (FIG. 11C).

Figure 12:
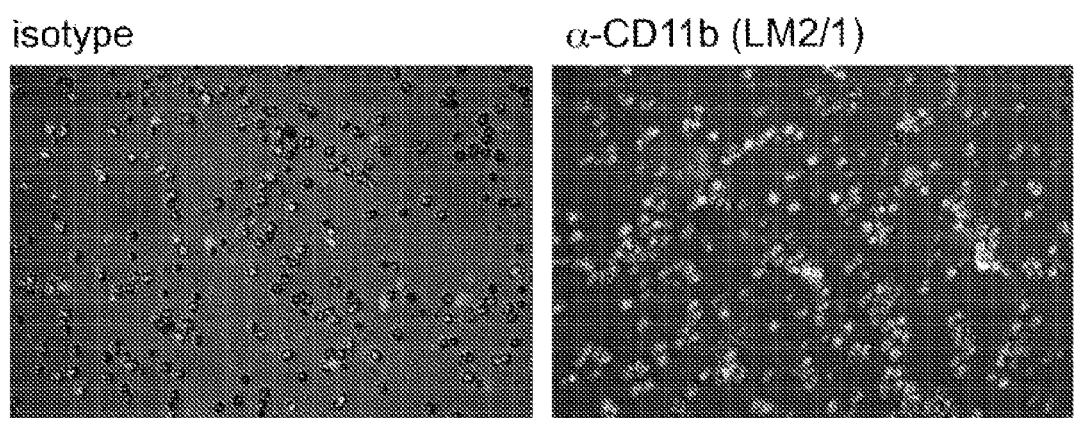
FIG. 12 shows that treatment of PMNs with the anti-CD11b LM2/1 antibody does not inhibit phagocytosis of S. aureus. Bacterial localization in PMNs infected with opsonized GFP-USA300 after pre-treatment with the α-CD11b LM2/1 antibody or an isotype control antibody. Fluorescent images were captured immediately following synchronization (T0). Background EtBr staining in red is also shown for this time point.

Neutralizing LM2/1 anti-CD11b antibody was used in an attempt to block the LukAB-mediated PMN damage caused by phagocytosed USA300. For these experiments, PMNs were pretreated with the LM2/1 antibody or an isotype control prior to infection with GFP-USA300 WT, isogenic ΔlukAB, or isogenic ΔlukAB chromosomally complemented with lukAB. These experiments were performed in the presence of lysostaphin and anti-LukA to eliminate extracellular bacteria and the potential contribution of extracellular LukAB, as well as the fluorescent dye ethidum bromide to measure pore-formation. Of note, pre-treatment with LM2/1 prior to infection does not block phagocytosis of *S. aureus* as the amount of GFP-USA300 observed within PMNs was similar regardless of LM2/1 treatment (FIG. 12). Phagocytosed USA300 causes LukAB-mediated pore formation at 30 minutes post synchronization when PMNs are pre-treated with isotype control antibody (FIG. 11D). In contrast, LM2/1 pre-treatment resulted in decreased LukAB-mediated pore formation (FIGS. 11D-11E), mimicking the phenotype observed with the lukAB mutant strain.

Discussion of Examples 1-7

This study describes the identification of CD11b of the Mac-1 integrin as a cellular molecule exploited by the *staphylococcal* leukotoxin LukAB to specifically target and kill cells. This conclusion is supported by the findings that LukAB directly interacts with the Mac-1 complex (specifically the I-domain of CD11b), and CD11b is necessary and sufficient to render cells susceptible to LukAB as evidenced by knockdown and gain of function analyses.

The identification of a cellular target that is specifically utilized by LukAB and not other bi-component toxins such as LukED and PVL highlights that the *staphylococcal* leukotoxins possess non-redundant mechanisms for targeting specific cell types. CCR5 was recently identified as a cellular receptor utilized by LukED to target and kill lymphocytes, macrophages and dendritic cells (Alonzo et al., "CCR5 is a Receptor for *Staphylococcus aureus* Leukotoxin ED," *Nature* 493(7430):51-55 (2013), which is hereby incorporated by reference in its entirety). However, monocytes and PMNs are killed by LukED in a CCR5-independent manner suggesting that additional cellular receptors may be utilized by LukED to target these cells (Alonzo et al., "CCR5 is a Receptor for *Staphylococcus aureus* Leukotoxin ED," *Nature* 493(7430):51-55 (2013), which is hereby incorporated by reference in its entirety). The fact that a single *staphylococcal* toxin may target multiple receptors and that each toxin may utilize distinct non-redundant receptors vastly increases the number of cell types that *S. aureus* can eliminate with an already extensive repertoire of toxins.

The targeted killing of innate immune cells such as PMNs is crucial to the pathogenesis of *S. aureus* as well as a number of other human pathogens. Mac-1 is expressed on all of the cells targeted by LukAB (Dumont et al., "Characterization of a New Cytotoxin That Contributes to *Staphylococcus aureus* Pathogenesis," *Mol. Microbiol.* 79(3):814-825 (2011), which is hereby incorporated by reference in its entirety) including PMNs, macrophages, monocytes, and dendritic cells (Ho & Springer, "Mac-1 Antigen: Quantitative Expression in Macrophage Populations and Tissues, and Immunofluorescent Localization in Spleen," *J. Immunol.* 128(5):2281-2286 (1982), which is hereby incorporated by reference in its entirety), and is involved in multiple cellular functions such as phagocytosis, cellular activation, cell-mediated killing and chemotaxis (Solovjov et al., "Distinct Roles for the Alpha and Beta Subunits in the Functions of Integrin AlphaMbeta2," *J. Biol. Chem.* 280(2):1336-1345 (2005); Hynes R. O., "Integrins: Bidirectional, Allosteric Signaling Machines," *Cell* 110(6):673-687 (2002), which are hereby incorporated by reference in their entirety). The present study demonstrates that both extracellular *S. aureus* and phagocytosed *S. aureus* employ LukAB to cause PMN damage during infection by targeting CD11b. The finding that CD11b surrounds phagocytosed *S. aureus*, links CD11b to the LukAB-mediated escape of *S. aureus* from the phagosome.

The identification of human CD11b I-domain as a cellular target of LukAB provides an explanation for the observed species specificity exhibited by this toxin. The affinity of LukAB toward the murine CD11b I-domain is ~8-9 logs less than that observed towards the human CD11b I-domain, which correlates to the previously reported susceptibility of murine PMNs (Malachowa et al., "*Staphylococcus aureus* Leukotoxin GH Promotes Inflammation," *J. Infect. Dis.* 206(8):1185-1193 (2012), which is hereby incorporated by reference in its entirety). The difference in binding affinity is most likely explained by the divergent sequence homology between the I-domains from these two species based on amino acid sequence alignments, which yielded a 78.1% identity between the two I-domains. Of note, it was observed that USA300 expresses lukAB in vivo in murine abscess, and that the toxin contributes to both the infection process and the bacterial burden in a murine renal abscess model (Dumont et al., "Characterization of a New Cytotoxin That Contributes to *Staphylococcus aureus* Pathogenesis," *Mol. Microbiol.* 79(3):814-825 (2011), which is hereby incorporated by reference in its entirety). Even though LukAB plays a role in this murine model of renal abscess formation, the marked resistance of mouse PMNs to this toxin compared to human PMNs suggests that mouse models underestimate the true contribution of LukAB to *S. aureus* pathobiology in humans. The species-specific activities of an expanding number of virulence factors produced by *S. aureus* (e.g. superantigens, CHIPS, PVL, LukAB) (Vandenesch et al., "*Staphylococcus aureus* Hemolysins, Bi-Component Leukocidins, and Cytolytic Peptides: A Redundant Arsenal of Membrane-Damaging Virulence Factors?" *Front Cell Infect. Microbiol.* 2:12 (2012); Rooijakkers et al., "Staphylococcal Innate Immune Evasion," *Trends Microbiol.* 13(12):596-601 (2005), which are hereby incorporated by reference in their entirety) highlight the limitations of the animal models currently employed to study *S. aureus* pathogenesis. Thus, improved animal models are paramount for understanding the full virulence potential of *S. aureus*, which is a prerequisite for the development of effective drugs that can combat this important human pathogen.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A method of treating *Staphylococcus aureus* infection and/or a condition resulting from a *S. aureus* infection in a subject comprising:
   selecting a subject having or at risk of having *S. aureus* infection and
   administering a CD11b inhibitor to the selected subject under conditions effective to treat *S. aureus* infection and/or a condition resulting from a *S. aureus* infection in the subject, wherein the CD11b inhibitor is selected from (i) a recombinant soluble polypeptide comprising the I-domain of CD11b, and (ii) an antibody that binds to the I-domain of CD11b.

2. The method of claim 1, wherein the *S. aureus* infection is a methicillin-resistant *S. aureus* (MRSA) infection or a methicillin sensitive *S. aureus* (MSSA) infection.

3. The method of claim 1, wherein the recombinant soluble polypeptide comprises an amino acid sequence corresponding to residues 147-337 of SEQ ID NO: 2.

4. The method of claim 1 further comprising
   administering, to the selected subject in conjunction with the CD11b inhibitor, an agent selected from the group consisting of an anti-infective agent, an antibiotic agent, and an antimicrobial agent.

5. The method of claim 1, wherein a condition resulting from *S. aureus* infection is treated, said condition being selected from the group consisting of skin wounds and infections, tissue abscesses, folliculitis, osteomyelitis, pneumonia, scalded skin syndrome, septicemia, septic arthritis, myocarditis, endocarditis, and toxic shock syndrome.

6. The method of claim 1, wherein said administering is carried out orally, by inhalation, by intranasal instillation, topically, transdermally, parenterally, subcutaneously, intravenous injection, intra-arterial injection, intramuscular injection, intraplurally, intraperitoneally, or by application to a mucous membrane.

7. The method of claim 1 further comprising:
   repeating said administering.

8. The method of claim 1, wherein the subject is an infant, a juvenile, or an adult.

9. The method of claim 1, wherein the subject is an immunocompromised infant, juvenile, or adult.

* * * * *

UNITED STATES PATENT AND TRADEMARK OFFICE
CERTIFICATE OF CORRECTION

PATENT NO. : 9,657,103 B2  
APPLICATION NO. : 14/398293  
DATED : May 23, 2017  
INVENTOR(S) : Torres et al.

Page 1 of 1

It is certified that error appears in the above-identified patent and that said Letters Patent is hereby corrected as shown below:

Column 1 at Lines 12-15, delete "This invention was made with government support under grant number 1R56AI091856-01A1 awarded by the National Institutes of Health. The government has certain rights in this invention." and insert --This invention was made with government support under R56 AI091856 awarded by National Institutes of Health. The government has certain rights in the invention.--

Signed and Sealed this
Twenty-eighth Day of August, 2018

Andrei Iancu
*Director of the United States Patent and Trademark Office*